(12) United States Patent
Berry et al.

(10) Patent No.: US 11,717,614 B2
(45) Date of Patent: *Aug. 8, 2023

(54) SYRINGE WITH ROLLING DIAPHRAGM

(71) Applicant: BAYER HEALTHCARE LLC, Whippany, NJ (US)

(72) Inventors: Dave Berry, Kittanning, PA (US); Kevin P. Cowan, Allison Park, PA (US); Martin J. Gibler, West Chester, OH (US); Michael A. Spohn, Fenelton, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 130 days.

This patent is subject to a terminal disclaimer.

(21) Appl. No.: 16/812,912

(22) Filed: Mar. 9, 2020

(65) Prior Publication Data

US 2020/0222634 A1    Jul. 16, 2020

Related U.S. Application Data

(63) Continuation of application No. 15/305,285, filed as application No. PCT/US2015/027582 on Apr. 24, 2015, now Pat. No. 10,583,256.

(Continued)

(51) Int. Cl.
*A61M 5/315* (2006.01)
*A61M 5/24* (2006.01)
*A61M 5/145* (2006.01)

(52) U.S. Cl.
CPC ........ *A61M 5/31513* (2013.01); *A61M 5/145* (2013.01); *A61M 5/14586* (2013.01);
(Continued)

(58) Field of Classification Search
CPC ............ A61M 5/14586; A61M 5/2425; A61M 5/31513; A61M 5/145; A61M 5/14546;
(Continued)

(56) References Cited

U.S. PATENT DOCUMENTS

| 352,715 A | 11/1886 | Sandmark |
| 798,093 A | 8/1905 | Edward |

(Continued)

FOREIGN PATENT DOCUMENTS

| CN | 103917269 A | 7/2014 |
| EP | 1086661 A2 | 3/2001 |

(Continued)

OTHER PUBLICATIONS

"International Preliminary Report on Patentability with Written Opinion from PCT/US2015/027582", dated Nov. 3, 2016.

*Primary Examiner* — Dung T Ulsh
(74) *Attorney, Agent, or Firm* — David Schramm; Joseph L. Kent; James R. Stevenson

(57) ABSTRACT

A syringe for a fluid delivery system includes a pressure jacket having a distal end, a proximal end, and a throughbore therebetween. The syringe further includes a rolling diaphragm having a proximal end with an end wall for engaging a plunger, a distal end received within the throughbore of the pressure jacket. The distal end of the rolling diaphragm has a nozzle and a sidewall extending between the proximal end and the distal end of the rolling diaphragm along a longitudinal axis. At least a portion of one of the sidewall and the end wall has non-uniform thickness. At least a portion of the sidewall is flexible and rolls upon itself when acted upon by the plunger such that an outer surface of the sidewall at a folding region is folded in a radially inward direction as the plunger is advanced from the proximal end to the distal end of the rolling diaphragm.

16 Claims, 64 Drawing Sheets

Related U.S. Application Data

(60) Provisional application No. 61/987,086, filed on May 1, 2014, provisional application No. 61/984,386, filed on Apr. 25, 2014.

(52) U.S. Cl.
CPC ....... *A61M 5/2425* (2013.01); *A61M 5/14546* (2013.01); *A61M 5/14566* (2013.01); *A61M 5/14593* (2013.01); *A61M 5/31515* (2013.01); *A61M 2005/14513* (2013.01); *A61M 2005/14553* (2013.01); *A61M 2205/36* (2013.01)

(58) Field of Classification Search
CPC .......... A61M 5/14566; A61M 5/14593; A61M 5/31515; A61M 2005/14513; A61M 2005/14553; A61M 2205/36
See application file for complete search history.

(56) References Cited

U.S. PATENT DOCUMENTS

| | | |
|---|---|---|
| 937,029 A | 10/1909 | Blessing et al. |
| 1,930,929 A | 10/1933 | Joel et al. |
| 2,062,285 A | 12/1936 | Sam et al. |
| 2,514,575 A | 7/1950 | Hein et al. |
| 2,592,381 A | 4/1952 | Blackman |
| 2,667,163 A | 1/1954 | Smith |
| 2,667,164 A | 1/1954 | Smith |
| 2,667,165 A | 1/1954 | Smith |
| 2,667,872 A | 2/1954 | Smith |
| 2,672,866 A | 3/1954 | Kater |
| 2,673,561 A | 3/1954 | Peterson, Jr. |
| 2,688,963 A | 9/1954 | Smith |
| 2,688,964 A | 9/1954 | Smith |
| 2,690,179 A | 9/1954 | Fox |
| 2,717,598 A | 9/1955 | Krasno |
| 2,805,662 A | 9/1957 | Lawshe et al. |
| 2,911,972 A | 11/1959 | Elinger |
| 2,935,067 A | 5/1960 | Bouet |
| 2,950,717 A | 8/1960 | Bonet |
| 3,155,281 A | 11/1964 | Stracey |
| 3,161,194 A | 12/1964 | Chapman |
| 3,161,195 A | 12/1964 | Taylor et al. |
| 3,172,577 A | 3/1965 | Hartung |
| 3,190,619 A | 6/1965 | Penney et al. |
| 3,231,139 A | 1/1966 | Bouet |
| 3,301,293 A | 1/1967 | Santelli |
| 3,340,869 A | 9/1967 | Bane |
| 3,353,537 A | 11/1967 | Knox et al. |
| 3,390,821 A | 7/1968 | Mullan |
| 3,411,503 A | 11/1968 | Santomieri |
| 3,442,424 A | 5/1969 | Prussin et al. |
| 3,471,058 A | 10/1969 | Latham et al. |
| 3,473,524 A | 10/1969 | Drewe |
| 3,474,844 A | 10/1969 | Lindstrom et al. |
| 3,506,163 A | 4/1970 | Rauh et al. |
| 3,557,788 A | 1/1971 | Swartz |
| 3,613,963 A | 10/1971 | Berkmuller |
| 3,618,846 A | 11/1971 | Poli |
| 3,826,409 A | 7/1974 | Chilcoate |
| 3,873,003 A | 3/1975 | Seiferth et al. |
| 3,938,514 A | 2/1976 | Boucher |
| 4,035,461 A | 7/1977 | Korth |
| 4,044,836 A | 8/1977 | Martin et al. |
| 4,064,879 A | 12/1977 | Leibinsohn |
| 4,066,080 A | 1/1978 | Sneider |
| 4,131,217 A | 12/1978 | Sandegren |
| 4,136,802 A | 1/1979 | Mascia et al. |
| 4,171,698 A | 10/1979 | Genese |
| 4,349,129 A | 9/1982 | Amneus |
| 4,392,491 A | 7/1983 | Takasugi et al. |
| 4,411,656 A | 10/1983 | Cornett, III |
| 4,526,296 A | 7/1985 | Berger et al. |
| 4,753,638 A | 6/1988 | Peters |
| 4,773,458 A | 9/1988 | Touzani |
| 4,850,807 A | 7/1989 | Frantz |
| 5,000,739 A | 3/1991 | Kulisz et al. |
| 5,201,438 A | 4/1993 | Norwood |
| 5,209,372 A | 5/1993 | Norwood |
| 5,236,204 A | 8/1993 | Hempel |
| 5,238,150 A | 8/1993 | Williams |
| 5,240,130 A | 8/1993 | Osbakk |
| 5,242,422 A | 9/1993 | Schneberger et al. |
| 5,269,428 A | 12/1993 | Gilbert |
| 5,333,761 A | 8/1994 | Davis et al. |
| 5,353,961 A | 10/1994 | Debush |
| 5,370,250 A | 12/1994 | Gilbert |
| 5,383,858 A | 1/1995 | Reilly et al. |
| 5,397,157 A | 3/1995 | Hempel et al. |
| 5,573,129 A | 11/1996 | Nagata et al. |
| 5,584,413 A | 12/1996 | Jung |
| 5,592,948 A | 1/1997 | Gatten |
| 5,609,580 A | 3/1997 | Kwiatkowski et al. |
| 5,615,791 A | 4/1997 | Vatelot et al. |
| 5,638,995 A | 6/1997 | Mazda |
| 5,683,369 A | 11/1997 | Tsukada |
| 5,758,789 A | 6/1998 | Shin et al. |
| 5,794,107 A | 8/1998 | Russell |
| 5,827,233 A * | 10/1998 | Futagawa ............. A61M 5/315 604/218 |
| 5,836,922 A | 11/1998 | Hansen et al. |
| 5,873,861 A | 2/1999 | Hitchins et al. |
| 5,899,889 A | 5/1999 | Futagawa et al. |
| RE36,377 E | 11/1999 | Gilbert |
| 5,979,326 A | 11/1999 | Ohinata |
| 6,054,194 A | 4/2000 | Kane |
| 6,062,437 A | 5/2000 | Mascitelli |
| 6,077,252 A | 6/2000 | Siegel |
| 6,105,815 A | 8/2000 | Mazda |
| 6,142,976 A | 11/2000 | Kubo et al. |
| 6,216,915 B1 | 4/2001 | Harman et al. |
| 6,224,577 B1 | 5/2001 | Dedola et al. |
| 6,250,505 B1 | 6/2001 | Petit |
| 6,306,191 B1 | 10/2001 | McInerney et al. |
| 6,315,761 B1 | 11/2001 | Shcherbina et al. |
| 6,319,235 B1 | 11/2001 | Yoshino |
| 6,322,535 B1 | 11/2001 | Hitchins et al. |
| 6,332,876 B1 | 12/2001 | Poynter et al. |
| 6,485,471 B1 | 11/2002 | Zivitz et al. |
| 6,558,358 B2 | 5/2003 | Rosoff et al. |
| 6,578,738 B1 | 6/2003 | Keller |
| 6,620,134 B1 | 9/2003 | Trombley, III et al. |
| 6,634,524 B1 | 10/2003 | Helmenstein |
| 6,652,489 B2 | 11/2003 | Trocki et al. |
| 6,702,143 B2 | 3/2004 | Wang |
| 6,716,195 B2 | 4/2004 | Nolan, Jr. et al. |
| 6,773,417 B2 | 8/2004 | Fitzgibbons et al. |
| 6,840,164 B2 | 1/2005 | Eastman |
| 6,866,039 B1 | 3/2005 | Wright et al. |
| 6,869,419 B2 | 3/2005 | Dragan et al. |
| RE38,770 E | 8/2005 | Gilbert |
| 6,974,443 B2 | 12/2005 | Reilly et al. |
| 7,004,213 B2 | 2/2006 | Hansen |
| 7,011,650 B2 | 3/2006 | Rosoff et al. |
| 7,192,549 B2 | 3/2007 | Hansen |
| 7,250,039 B2 | 7/2007 | Fitzgerald |
| 7,309,463 B2 | 12/2007 | Hansen |
| 7,419,478 B1 | 9/2008 | Reilly et al. |
| 7,513,378 B2 | 4/2009 | Mori et al. |
| 7,553,294 B2 | 6/2009 | Lazzaro et al. |
| 7,563,249 B2 | 7/2009 | Schriver et al. |
| 7,604,623 B2 | 10/2009 | Brunner et al. |
| 7,666,169 B2 | 2/2010 | Cowan et al. |
| 7,802,691 B2 | 9/2010 | Musalek et al. |
| 9,173,995 B1 | 11/2015 | Tucker et al. |
| 9,180,252 B2 | 11/2015 | Gelblum et al. |
| 9,199,033 B1 | 12/2015 | Cowan et al. |
| 9,474,857 B2 | 10/2016 | Riley et al. |
| 10,046,106 B2 | 8/2018 | Cowan et al. |
| 10,105,491 B2 | 10/2018 | Gelblum et al. |
| 10,857,345 B2 | 12/2020 | Uber, III et al. |
| 2001/0004466 A1 | 6/2001 | Heinz et al. |

(56) References Cited

U.S. PATENT DOCUMENTS

| | | |
|---|---|---|
| 2004/0249344 A1 | 12/2004 | Nemoto et al. |
| 2010/0091361 A1 | 4/2010 | Yuuki |
| 2010/0286650 A1 | 11/2010 | Fitzgerald |
| 2011/0282196 A1 | 11/2011 | Martz |
| 2012/0020911 A1 | 1/2012 | Seliktar et al. |
| 2012/0209111 A1 | 8/2012 | Cowan et al. |
| 2012/0253291 A1 | 10/2012 | Ivosevic et al. |
| 2013/0023048 A1 | 1/2013 | Kim et al. |
| 2013/0043273 A1 | 2/2013 | Lee et al. |
| 2013/0204130 A1 | 8/2013 | McArthur et al. |
| 2013/0211248 A1 | 8/2013 | Cowan et al. |
| 2013/0281940 A1 | 10/2013 | Gelblum et al. |
| 2017/0035974 A1 | 2/2017 | Berry et al. |
| 2019/0192770 A1 | 6/2019 | Spohn et al. |

FOREIGN PATENT DOCUMENTS

| | | | |
|---|---|---|---|
| EP | 2098258 A1 | 9/2009 | |
| EP | 3057648 A1 | 8/2016 | |
| FR | 1288915 A | 3/1962 | |
| GB | 2214819 A | 9/1989 | |
| GB | 2374143 A * | 10/2002 | ............... F03G 7/06 |
| GB | 2374143 A | 10/2002 | |
| WO | 9221391 A1 | 12/1992 | |
| WO | 9707841 A2 | 3/1997 | |
| WO | 0204049 A1 | 1/2002 | |
| WO | 2009038955 A1 | 3/2009 | |
| WO | 2010004206 A2 | 1/2010 | |
| WO | 2010014654 A1 | 2/2010 | |
| WO | 2011129175 A1 | 10/2011 | |
| WO | 2012061140 A1 | 5/2012 | |
| WO | 2012155035 A1 | 11/2012 | |
| WO | 2014027009 A1 | 2/2014 | |
| WO | 2015058088 A1 | 4/2015 | |
| WO | 2015066506 A2 | 5/2015 | |
| WO | 2015164783 A1 | 10/2015 | |
| WO | 2016058946 A1 | 4/2016 | |
| WO | 2016069711 A1 | 5/2016 | |
| WO | 2016069714 A1 | 5/2016 | |
| WO | 2016172467 A1 | 10/2016 | |
| WO | 2018053074 A1 | 3/2018 | |
| WO | 2019152978 A1 | 8/2019 | |

* cited by examiner

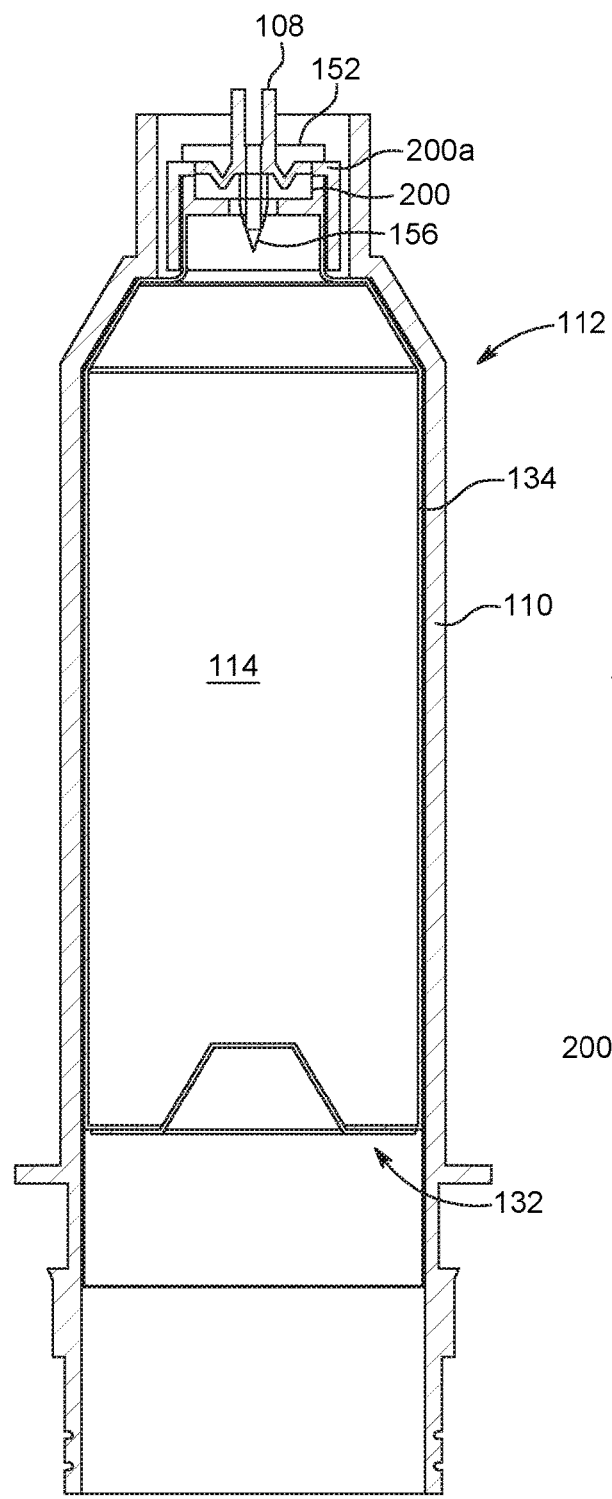
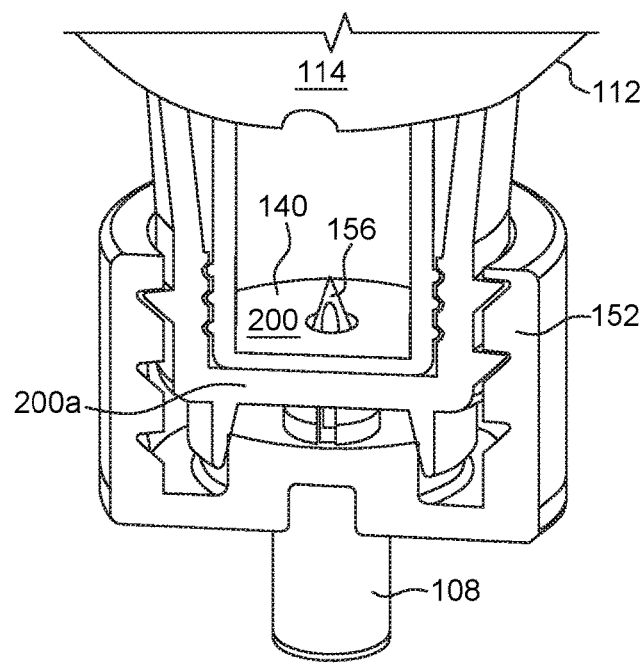
FIG. 58A
FIG. 58B

SYRINGE WITH ROLLING DIAPHRAGM

CROSS-REFERENCE TO APPLICATIONS

This application is a continuation application of U.S. application Ser. No. 15/305,285, filed Oct. 19, 2016, which was a U.S. national stage filing under 35 U.S.C. § 371 of International Application No. PCT/US2015/027582, filed Apr. 24, 2015, which claims priority to U.S. Provisional Patent Application No. 61/984,386, entitled "Syringe With Rolling Diaphragm" and filed on Apr. 25, 2014, and U.S. Provisional Patent Application No. 61/987,086, entitled "Syringe With Rolling Diaphragm" and filed on May 1, 2014, the disclosures of which are incorporated by reference herein in their entirety.

BACKGROUND OF THE DISCLOSURE

Field of the Disclosure

The present disclosure is related to syringes for use in the medical field and, more particularly, to syringes used in the medical field where the syringe includes a rolling diaphragm for selectively filling the syringe with a fluid and discharging the fluid from the syringe.

Description of Related Art

In many medical diagnostic and therapeutic procedures, a medical practitioner, such as a physician, injects a patient with one or more medical fluids. In recent years, a number of injector-actuated syringes and fluid injectors for pressurized injection of medical fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other molecular imaging procedures. In general, these fluid injectors are designed to deliver a preset amount of fluid at a preset pressure and/or flow rate.

In some injection procedures, the medical practitioner places a catheter or a needle connected to tubing, or other fluid delivery connection into a vein or artery of the patient. The catheter or the tubing is connected to either a manual or to an automatic fluid injection mechanism. Automatic fluid injection mechanisms typically include at least one syringe connected to at least one fluid injector having, for example, at least one powered linear piston. The at least one syringe includes, for example, a source of contrast and/or a source of flushing fluid. The medical practitioner enters settings into an electronic control system of the fluid injector for a fixed volume of contrast and/or saline and a fixed rate of injection for each.

The injected contrast and/or saline are delivered to a patient's vasculature through the catheter or needle inserted into the patient's body, such as the patient's arm or groin area. A dose of contrast is referred to as a bolus. Once the bolus of contrast is delivered to the desired site, that area is imaged using a conventional imaging technique, such as angiography imaging or scanning, CT, ultrasound, Mill, PET, and other molecular imaging procedures. The presence of the contrast becomes clearly visible against the background of the surrounding tissue.

A number of injector-actuated syringes and powered injectors for use in medical procedures have been developed. Typically, injectors have drive members, such as pistons, that connect to a syringe plunger. The syringe generally includes a rigid barrel with the syringe plunger being slidably disposed within the barrel. The drive members drive the plungers in a proximal and/or distal direction relative to a longitudinal axis of the barrel to aspirate a fluid into the syringe barrel or deliver the fluid from the syringe barrel.

It is well known that syringes used in the medical field are typically disposable and are discarded after one use. Although disposable syringes are typically made by mass production methods such as injection molding, such disposable syringes are relatively expensive due to the materials and precision involved in their manufacture. Accordingly, it remains desirable to develop improved designs of syringes to facilitate injection procedures.

SUMMARY OF THE DISCLOSURE

The present disclosure generally relates to syringe assemblies and to methods of forming syringe assemblies. The syringe assemblies may be useful in fluid delivery applications.

In one aspect, a rolling diaphragm for receiving a medical fluid therein may have a proximal end having an end wall for engagement with a plunger and a distal end received within a throughbore of a pressure jacket, the distal end having a nozzle. The rolling diaphragm may further include a sidewall extending between the proximal end and the distal end along a longitudinal axis. At least a portion of at least one of the sidewall and the end wall having non-uniform thickness At least a portion of the sidewall may be flexible and rolls upon itself when acted upon by the plunger such that an outer surface of the sidewall at a folding region is folded in a radially inward direction as the plunger is advanced from the proximal end to the distal end and such that the outer surface of the sidewall at the folding region is unfolded in a radially outward direction as the plunger is retracted from the proximal end to the distal end.

In another aspect, the end wall may have a radiused folding edge that transitions into a distally extending ramp having continuously increasing thickness. The end wall may have a plunger engagement portion protruding proximally from a central region of the ramp. The end wall may have one or more ribs protruding radially outward from the plunger engagement portion toward the radiused folding edge. The rolling diaphragm may have a conical shape that narrows from the proximal end toward the distal end. The conical shape may narrow continuously or discontinuously from the proximal end toward the distal end. The proximal end may be inverted from a first convex configuration to a second concave configuration upon engagement with the plunger. The outer surface of the sidewall may have one or more grooves recessed radially inward into the sidewall. The outer surface of the sidewall may have one or more projections protruding radially outward from the sidewall. In some aspects, the rolling diaphragm may have a spherical shape or an ellipsoid shape. The rolling diaphragm may have an elliptical cross-section having a major axis extending along the longitudinal axis and a minor axis extending perpendicular to the longitudinal axis.

In accordance with another aspect, the rolling diaphragm may have a first portion extending from an approximate longitudinal midpoint of the rolling diaphragm to the distal end and a second portion that is complementary in shape to the first portion and extending from the first portion to the proximal end. The rolling diaphragm may further have a pressure sleeve surrounding at least a portion of an outer portion of the sidewall. The pressure sleeve may have one or more openings extending through the sidewall of the pressure sleeve. The one or more openings may be connected to a vacuum source. A first portion distal of an approximate midpoint of the rolling diaphragm may have a first inner diameter, and a second portion proximal of the approximate midpoint of the rolling diaphragm may have a second inner diameter. The first inner diameter may be larger than the second inner diameter. A first portion of the sidewall distal of an approximate midpoint of the rolling diaphragm may have a first thickness, wherein a second portion of the sidewall proximal of the approximate midpoint of the rolling diaphragm may have a second thickness. The first thickness may be larger than the second thickness. The proximal end may have a rigid plunger monolithically formed with the proximal end. The plunger may be overmolded with the proximal end. The outer surface of the sidewall may be in contact with a rigid outer shell. The sidewall of the rolling diaphragm may separate from the rigid outer shell as the sidewall rolls upon itself during advancement of the plunger from the proximal end to the distal end. At least a portion of the outer surface of the sidewall of the rolling diaphragm is adhered to the rigid outer shell by an adhesive. The adhesive may be a pressure-activated adhesive. At least a portion of the outer surface of the sidewall may have an adhesive that adheres the outer surface of the sidewall with the plunger during advancement of the plunger from the proximal end to the distal end.

In accordance with another aspect, the sidewall may have a non-uniform thickness between the proximal end and the distal end. A proximal portion of the sidewall may have a thicker sidewall thickness than the distal portion of the sidewall. A proximal portion of the sidewall may have a thinner sidewall thickness than the distal portion of the sidewall. A heat-shrinkable layer may surround at least a portion of the outer surface of the sidewall. The folding region may initiate rolling of the sidewall as the plunger is advanced from the proximal end to the distal end of the rolling diaphragm. The outer surface of the sidewall may have a plurality of tabs, each tab having a first end connected to the outer surface of the sidewall and a second end protruding radially outward relative to the first end. Each of the plurality of tabs may be radially deflectable. The sidewall of the rolling diaphragm may have one or more indicia for indicating a presence of a liquid within an interior volume of the rolling diaphragm. An interior of the rolling diaphragm may be pre-filled with a medical fluid to be delivered to a patient. An interior of the rolling diaphragm may be filled with a medical fluid from a fluid source for delivery to a patient.

In accordance with another aspect, a fluid delivery system may include a fluid injector having at least one reciprocally operable piston, a plunger operably connectable to the piston, a pressure jacket releasably connectable to the fluid injector, and a rolling diaphragm disposed within the throughbore of a pressure jacket. The rolling diaphragm may have a proximal end with an end wall for engagement with a plunger, a distal end configured to be received at the distal end of the pressure jacket, and a sidewall extending between the proximal end and the distal end of the rolling diaphragm along a longitudinal axis. At least one of the end wall and at least a portion of the sidewall having a non-uniform thickness. The sidewall of the rolling diaphragm may be flexible and configured to roll upon itself such that an outer surface of the sidewall at a folding region is folded in a radially inward direction as the plunger is advanced from the proximal end to the distal end of the rolling diaphragm and such that the outer surface of the sidewall at the folding region is unfolded in a radially outward direction as the plunger is retracted from the proximal end to the distal end of the rolling diaphragm.

In accordance with another aspect, the plunger may have a skirt extending radially around a body of the plunger. An outer diameter of the skirt may be dimensioned such that the skirt is compressed against the sidewall of the rolling diaphragm to discharge fluid from the interior of the rolling diaphragm as the plunger is advanced in a distal direction. The plunger may have a fluid-filled cavity with a reciprocally movable piston extending into at least a portion of the fluid-filled cavity. The plunger may be monolithically formed with the proximal end of the rolling diaphragm. The plunger may have a groove shaped in a distal end of the plunger. The proximal end of the rolling diaphragm may have a projection configured for being inserted into and retained within the groove of the plunger. The groove may be T-shaped. The plunger may have a connection interface for releasably connecting to a piston of the fluid injector such that the plunger is reciprocally driven by the piston. The plunger may have a first threaded member and the proximal end of the rolling diaphragm may have a second threaded member. The first threaded member of the plunger may be releasably connectable with the second threaded member of the rolling diaphragm.

In another aspect, the distal end of the plunger may have one or more radially-expandable ribs. The distal end of the plunger may have one or more rotatable elements such that rotation of the one or more rotatable elements in a first direction causes an expansion of the radially-expandable ribs and rotation of the one or more rotatable elements in a second direction causes a retraction of the radially-expandable ribs. The distal end of the plunger may have a slot configured for receiving a projection on the proximal end of the rolling diaphragm. The plunger may be rotated after the projection on the proximal end of the rolling diaphragm is inserted into the slot to lock the plunger with the rolling diaphragm. The plunger may have a plurality of concentric elements arranged in a telescoping orientation relative to one another. Each of the plurality of concentric elements may be movable independently in a proximal or a distal direction. The plunger may be co-molded with the proximal end of the rolling diaphragm. The plunger may have a first element and a second annular element surrounding the first element. The first element may be movable relative to the second element between a first position and a second position. In the first position, the second element may engage the sidewall of the rolling diaphragm, and, in the second position, the second element may disengage the sidewall of the rolling diaphragm.

In another aspect, the plunger may be compressible by the piston such that the plunger expands radially outward to engage the sidewall of the rolling diaphragm when the piston moves in a distal direction. The plunger may have a first inner element and a second outer element, such that the first inner element may be movable relative to the second element between a first position and a second position. In the first position, the second outer element may be expanded radially outward to engage the sidewall of the rolling diaphragm. In the second position, the second outer element may be retracted radially inward to disengage the sidewall of the rolling diaphragm. The plunger may have an inner element, an elastic element wrapped around at least a portion of the inner element, and an expandable outer element surrounding the inner element and the elastic element. Upon rotation of the elastic element around the inner element in a first direction, the expandable outer element may be expanded radially outward. Upon rotation of the elastic element around the inner element in a second direction opposite the first direction, the expandable outer element may be contracted radially inward. An outer surface of the expandable outer element may be textured. The expandable outer element may have a slit extending in a longitudinal direction between a proximal end of the expandable outer element and the distal end of the expandable outer element.

In accordance with another aspect, the rolling diaphragm may have a radial lip that is inverted from a radially outward position to a radially inward position upon engagement by the plunger such that at least a portion of the plunger is retained between the proximal end of the rolling diaphragm and the radial lip. The plunger may have a central opening configured to receive a plunger engagement portion, such as a tab, protruding from the proximal end of the rolling diaphragm. The tab may be permanently secured within at least a portion of the central opening. At least a portion of the tab may be expanded radially outward after it is inserted into the central opening to retain the tab within the central opening. The tab may be adhesively secured within at least a portion of the central opening. The plunger may have a cylindrical plunger body having one or more projections protruding radially outward from an outer surface of the cylindrical plunger body. The one or more projections may be configured for engaging the sidewall of the rolling diaphragm. At least one of the one or more projections may be angled in a proximal direction from the proximal end to the distal end of the plunger. An outer surface of the plunger may have a first threaded portion and an inner surface of the sidewall of the rolling diaphragm has a second threaded portion. At least one of the first threaded portion and the second threaded portion may be discontinuous. The proximal end of the rolling diaphragm may have a proximally-extending connection element with a radial tab.

In another aspect, the piston may have a locking arrangement for releasably receiving the connection element. The locking arrangement may have an annular recess configured to receive at least a portion of the connection element and the radial tab, and a locking element selectively movable between a first position where the radial tab of the connection element is locked within the annular recess and a second position where the radial tab of the connection element is removable from the annular recess. The locking element may be slidable from the first position to the second position. The locking element may be rotatable from the first position to the second position. The sidewall of the rolling diaphragm may have one or more radially-protruding gripping elements that are inverted from a radially-outward facing position to a radially-inward facing position when the plunger engages the proximal end of the rolling diaphragm. The plunger may have one or more gripping elements that correspond to the gripping elements on the sidewall of the rolling diaphragm.

In another aspect, a syringe for a fluid delivery system may have a pressure jacket having a distal end, a proximal end, and a throughbore extending between the distal end and the proximal end. The syringe may further include a rolling diaphragm disposed within the throughbore of the pressure jacket. The rolling diaphragm may have a proximal end with an end wall configured for engagement with a plunger, a distal end configured to be received at the distal end of the pressure jacket, and a sidewall extending between the proximal end and the distal end of the rolling diaphragm along a longitudinal axis. At least one of the end wall and at least a portion of the sidewall having a non-uniform thickness. At least a portion of the sidewall of the rolling diaphragm may be flexible and configured to roll upon itself such that an outer surface of the sidewall at a folding region is folded in a radially inward direction as the plunger is advanced from the proximal end to the distal end of the rolling diaphragm and such that the outer surface of the sidewall at the folding region is unfolded in a radially outward direction as the plunger is retracted from the proximal end to the distal end of the rolling diaphragm.

In a further aspect, the pressure jacket may have a frusto-conical portion that terminates in an outlet portion configured to receive a nozzle of the rolling diaphragm. The proximal end of the pressure jacket may have a removable seal sealing the rolling diaphragm and a plunger prior to use. The pressure jacket may have a first portion and a second portion pivotally connected together by a hinge. The first portion and the second portion may be lockable in a closed state. The pressure jacket may have a removable closure for enclosing at least a portion of the rolling diaphragm. The removable closure may have a threaded end for engaging corresponding threads on the distal end of the pressure jacket. The proximal end of the pressure jacket may have a connection interface configured for releasably connecting to a fluid injector. The proximal end of the pressure jacket may have a connection interface configured for releasably connecting to a fluid injector. The distal end of the pressure jacket may have a removable closure for enclosing at least a portion of the rolling diaphragm. The pressure jacket may have a shield protruding radially outward from the proximal end, the shield configured for engaging at least a portion of a housing of a fluid injector. The pressure jacket may have an annular flange slidably mounted to an outer portion of the sidewall of the pressure jacket. The annular flange may be slidable between a first position for locking the pressure jacket with the injector and a second position for unlocking the pressure jacket from the injector.

In some aspects, the pressure jacket may be reusable with an unused rolling diaphragm after a used rolling diaphragm is removed from the pressure jacket. The pressure jacket may be disposable with the rolling diaphragm. The pressure jacket may have a first removable cap enclosing the distal end of the pressure jacket and a second removable cap enclosing the proximal end of the pressure jacket. The distal end of the pressure jacket may be expandable radially outward relative to the proximal end of the pressure jacket for inserting or removing the rolling diaphragm from the throughbore of the pressure jacket. The pressure jacket may be permanently connected with a fluid injector. The pressure jacket may be releasably connected with a fluid injector. An adapter may be provided, the adapter having a first end for connecting to the fluid injector and a second end for releasably receiving the proximal end of the pressure jacket. The pressure jacket may have a flange protruding radially outward from an outer surface of the sidewall of the pressure jacket. The flange may have one or more openings extending through the flange in an axial direction. A flexible fluid container may be provided within an interior of the pressure jacket. The flexible fluid container may surround the rolling diaphragm. The flexible fluid container may be positioned proximally from the rolling diaphragm within an interior of the pressure jacket. The pressure jacket may have a heating element for heating the rolling diaphragm.

In another aspect, the rolling diaphragm may have a nozzle monolithically formed with the sidewall of the rolling diaphragm. The nozzle may have a connector configured for connecting to a fluid path set. The connector may be a luer connector. The nozzle may have a piercable seal configured to seal an interior of the rolling diaphragm. The nozzle may have a first seal between the nozzle and the sidewall of the rolling diaphragm and a second seal at an interface for connecting the nozzle to a fluid path set. The nozzle may have a removable cap. A fluid path set may be provided, the fluid path set having a puncture element and a seal. The seal may have a seal surface that corresponds to a shape of the piercable seal on the nozzle of the rolling diaphragm.

Further details and advantages of the various aspects described in detail herein will become clear upon reviewing the following detailed description of the various aspects in conjunction with the accompanying drawing figures.

BRIEF DESCRIPTION OF THE DRAWINGS

FIG. 58A is a cross-sectional side view of a syringe in accordance with another aspect of the present disclosure.

FIG. 58B is a partial cross-sectional perspective view of a seal shown in FIG. 58A.

DESCRIPTION OF THE PREFERRED EMBODIMENTS

Figure 1:
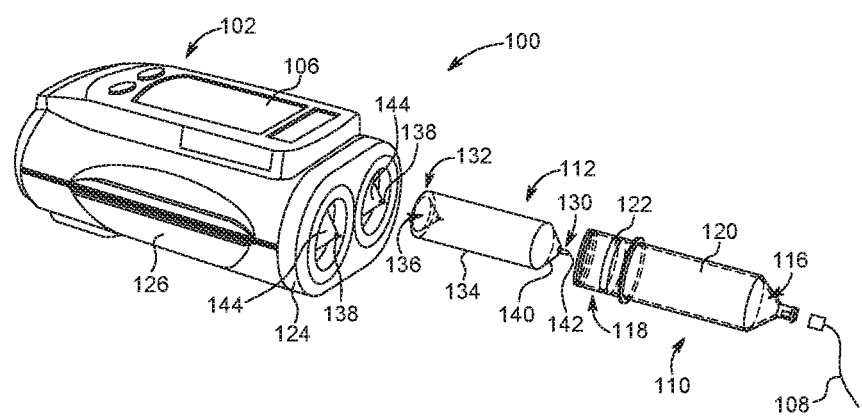
FIG. 1 is a perspective view of a fluid injection system according to one aspect of the present disclosure.

The illustrations generally show preferred and non-limiting aspects of the systems and methods of the present disclosure. While the description presents various aspects of the devices, it should not be interpreted in any way as limiting the disclosure. Furthermore, modifications, concepts, and applications of the disclosure's aspects are to be interpreted by those skilled in the art as being encompassed, but not limited to, the illustrations and descriptions herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe, a pressure jacket, and/or a rolling diaphragm, the term "proximal" refers to a portion of a syringe, a pressure jacket, and/or a rolling diaphragm nearest to an injector when a syringe, a pressure jacket, and/or a rolling diaphragm is oriented for connecting to an injector. The term "distal" refers to a portion of a syringe, a pressure jacket, and/or a rolling diaphragm farthest away from an injector when a syringe, a pressure jacket, and/or a rolling diaphragm is oriented for connecting to an injector. The term "radial" refers to a direction in a cross-sectional plane normal to a longitudinal axis of a syringe, a pressure jacket, and/or a rolling diaphragm extending between proximal and distal ends. The term "circumferential" refers to a direction around an inner or outer surface of a sidewall of a syringe, a pressure jacket, and/or a rolling diaphragm. The term "axial" refers to a direction along a longitudinal axis of a syringe, a pressure jacket, and/or a rolling diaphragm extending between the proximal and distal ends. It is to be understood, however, that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments (i.e., aspects, variants, variations) disclosed herein are not to be considered as limiting.

Referring to the drawings in which like reference characters refer to like parts throughout the several views thereof, the present disclosure is generally directed to syringe configured as a rolling diaphragm.

With reference to FIG. 1, a fluid delivery system 100 may have a fluid injector 102, such as an automated or powered fluid injector, adapted to interface with and actuate at least one rolling diaphragm 112 and pressure jacket 110, as described herein, each of which may be independently filled with a medical fluid, such as contrast media, saline solution, or any desired medical fluid. The injector 102 may be used during a medical procedure to inject the medical fluid into the body of a patient by driving a plunger 144 of the at least one rolling diaphragm 112 with at least one piston. The injector 102 may be a multi-rolling diaphragm injector, wherein two or more rolling diaphragms 112 with corresponding pressure jackets 110 may be oriented in a side-by-side or other relationship and include corresponding plungers 144 separately actuated by respective pistons associated with the injector 102. In embodiments with two rolling diaphragm/pressure jackets arranged in a side-by-side relationship and filled with two different medical fluids, the injector 102 may be configured to deliver fluid from one or both of the rolling diaphragms 112.

The injector 102 may be enclosed within a housing 126 formed from a suitable structural material, such as plastic or metal. The housing 126 may be of various shapes and sizes depending on the desired application. For example, the injector 102 may be a free-standing structure configured to be placed on the floor or may be a smaller design for placement on a suitable table or support frame. The injector 102 includes at least one port for connecting the at least one rolling diaphragm 112 and pressure jacket 110 to respective piston elements.

At least one fluid path set 108 may be fluidly connected with a nozzle 130 of the at least one syringe 104 comprising a rolling diaphragm 112 and pressure jacket 110 for delivering medical fluid from the at least one rolling diaphragm 112 to a catheter, needle, or other fluid delivery connection (not shown) inserted into a patient at a vascular access site. Fluid flow from the at least one syringe 104 may be regulated by a fluid control module (not shown). The fluid control module may operate various pistons, valves, and/or flow regulating structures to regulate the delivery of the medical fluid, such as saline solution and contrast, to the patient based on user selected injection parameters, such as injection flow rate, duration, total injection volume, and/or ratio of contrast media and saline. One embodiment of a suitable front-loading fluid injector that may be modified for use with the herein-described system including at least one rolling diaphragm and at least one interface for loading and releasably retaining of the at least one rolling diaphragm and pressure jacket with the fluid injector described herein with reference to FIG. 1 is disclosed in U.S. Pat. No. 5,383,858 to Reilly et al. which is incorporated by reference in its entirety. Another embodiment of relevant multi-fluid delivery systems that may be modified for use with the present system are found in U.S. Pat. No. 7,553,294 to Lazzaro et al.; U.S. Pat. No. 7,666,169 to Cowan et al.; International Patent Application No. PCT/US2012/037491 (published as WO 2012/155035); and United States Patent Application Publication No. 2014/0027009 to Riley et al.; all of which are assigned to the assignee of the present application, and the disclosures of which are incorporated herein by reference. Other embodiments may include new fluid injector systems designed to include various embodiments of the rolling diaphragm described herein.

Figure 2:
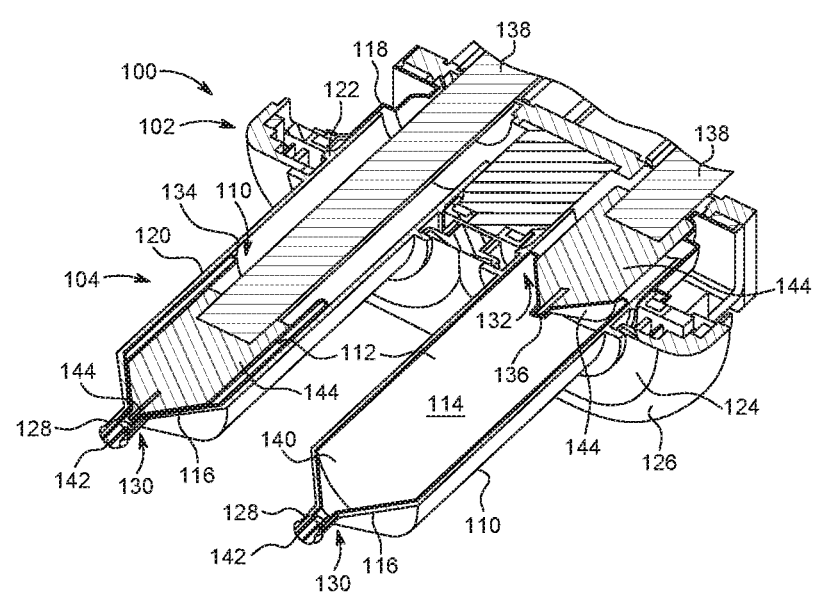
FIG. 2 is a perspective, cross-sectional view of a portion of the fluid injection system shown in FIG. 1.

FIG. 2 is a perspective, cross-sectional view of a portion of the fluid injector 102 shown in FIG. 1. With reference to FIG. 2, the syringe 104 generally includes a cylindrical body or pressure jacket 110 and a rolling diaphragm 112 that interfaces with the pressure jacket 110. As will be described hereinafter, the rolling diaphragm 112 defines an interior volume 114 for receiving a fluid therein. The rolling diaphragm 112 is configured for being inserted into at least a portion of the pressure jacket 110 and the pressure jacket 110 is configured for engagement with fluid injector 102. The syringe 104 is adapted for use in CT, MRI, PET, and like procedures and operable at typical operating pressures of, for example, about 200-400 psi. In some aspects, the rolling diaphragm 112 may be a bladder syringe described in U.S. patent application Ser. No. 13/881,072, entitled "Bladder Syringe Fluid Delivery System", or a syringe described in U.S. patent application Ser. No. 13/834,624, entitled "Bellows Syringe Fluid Delivery System", the disclosures of which are incorporated herein by reference in their entirety.

The cylindrical body of pressure jacket 110 may be a unitary, typically cylindrical body having a distal end 116 and a proximal end 118 with a throughbore T extending between the distal end 116 and the proximal end 118. The pressure jacket 110 is typically a reusable component, while the rolling diaphragm 112 is typically a single-use component. In another aspect, the rolling diaphragm 112 may be reusable such that the rolling diaphragm 112 is refillable with fluid. For example, the rolling diaphragm 112 can be pre-filled with fluid, or can be initially empty, and can be filled and/or refilled one or more times. In another aspect, both the pressure jacket 110 and the rolling diaphragm 112 may be single-use components that are disposed of after each patient use. In this aspect, both the pressure jacket 110 and the rolling diaphragm 112 are disposed of after use and a new pressure jacket 110 and rolling diaphragm 112 are loaded into the fluid injector 102. The pressure jacket 110 has a sidewall 120 that defines a throughbore between the distal and proximal ends 116, 118. The proximal end 118 is adapted to interface with the fluid injector 102 and includes one or more mounting structures 122 positioned to engage a locking mechanism at the front end or face plate 124 of the housing 126 of the fluid injector 102 to properly seat the pressure jacket 110 relative to the fluid injector 102. As an example, two opposed bayonet attachment flanges may be provided on the proximal end 118 for interfacing with the fluid injector face plate 124 to secure the pressure jacket 110 to the fluid injector 102. In some aspects, the pressure jacket 110 may have a connection interface to releasably secure the pressure jacket to the fluid injector 102 in the form of a connection interface described in U.S. patent application Ser. No. 14/526,294, entitled "Self-Orienting Syringe and Syringe Interface", or in U.S. patent application Ser. No. 14/526,395, entitled "Self-Orienting Syringe and Syringe Interface", the disclosures of which are incorporated herein by reference in their entirety. In another aspect, an adapter may be provided for connecting the pressure jacket 110 and rolling diaphragm 112 to the fluid injector 102.

The distal end 116 of the pressure jacket 110 may include a substantially frusto-conical portion that terminates in an outlet port 128. The pressure jacket 110 may be made of any suitable medical grade material, such as a medical grade plastic material, desirably a clear plastic material, such as, but not limited to, polycarbonate, acrylic, or polyester. In some aspects, the pressure jacket 110 may be releasably secured to the fluid injector 102, for example but not limited to, by a retractable pin that extends through an opening of the pressure jacket 110 to prevent rotation of the pressure jacket 110 when it is loaded onto the fluid injector 102. In other aspects, the pressure jacket 110 may have one or more legs that engage the housing of the fluid injector 102 to prevent rotation of the pressure jacket 110 when it is loaded onto the fluid injector 102. In further aspects, a sliding collar may be provided around an outer circumference of the pressure jacket 110. The sliding collar desirably engages an expandable ring to expand the ring against a corresponding locking feature of the fluid injector 102 to lock the pressure jacket 110 with the fluid injector 102.

Figure 3:
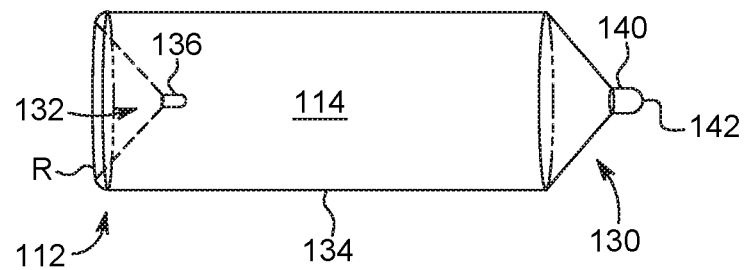
FIG. 3 is a side view of a rolling diaphragm in accordance with one aspect of the present disclosure.

With reference to FIG. 3, and with continuing reference to FIG. 2, the rolling diaphragm 112 generally includes a hollow body that includes a forward or distal end 130, a rearward or proximal end 132, and a flexible sidewall 134 extending therebetween. The proximal end 132 defines a closed end wall 136. The closed end wall 136 may be shaped to interface directly with the piston head 138 and/or the plunger 144 of the fluid injector 102. For example, the closed end wall 136 may define a receiving end pocket for interfacing directly with a similarly-shaped piston head 138 and/or plunger 144. In particular, the piston head 138 and/or plunger 144 may be shaped to match the shape of the closed end wall 136 or pressure from the piston head 138 and/or plunger 144 may conform the end wall 136 to substantially match the shape of the piston head 138 and/or plunger 144. The closed end wall 136 may alternatively include an attached rigid base element for engaging with the piston head 138 or plunger 144 in a like manner. In one aspect, the proximal end 132 and/or the distal end 130 of the rolling diaphragm 112 may be more rigid relative to the sidewall 134. In yet another aspect, the rolling diaphragm 112 may be formed from a plurality of individual layers that are co-formed together into a single, unitary structure. At least one of the layers may peel away from the sidewall 134 as the sidewall 134 is rolled over during an injection procedure. At least one of the layers may be made from a heat-shrinkable material which is activated to shrink at a predetermined temperature. The predetermined temperature may be achieved, for example, during an autoclave process. In this aspect, the heat-shrinkable layer may serve as a pressure jacket. The sidewall 134 may have a smooth, substantially uniform structure, or it may have one or more ribs provided thereon to facilitate the rollover during an injection procedure. One or more indicia (not shown) may be formed on the sidewall 134. In another aspect, the sidewall 134 may have a non-uniform thickness along its longitudinal length to facilitate the rolling over of the sidewall 134. For example, the sidewall 134 at or near the proximal end 132 may be thinner than the sidewall 134 at or near the distal end 130 to facilitate rolling of the sidewall 134 from the proximal end 132 toward the distal end 130. The thicker sidewall 134 at or near the distal end 130 may function as the pressure jacket 110 and may not roll over. In specific embodiments, the sidewall 134 at or near the distal end 130 may be substantially rigid.

The rearward or proximal portion of the sidewall 134 connects to the closed end wall 136, and a forward or distal portion of the sidewall 134 defines a discharge neck 140 opposite the closed end wall 136. The closed end wall 136 may have a non-uniform thickness, for example in a radial direction extending from a central longitudinal axis of the rolling diaphragm 112. In certain embodiments, the end wall 136 may be thicker near the center and thinner near the connection with the sidewall 134. The discharge neck 140 is adapted to be received in the interior portion of the distal end 116 of the pressure jacket 110 such that the discharge neck 140 is aligned with the outlet port 128 of the pressure jacket 110. The distal end 130 of the rolling diaphragm 112 may be secured permanently within the interior of the pressure jacket 110, adhesively secured therein, or be removably secured therein such as by a friction fit connection or other suitable mechanical connection, such as by securing at the distal end of the pressure jacket 110. The discharge neck 140 terminates in a discharge port 142 that may have, according to one non-limiting aspect, a fracturable seal (discussed herein) for sterility purposes, such as piercable foil or an elastomeric seal.

Figure 4A:
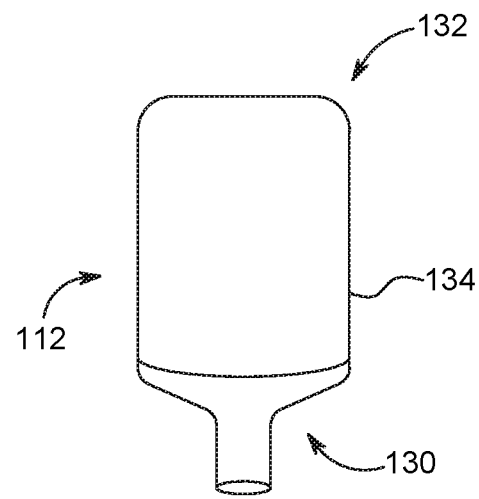
FIG. 4A is a side view a rolling diaphragm in accordance with another aspect of the present disclosure, with the rolling diaphragm shown in an uncompressed state.
Figure 4B:
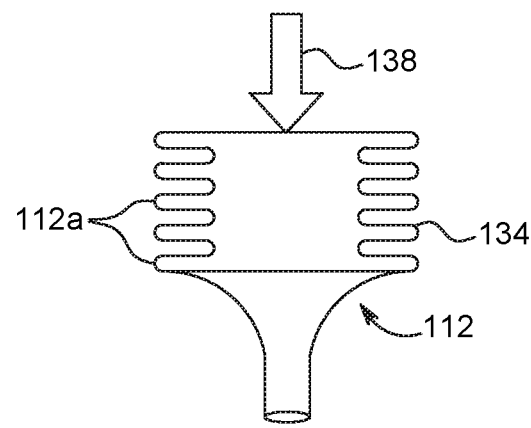
FIG. 4B is a side view the rolling diaphragm shown in FIG. 4A in a compressed state.

The sidewall 134 of the rolling diaphragm 112 defines a soft, pliable or flexible, yet self-supporting body that is configured to roll upon itself under the action of the piston head 138 and/or plunger 144. In particular, as shown in FIG. 2, the sidewall 134 of the rolling diaphragm 112 is configured to roll such that its outer surface is folded and inverted in a radially inward direction as piston 138 and/or plunger 144 are moved in a distal direction and unroll and unfold in the opposite manner in a radially outward direction as piston 138 and/or plunger 144 are retracted in a proximal direction. With reference to FIG. 3, the closed end wall 136 may have a concave shape to facilitate the initiation of the inversion or rolling of the sidewall 134. In another aspect, sidewall 134 of the rolling diaphragm 112 may be configured to be crushed under the action of the piston head 138 from a first, uncompressed state, as shown in FIG. 4A, to a second, compressed state, as shown in FIG. 4B, by folding over in a plurality of axial folds 112a. One or more of the axial folds 112a may be pre-formed at predetermined axial positions of the sidewall 134 of the rolling diaphragm 112.

The rolling diaphragm 112 may be made of any suitable plastic material, desirably a clear plastic material, such as, but not limited to, polyproplylene random copolymer, polyproplylene impact copolymer, polyproplylene homopolymer, polypropylene, polyethylene terephthalate, POM, ABS, HPDE, nylon, cyclic olefin copolymer, multilayer polypropylene, polycarbonate, ethylene vinyl acetate, polyethylene, and the like. The material of the rolling diaphragm 112 is desirably selected to meet the required tensile and planar stress requirements, water vapor transmission, and chemical/biological compatibility. In some aspects, the rolling diaphragm 112 may have at least one electro-active polymer layer that expands or contracts in response to an application of an electrical voltage. The electro-active polymer layer may be activated to expand or contract the sidewall 134 of the rolling diaphragm 112 to disengage or engage the plunger 144. In some aspects, the electro-active polymer layer may be made from a NAFION™ or FLEMION™ materials. In various embodiments, the clear plastic material may withstand sterilization procedures, such as exposure to ethylene oxide or electromagnetic radiation sterilization procedures.

The rolling diaphragm 112 according to various embodiments herein may be made by a blowing-filling-capping (BFC) technique, also referred to in the relevant field of endeavor as a blow-mold-seal (BFS) technique, wherein the rolling diaphragm 112 is blow-molded, filled with the desired medical fluid, such as saline or contrast media, and aseptically sealed by sealing the discharge port 142 with an integrally formed/molded rupture-ready seal, as will be described hereinafter. The BFC technique permits the rolling diaphragm 112 to be formed, filled, and sealed typically in one machine or apparatus. These steps may be accomplished under sterility maintained conditions, limiting the possibility of introducing contaminates in the formed, filled, and sealed rolling diaphragm 112. The entire assembly may be autoclaved or otherwise treated for sterilization. The rupture-ready seal is formed as part of the molding process at the conclusion of the filling of the rolling diaphragm 112. A sterility-enhanced preformed and prefilled rolling diaphragm 112 results from the BFC process. The rupture-ready seal may be designed for external removal or puncture by a user, or may be designed to reliably burst when a preset internal pressure is reached in the rolling diaphragm 112 as the piston head 138 moves distally or forward in the rolling diaphragm 112. In another aspect, the rolling diaphragm 112 may be ruptured by a piercing element provided on the pressure jacket 110. In another aspect, the rolling diaphragm 112 may be encased in a protective cover (not shown) to increase its rigidity and prevent contamination. The protective cover may or may not be removed from the rolling diaphragm 112 prior to installation on the injector 102. The rolling diaphragm 112 may be formed to have a variety of shapes. For example, the rolling diaphragm 112 may be cylindrical, conical, spherical, ellipsoidal, egg-shaped, etc. Furthermore, the rolling diaphragm 112 may have different width to length ratios. For example, the rolling diaphragm 112 may be formed to have a diameter that is substantially smaller or larger compared to its longitudinal length. One of ordinary skill in the art will understand that the injector 102 may be desirably programmed to control the movement of the plunger 144 in order to deliver a substantially constant and predictable flow rate of fluid from the rolling diaphragm 112.

The outer diameter of the rolling diaphragm 112 may be dimensioned such that the rolling diaphragm 112 fits within the interior space defined by the throughbore and inner surface of the pressure jacket 110. In one aspect, the rolling diaphragm 112 fits snuggly within the pressure jacket 110 such that the outer surface of the rolling diaphragm 112 abuts the inner surface of the walls of the pressure jacket 110. In another aspect, the rolling diaphragm 112 fits loosely within the pressure jacket 110 such that there is a gap between at least a portion of the outer surface of the rolling diaphragm 112 and the inner surface of the pressure jacket 110. The rolling diaphragm 112 may be expanded under pressure during an injection procedure such that the outer surface of the rolling diaphragm 112 abuts the inner surface of the pressure jacket 110.

Figure 5A:
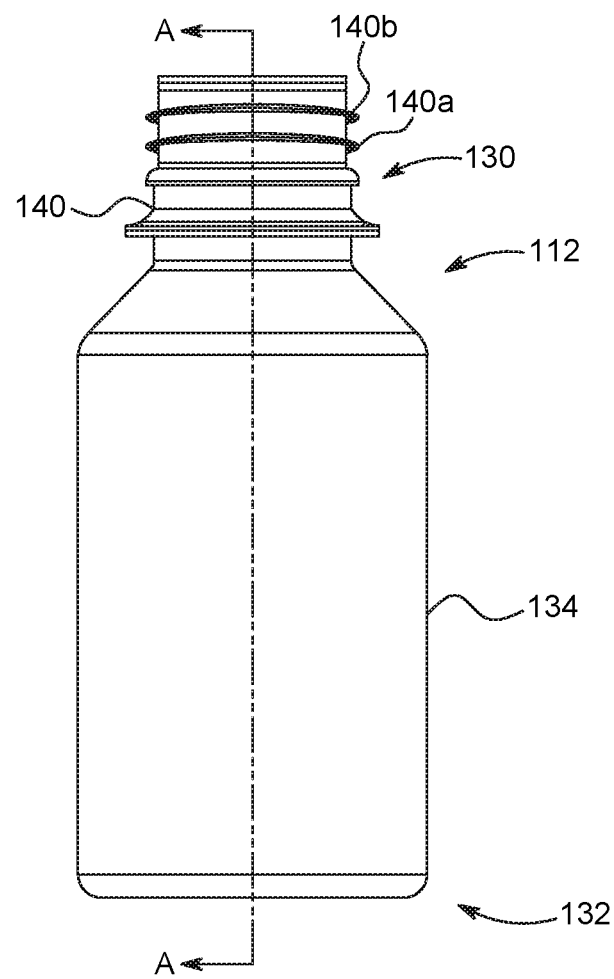
FIG. 5A is a side view a rolling diaphragm in accordance with another aspect of the present disclosure.
Figure 5B:
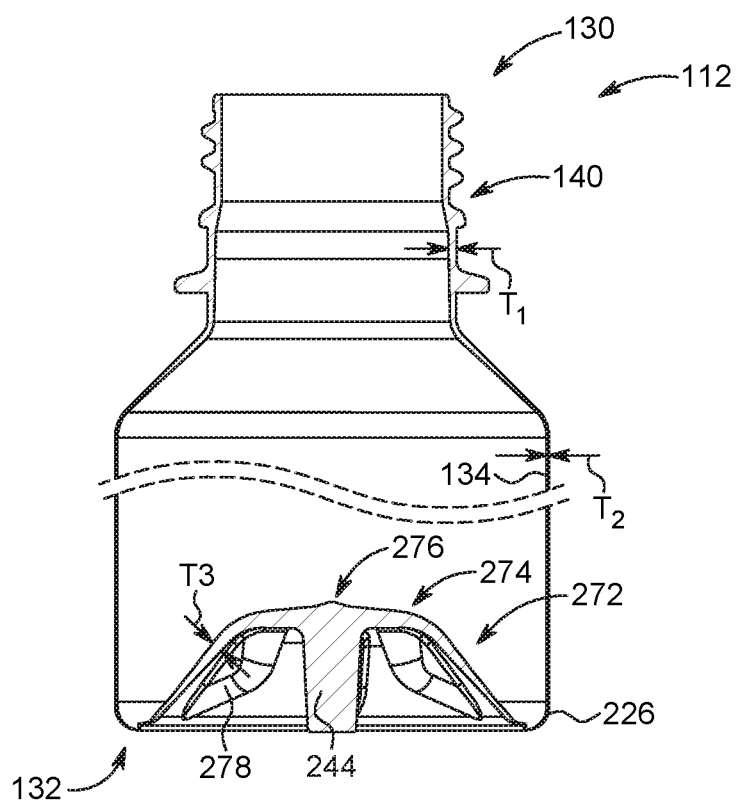
FIG. 5B is a cross-sectional side view the rolling diaphragm shown in FIG. 5A taken along line A-A.

FIGS. 5A-5B show a rolling diaphragm 112 in accordance with another aspect of the present disclosure. FIG. 5B is a cross-sectional side view the rolling diaphragm shown in FIG. 5A taken along line A-A. The components of rolling diaphragm 112 shown in FIGS. 5A-5B are substantially similar to the components of the rolling diaphragm 112 described herein with reference to FIGS. 2-3. Reference numerals in FIGS. 5A-5B are used to illustrate identical components as the corresponding reference numerals in FIGS. 2-3. As the previous discussion regarding the rolling diaphragm 112 generally shown in FIGS. 2-3 is applicable to the aspect shown in FIGS. 5A-5B, only the relevant differences between these systems are discussed hereinafter.

Referring initially to FIG. 5A, the distal end 130 of the rolling diaphragm 112 has an open-ended discharge neck 140 having a connection interface 140a for connecting to a corresponding connection interface which may connect to a fluid path set (not shown). In some aspects, the connection interface 140a is a threaded interface having one or more threads 140b for mating with corresponding threads on the connection interface to the fluid path set. In certain aspects the connection interface to the fluid path may have a connection configured to connect to the fluid path, such as a luer connection.

With reference to FIG. 5B, the discharge neck 140 has a first sidewall thickness $T_1$ that is larger than a thickness $T_2$ of the sidewall 134. Thickness $T_1$ is selected such that the discharge neck 140 may be sufficiently rigid to allow for connecting to a corresponding connection interface of a fluid path set (not shown) without substantially deforming the discharge neck 140. Thickness $T_2$ is selected such that the sidewall 134 of the rolling diaphragm 112 is flexible to allow for rolling over and unrolling of the sidewall 134 as described herein. The proximal end 132 of the rolling diaphragm 112, such as the closed end wall 136, may be reinforced to prevent deformation during rolling over of the sidewall 134. In some aspects, the proximal end 132 of the rolling diaphragm 112 is configured for engagement with the plunger 144 (not shown). The proximal end 132 has a radiused folding edge 226 having a flexible sidewall to initiate the rolling over and in certain embodiments, unrolling of the sidewall 134 of the rolling diaphragm 112. In this embodiment, the folding edge 226 may transition into a distally-extending ramp 272 having continuously increasing sidewall thickness $T_3$ to a distal portion 274 of the end wall 136. The distal portion 274 may have a radiused central portion 276 extending distally from an upper surface of the distal portion 274 and a plunger engagement portion 244 extending proximally from a lower surface of the distal portion 274. The plunger engagement portion 244 is configured for engagement with the plunger 144 (not shown), as described herein. The proximal end 132 of the rolling diaphragm 112 may have one or more ribs 278 protruding radially outward from the plunger engagement portion 244 along a lower surface of the ramp 272.

Figure 6:
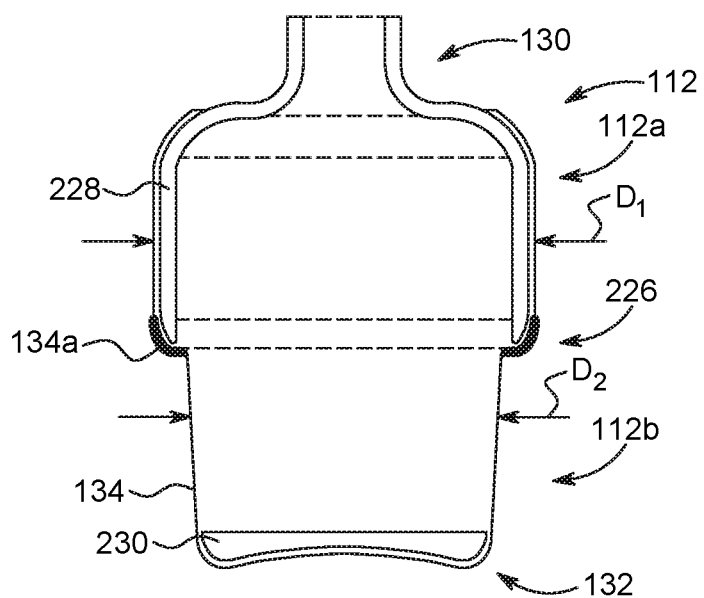
FIG. 6 is a cross-sectional side view of a rolling diaphragm in accordance with another aspect of the present disclosure.
Figure 40:
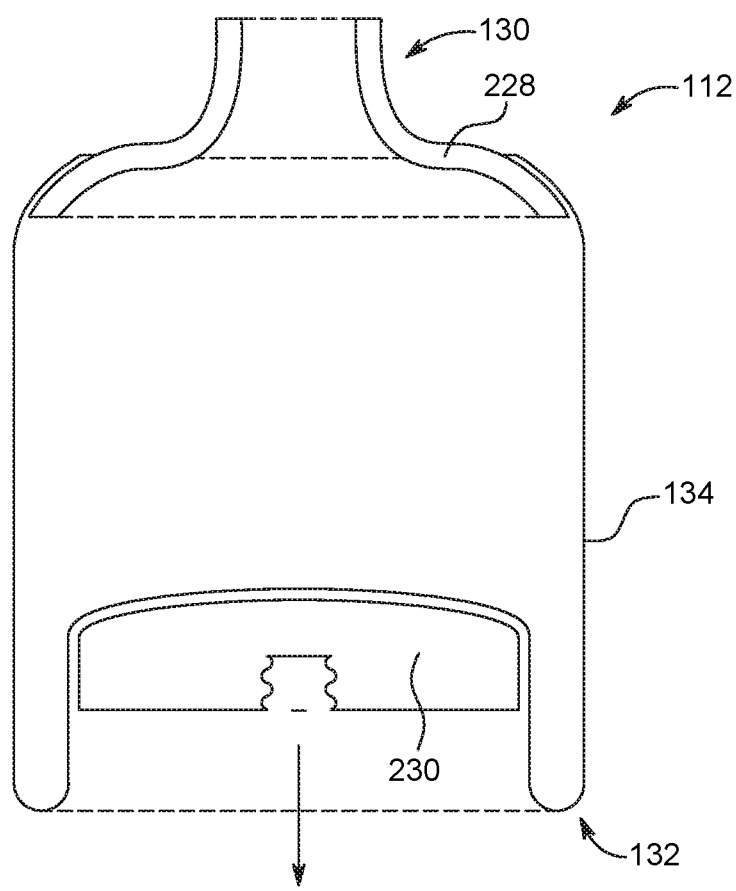
FIG. 40 is a cross-sectional side view of a rolling diaphragm and plunger in accordance with another aspect of the present disclosure.

FIG. 6 is a cross-sectional side view of a rolling diaphragm 112 in accordance with another aspect of the present disclosure. A first portion 112a of the rolling diaphragm 112 has a first diameter $D_1$ and a second portion 112b of the rolling diaphragm 112 has a second diameter $D_2$ that is different from the first diameter $D_1$. In some aspects, the first portion 112a may be an forward portion of the rolling diaphragm 112 extending from the distal end 130 to an approximate midpoint of the rolling diaphragm 112, while the second portion 112b may be a rearward portion of the rolling diaphragm 112 extending the approximate midpoint of the rolling diaphragm 112 to the proximal end 132. The first diameter $D_1$ may be larger than the second diameter $D_2$ to allow the second portion 112b to nest inside the first portion 112a as the second portion 112b is inverted about a folding edge 226. Nesting of the second portion 112b within the first portion 112a minimizes hoop compression at the folding edge 226. The folding edge 226 may have a thickened sidewall 134a compared to the sidewall 134 of the first and second portions 112a, 112b of the rolling diaphragm 112. In some aspects, the first portion 112a may have a collar 228 surrounding or surrounded by the sidewall 134, while the second portion 112b may have a plunger support base 230 for reinforcing engagement with the plunger 144 (not shown). FIG. 40 shows a rolling diaphragm 112 with the plunger support base 230 and the collar 228 without the sidewall 134 having the varying diameter shown in FIG. 6.

Figure 7:
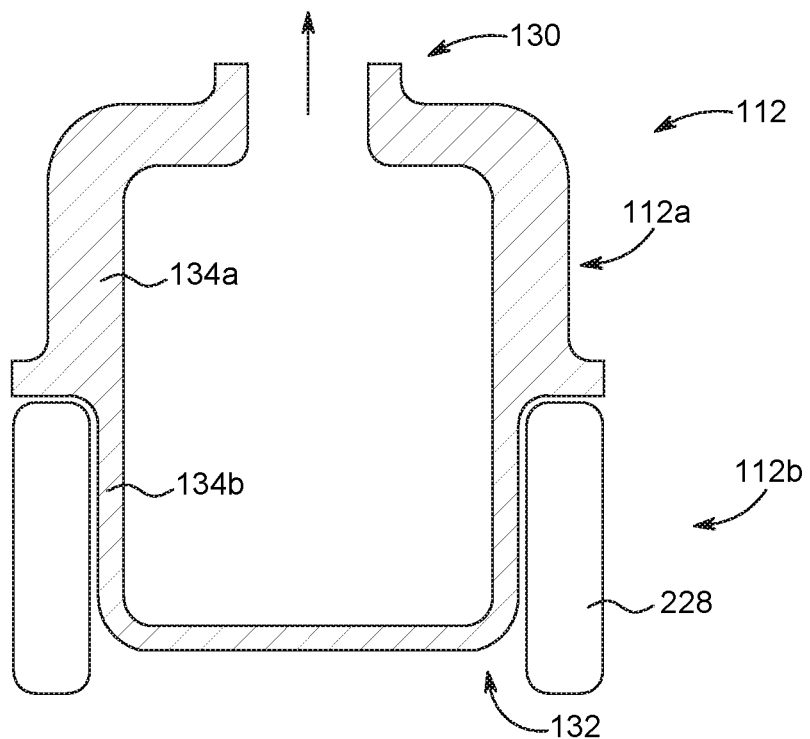
FIG. 7 is a cross-sectional side view of a rolling diaphragm in accordance with another aspect of the present disclosure.

FIG. 7 is a cross-sectional side view of a rolling diaphragm 112 in accordance with another aspect of the present disclosure. A first portion 112a of the rolling diaphragm 112 has a first sidewall 134a and a second portion 112b of the rolling diaphragm 112 has a second sidewall 134b that has a different thickness from the first sidewall 134a. An inner diameter of the rolling diameter 112 may be constant between the first portion 134a and the second portion 134b. In some aspects, the first portion 112a may be an forward portion of the rolling diaphragm 112 extending from the distal end 130 to an approximate midpoint of the rolling diaphragm 112, while the second portion 112b may be a rearward portion of the rolling diaphragm 112 extending the approximate midpoint of the rolling diaphragm 112 to the proximal end 132. The first sidewall 134a may be thicker than the second sidewall 134b such that the first portion 112a of the rolling diaphragm 112 is more rigid relative to the second portion 112b of the rolling diaphragm 112. The second portion 112b nests inside the first portion 112a as the second portion 112b is inverted about a folding edge 226. An exterior portion of the second sidewall 134b may be supported circumferentially by a collar 228. In some aspects, the first and second portions 134a, 134b may have a substantially identical wall thickness, while an approximate midpoint between the first portion 134a and the second portion 134b has a portion with a thinner sidewall thickness relative to the sidewall of the first and second portions 134a, 134b to define a folding edge or an inversion front and prevent buckling of the sidewall as the second portion 134b is inverted upon itself.

Figure 8A:
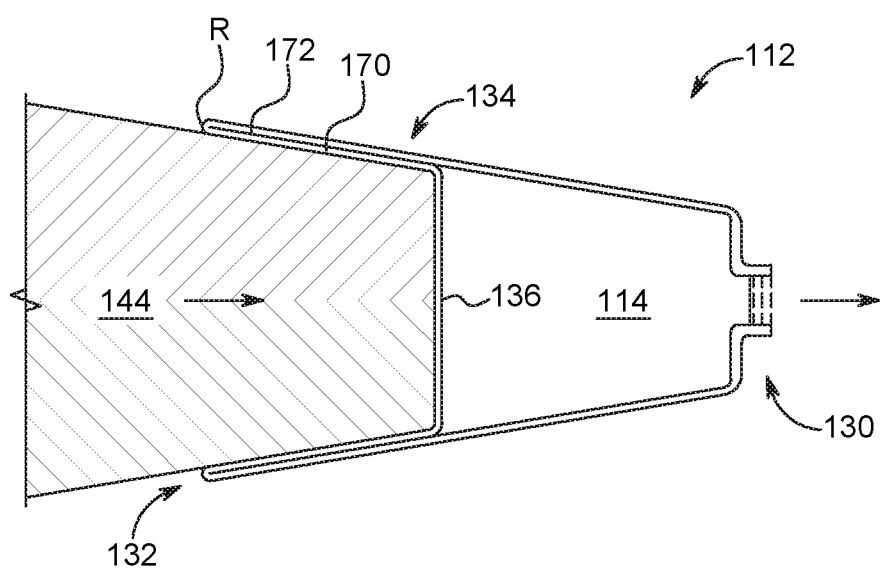
FIG. 8A is a cross-sectional side view of a rolling diaphragm and plunger in accordance with another aspect of the present disclosure where the plunger is shown in a first position.
Figure 8B:
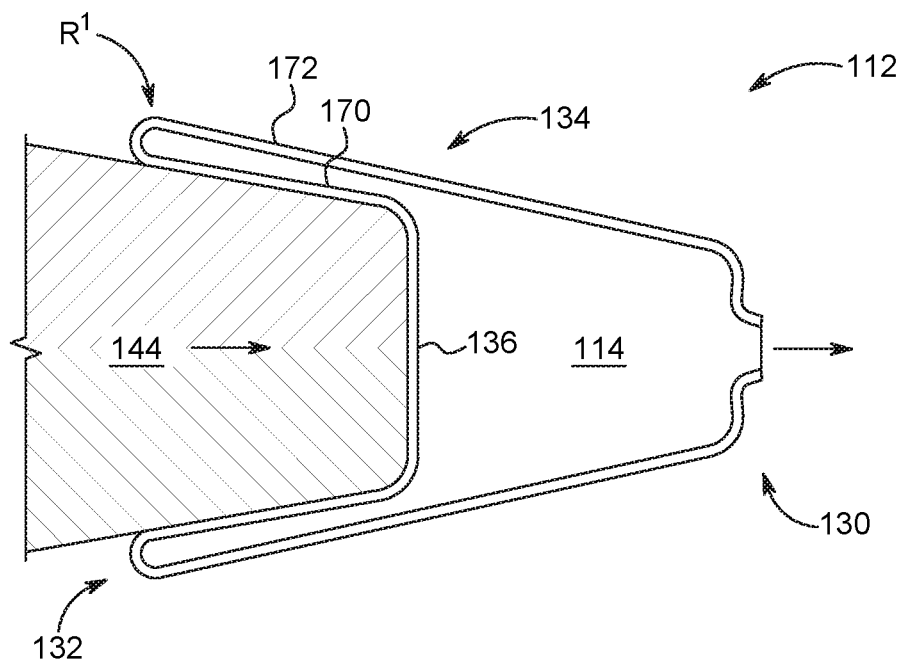
FIG. 8B is a cross-sectional side view of the rolling diaphragm and plunger shown in FIG. 8A where the plunger is shown in a second position.

FIG. 8A is a cross-sectional side view of a rolling diaphragm 112 and plunger 144 in accordance with another aspect of the present disclosure where the plunger 144 is shown in a first position. FIG. 8B is a cross-sectional side view of the rolling diaphragm 112 and plunger 144 shown in FIG. 8A where the plunger 144 is shown in a second position. In some aspects, the sidewall 134 of the rolling diaphragm 112 is tapered such that it narrows and the diameter decreases from the proximal end 132 toward the distal end 130 to correspond substantially to a tapered shape of the plunger 144. The sidewall 134 may be folded such that there is contact between a folded portion 170 and an unfolded portion 172 of the sidewall 134 to minimize residual volume after the plunger 144 is advanced to its maximum distal position. The radius R at which the sidewall 134 is rolled over is desirably minimized to reduce localized stress at the folded portion. With reference to FIG. 8B, in another aspect the sidewall 134 may be folded such that there is no contact between a folded portion 170 and an unfolded portion 172 of the sidewall 134 as the plunger 144 is advanced to its maximum distal position. In this aspect, the radius R' is larger than the radius R in FIG. 8A.

Figure 9A:
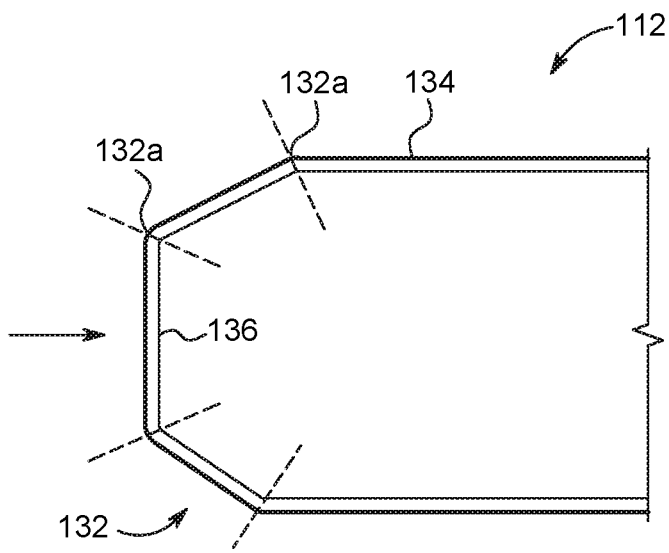
FIG. 9A is a partial cross-sectional side view of a rolling diaphragm in accordance with another aspect of the present disclosure where the rolling diaphragm is shown in a first state.
Figure 9B:
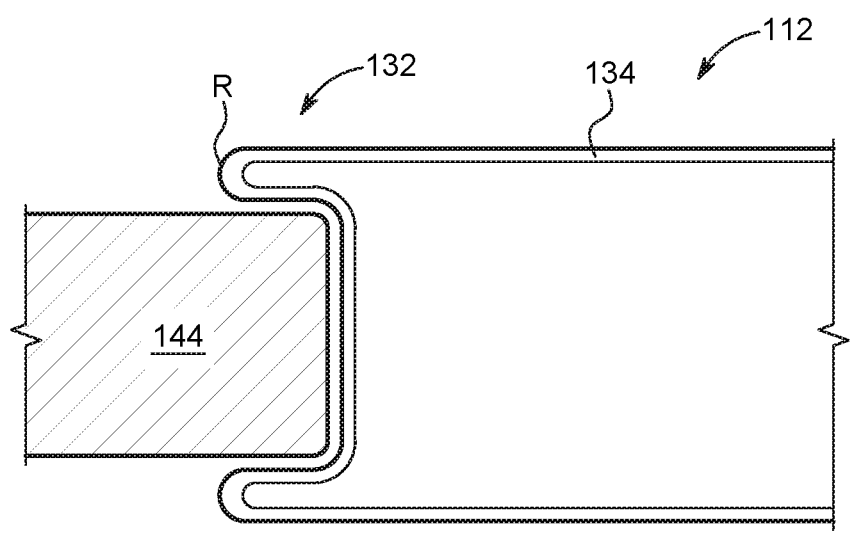
FIG. 9B is a partial cross-sectional side view of the rolling diaphragm shown in FIG. 9A with the rolling diaphragm shown in a second state after engagement with a plunger.

FIG. 9A is a partial cross-sectional side view of a rolling diaphragm 112 in accordance with another aspect of the present disclosure where the rolling diaphragm 112 is shown in a first state. FIG. 9B is a partial cross-sectional side view of the rolling diaphragm 112 shown in FIG. 9A with the rolling diaphragm 112 shown in a second state after engagement with a plunger 144. The proximal end 132 of the rolling diaphragm 112 may be initially formed in a convex shape, such that a portion of the proximal end 132 extends convexly outwardly in a proximal direction. When the plunger 144 engages the proximal end 132, such as shown in FIG. 9B, the convex shape of the proximal end 132 is inverted toward the distal end 146 such that the proximal end 132 is substantially concave as the plunger 144 is advanced in the distal direction. The proximal end 132 may have a pre-formed rolling radius R that facilitates rollover of the rolling diaphragm 112 once it is engaged by the plunger 144. In some aspects, the proximal end 132 may have one or more pre-defined folding portions 132a that facilitate an inversion of the proximal end 132 from the initial convex shape to a concave shape upon engagement with the plunger 144. The folding portions 132a may have thinner sidewalls relative to a thickness of the sidewall 134 of the rolling diaphragm 112.

Figure 10A:
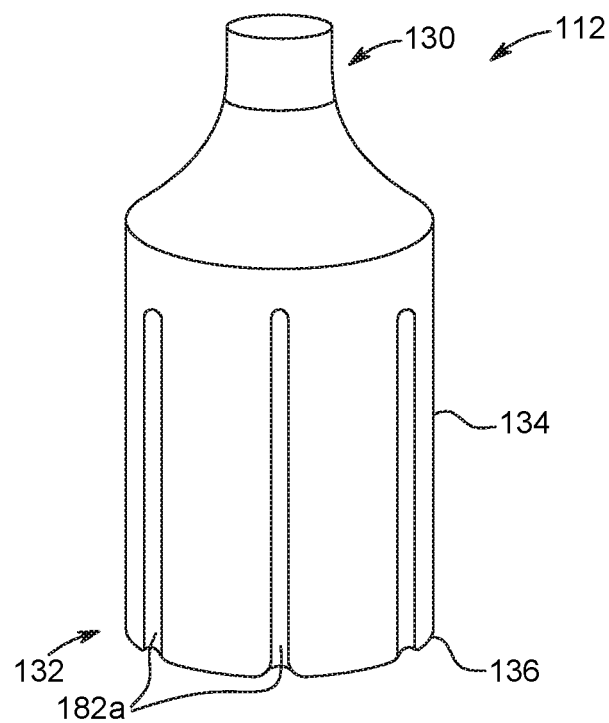
FIG. 10A is a side view of a rolling diaphragm in accordance with another aspect of the present disclosure.

FIG. 10A is a side view of a rolling diaphragm 112 in accordance with another aspect of the present disclosure. The rolling diaphragm 112 has one or more recessed elements 182a that are formed to extend in a radially inward direction. In some aspects, the one or more recessed elements 182a may be formed such that the sidewall 134 has a substantially uniform thickness over at least a portion of an area where the one or more recessed elements 182a is formed. In other aspects, the one or more recessed elements 182a may be formed such that the sidewall 134 has a thinner or thicker sidewall thickness at the location where the one or more recessed elements 182a is formed. The one or more recessed elements 182a may be spaced apart equally or unequally around an outer circumference of the rolling diaphragm 112 to facilitate rollover of the sidewall 134. The plunger 144 (not shown) may be configured to engage one or more of the plurality of recessed elements 182a as the plunger 144 is advanced in a distal direction. In some aspects, the plunger 144 may be shaped to correspond to a shape of the rolling diaphragm 112 having one or more recessed elements 182a.

Figure 10B:
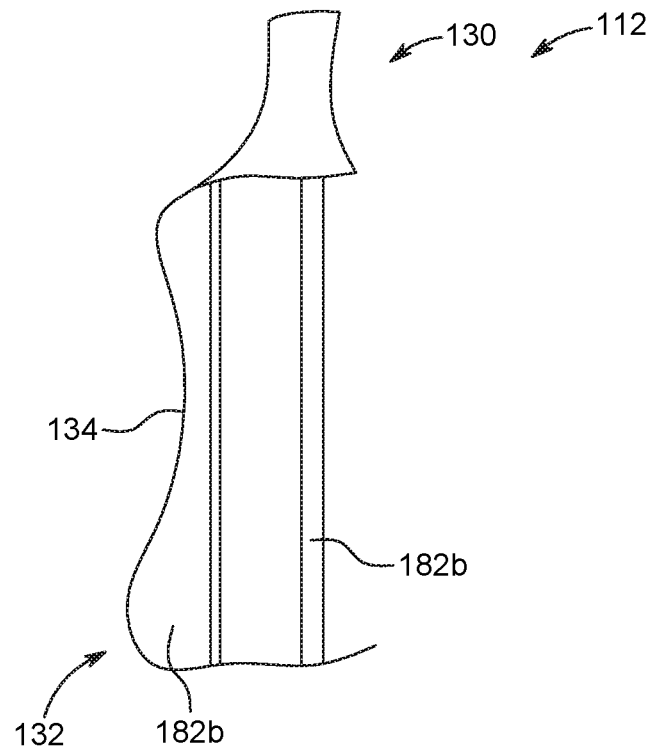
FIG. 10B is a partial side view of a rolling diaphragm in accordance with another aspect of the present disclosure.

FIG. 10B is a partial side view of a rolling diaphragm in accordance with another aspect of the present disclosure. The rolling diaphragm 112 has one or more ribs 182b that are formed to extend in a radially outward direction. In some aspects, the one or more ribs 182b may be formed such that the sidewall 134 has a substantially uniform thickness over at least a portion of an area where the one or more ribs 182b is formed. In other aspects, the one or more ribs 182b may be formed such that the sidewall 134 has a thinner or thicker sidewall thickness at the location where the one or more ribs 182b is formed. The one or more ribs 182b may be shaped such that a first portion of the one or more ribs 182b extends radially outward further compared to a second portion of the ribs 182b. For example, the one or more ribs 182b may be shaped such that the ribs 182b extend radially outward further at or near the proximal and distal ends compared to a central portion of the one or more ribs 182b. The one or more ribs 182b may be spaced apart equally or unequally around an outer circumference of the rolling diaphragm 112 to facilitate rollover of the sidewall 134. The plunger 144 (not shown) may be configured to engage one or more of the plurality of ribs 182b as the plunger 144 is advanced in a distal direction. In some aspects, the plunger 144 may be shaped to correspond to a shape of the rolling diaphragm 112 having one or more ribs 182b.

Figure 11A:
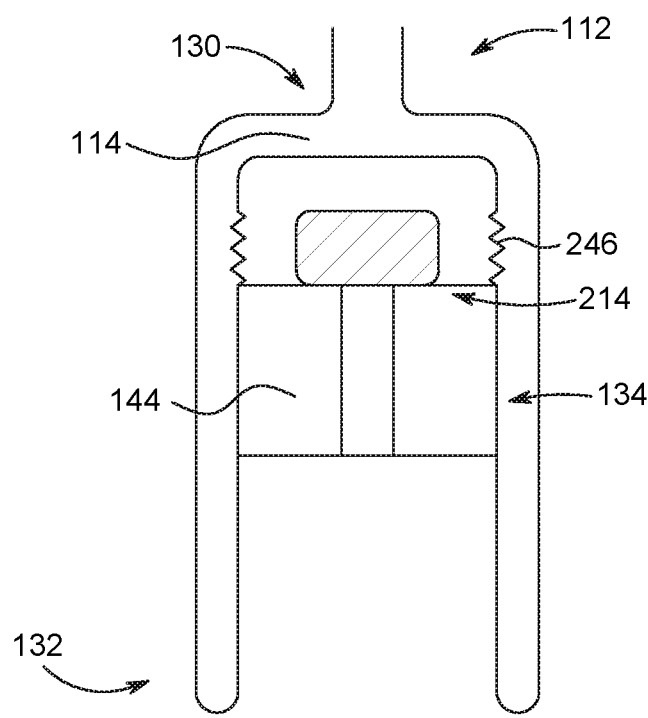
FIG. 11A is a cross-sectional side view of a rolling diaphragm and plunger in accordance with another aspect of the present disclosure, with the plunger shown in a first state.
Figure 11B:
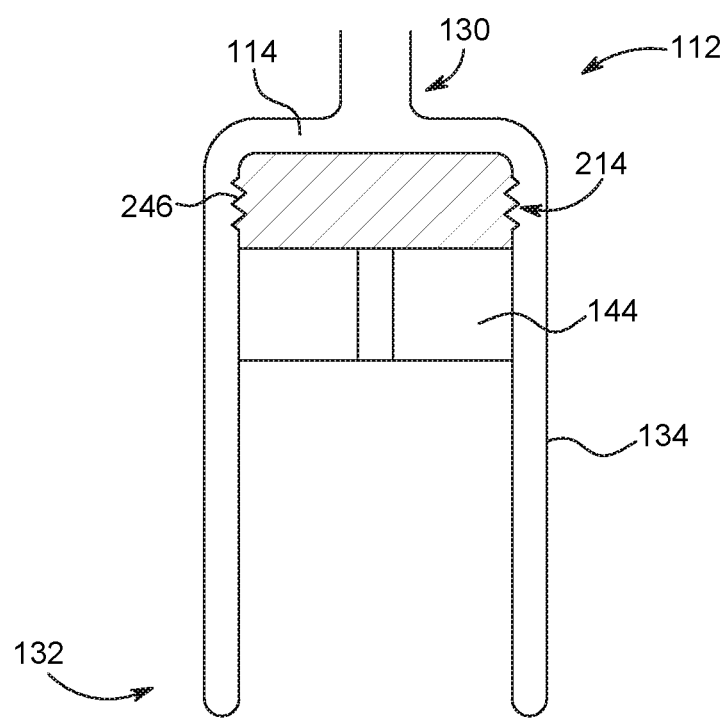
FIG. 11B is a cross-sectional side view of the rolling diaphragm and plunger shown in FIG. 11A, with the plunger shown in a second state.

FIG. 11A is a cross-sectional side view of a rolling diaphragm 112 and plunger 144 in accordance with another aspect of the present disclosure, with the plunger 144 shown in a first state. FIG. 11B is a cross-sectional side view of the rolling diaphragm 112 and plunger 144 shown in FIG. 11A, with the plunger 144 shown in a second state. The rolling diaphragm 112 may be initially formed such that the proximal end wall 136 is inverted inwardly toward the distal end 130 such that internal volume 114 of the rolling diaphragm 112 is empty of fluid. In order to withdraw the proximal end wall 136 of the rolling diaphragm 112 in the proximal direction and fill the interior volume of the rolling diaphragm 112 with fluid, the plunger 144 engages at least a portion of the proximal end wall 136 to "grab" the proximal end wall 136 before withdrawing in the proximal direction. In some aspects, an external diameter of the plunger 144 may be slightly smaller than an internal diameter of the rolling diaphragm 112 in an inverted state shown in FIG. 11A. In order to facilitate connection of the proximal end wall 136 of the rolling diaphragm 112 with the plunger 144, an expandable material 214, such as expandable foam, may be provided. The expandable material 214 may be in an unexpanded state prior to engagement of the plunger 144 with the proximal end wall 136 of the rolling diaphragm 112. For example, the expandable material 214 may be contained in a container that is pierced by the plunger 144 as the plunger 144 is advanced toward the proximal end wall 136 of the rolling diaphragm 112. The expandable material 214 may be expandable when exposed to air such that the expandable material 214 expands and engages the sidewall 134 of the rolling diaphragm 112 at the proximal end wall 136 and the plunger 144. The expandable material 214 may harden after a predetermined amount of time to permanently or releasably connect the plunger 144 to the proximal end wall 136 of the rolling diaphragm 112 and allow the rolling diaphragm 112 to be withdrawn in the proximal direction due to movement of the plunger 144. One or more gripping elements 246 may be provided on a folded portion of the sidewall 134 and/or on at least a portion of the outer circumference of the distal portion of the plunger 144 to provide an engagement between the surface for the expandable material 214 and the proximal end wall 136 and/or the inwardly facing outer wall proximate the proximal end wall 136.

Figure 12A:
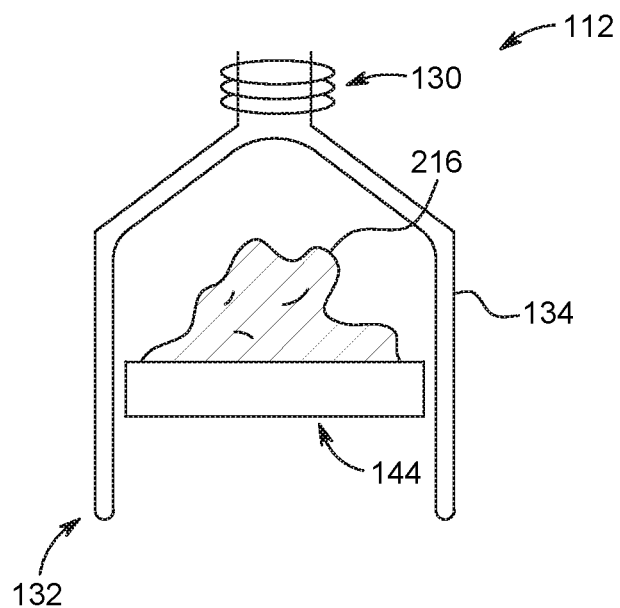
FIG. 12A is a cross-sectional side view of a rolling diaphragm and plunger in accordance with another aspect of the present disclosure, with the plunger shown in a first state.
Figure 12B:
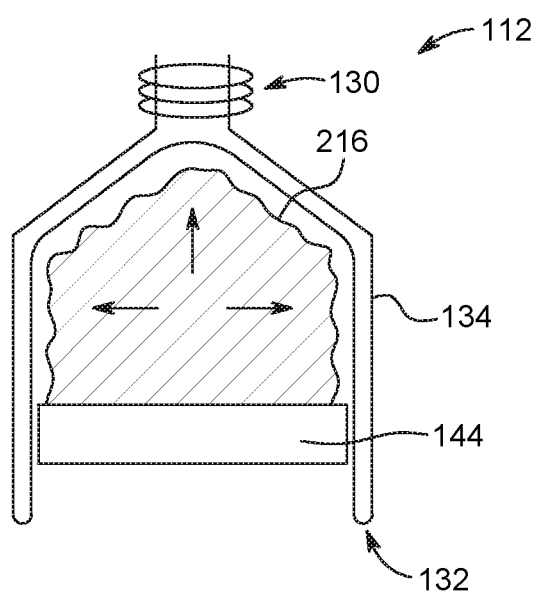
FIG. 12B is a cross-sectional side view of the rolling diaphragm and plunger shown in FIG. 12A, with the plunger shown in a second state.

FIG. 12A is a cross-sectional side view of a rolling diaphragm 112 and plunger 144 in accordance with another aspect of the present disclosure, with the plunger 144 shown in a first state. FIG. 12B is a cross-sectional side view of the rolling diaphragm 112 and plunger 144 shown in FIG. 12A, with the plunger 144 shown in a second state. The rolling diaphragm 112 may be initially formed such that the proximal end wall 136 is inverted inwardly toward the distal end 130 such that an interior volume of the rolling diaphragm 112 is empty of fluid. In order to withdraw the proximal end wall 136 of the rolling diaphragm 112 in the proximal direction and fill the interior volume of the rolling diaphragm 112 with fluid, the plunger 144 engages at least a portion of the proximal end wall 136 to "grab" the proximal end wall 136 before withdrawing in the proximal direction. In some aspects, an external diameter of the plunger 144 may be slightly smaller than an internal diameter of the rolling diaphragm 112 in an inverted state shown in FIG. 12A. In order to facilitate connection of the proximal end wall 136 of the rolling diaphragm 112 with the plunger 144, a distal portion of the plunger 144 may have an expandable balloon 216. The balloon 216 may be expanded from a deflated state, such as shown in FIG. 12A, to an inflated state, such as shown in FIG. 12B, by introducing an operating fluid, such as fluid or pressurized gas, into an interior of the balloon 216. Expansion of the balloon 216 from the deflated state to an inflated state causes the balloon 216 to engage the sidewall 134 of the rolling diaphragm 112 at the proximal end wall 136. The rolling diaphragm 112 may then be withdrawn in the proximal direction when urged by the plunger 144.

Figure 13A:
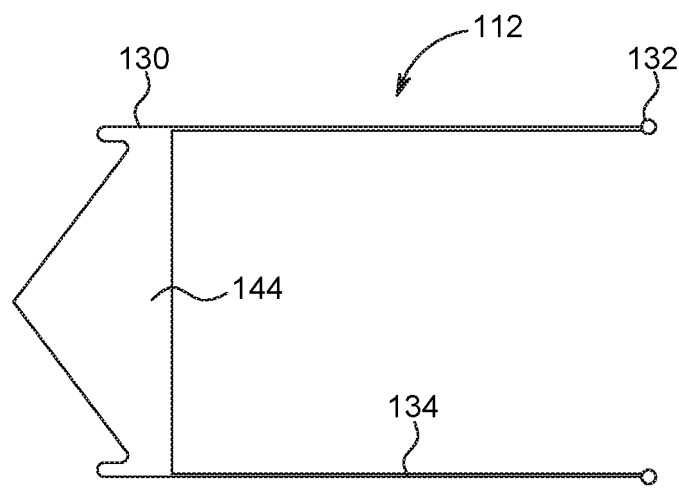
FIG. 13A is a cross-sectional side view of a rolling diaphragm in accordance with another aspect of the present disclosure.
Figure 13B:
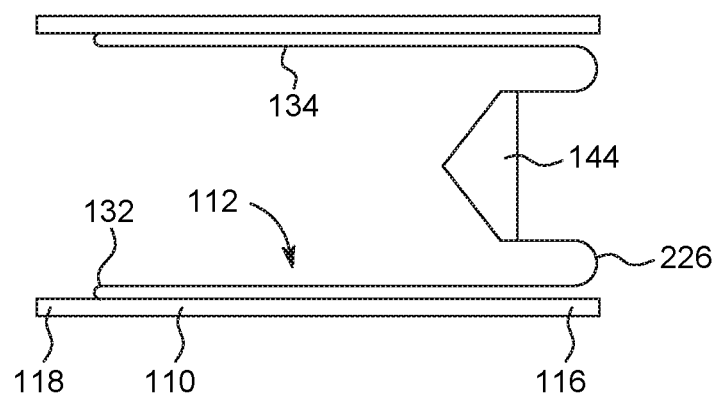
FIG. 13B is a cross-sectional side view of the rolling diaphragm shown in FIG. 12A, where the rolling diaphragm is engaged by a plunger.

FIG. 13A is a cross-sectional side view of a rolling diaphragm 112 in accordance with another aspect of the present disclosure. FIG. 13B is a cross-sectional side view of the rolling diaphragm 112 shown in FIG. 13A, where the rolling diaphragm 112 is engaged by a plunger 144. In some aspects, the proximal end 132 of the rolling diaphragm 112 may be connected to the distal end 116, rather than the proximal end 118, of the pressure jacket 110, such that the rolling diaphragm 112 is inverted relative to the rolling diaphragm 112 shown in FIG. 2. In particular, the sidewall 134 of the rolling diaphragm 112 is initially inverted into the interior of the pressure jacket 110 such that the distal end 130 of the rolling diaphragm 112 is positioned toward the proximal end 118 of the pressure jacket 110. The plunger 144 is provided at the distal end 130 of the rolling diaphragm 112. With reference to FIG. 13B, the rolling diaphragm 112 may be co-molded with the plunger 144. After co-molding, the rolling diaphragm 112 may be expanded to its final form by a blow molding technique. For example, the rolling diaphragm 112 may be expanded by a stretch blow molding technique. Alternatively, the rolling diaphragm 112 may be molded to its final, expanded shape and the plunger 144 may be co-molded with the rolling diaphragm 112.

Figure 14A:
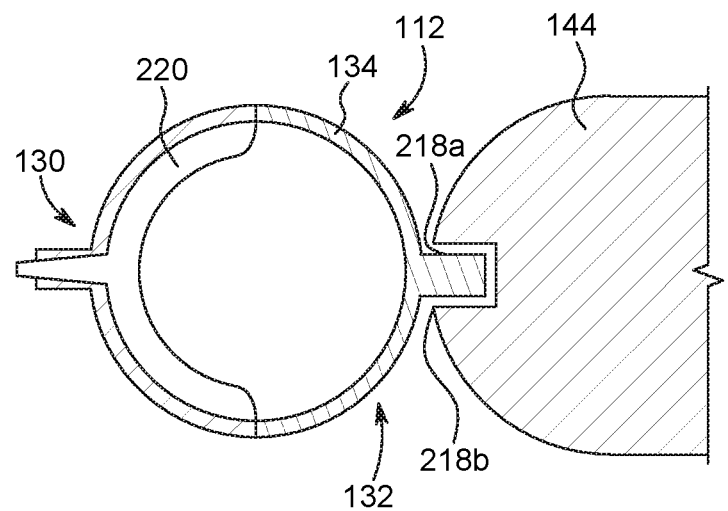
FIG. 14A is a cross-sectional side view of a rolling diaphragm and plunger in accordance with another aspect of the present disclosure.

FIG. 14A is a cross-sectional side view of a rolling diaphragm 112 and plunger 144 in accordance with another aspect of the present disclosure. The rolling diaphragm 112 has a substantially spherical shape. The proximal end 132 of the rolling diaphragm 112 may have an engagement member 218a for engagement with a corresponding engagement member 218b formed on the plunger 144. The proximal end 132 is inverted from a first convex configuration to a second concave configuration upon engagement with the plunger 144. The distal end 130 of the rolling diaphragm 112 may have a support element 220 for engaging the plunger 144 at the end of the stroke of the plunger 144 in the distal direction. The support element 220 may be provided inside an interior volume of the rolling diaphragm 112. Alternatively, the support element 220 may engage an exterior sidewall at the distal end 130 of the rolling diaphragm 112. The plunger 144 is desirably shaped to expel substantially all fluid from the interior volume of the rolling diaphragm 112.

Figure 14B:
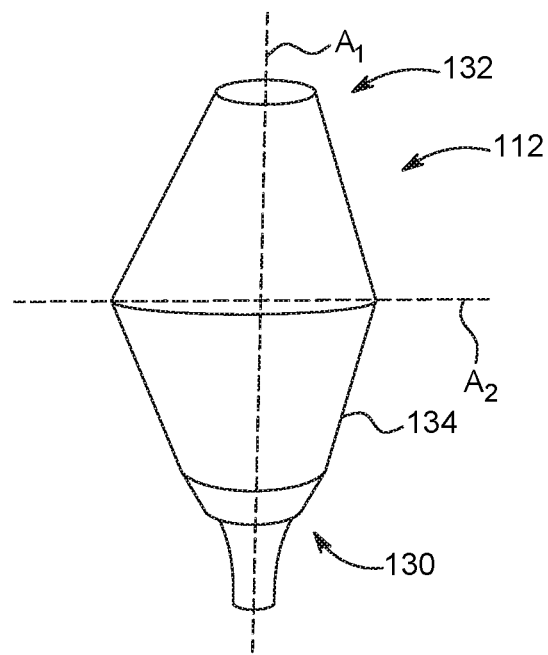
FIG. 14B is a cross-sectional side view of a rolling diaphragm in accordance with another aspect of the present disclosure.

FIG. 14B is a cross-sectional side view of a rolling diaphragm in accordance with another aspect of the present disclosure. Similar to the substantially spherical shape of the rolling diaphragm 112 shown in FIG. 14A, the rolling diaphragm 112 in FIG. 14B has a substantially ellipsoid shape. The rolling diaphragm 112 has an elliptical cross-section having a major axis $A_1$ extending along the longitudinal direction of the rolling diaphragm 112 and a minor axis $A_2$ extending perpendicular to the longitudinal direction, where the major axis $A_1$ is longer than the minor axis $A_2$. In this manner, the rolling diaphragm 112 has a first portion extending from an approximate longitudinal midpoint of the rolling diaphragm 112 to the distal end 130 and a second portion that is complementary in shape to the first portion and extending from the first portion to the proximal end 132. The fluid injector 102 (shown in FIG. 1) may have a controller with a built-in algorithm to provide a constant fluid flow regardless of the shape of the rolling diaphragm 112. For example, the controller may control the speed of the piston 138 (shown in FIG. 2) to increase or decrease the speed of the piston 138 at various longitudinal points to compensate for any fluid flow rate changes due to changes in a cross-sectional area of the rolling diaphragm 112 at such longitudinal points.

Figure 15A:
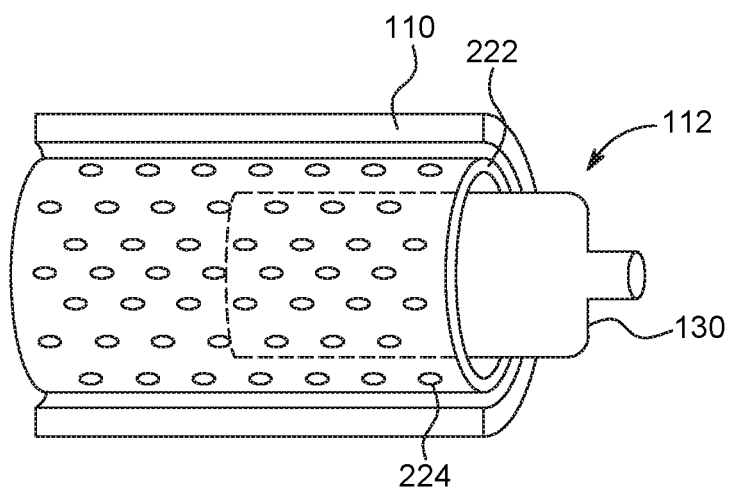
FIG. 15A is a perspective side view of a rolling diaphragm and an annular sleeve surrounding at least a portion of the rolling diaphragm in accordance with another aspect of the present disclosure.

FIG. 15A is a perspective side view of a rolling diaphragm 112 and an annular sleeve 222 surrounding at least a portion of the rolling diaphragm 112 in accordance with another aspect of the present disclosure. The annular sleeve 222 may have one or more openings 224 extending through a sidewall of the annular sleeve 222. In some aspects, the pressure jacket 110 may have a vacuum means for pulling the rolling diaphragm 112 against the inner sidewall 120 of the pressure jacket 110 or the annular sleeve 222. In yet another aspect, the pressure jacket 110 may have a pressure means for releasing the rolling diaphragm 112 from the pressure jacket 110 after use by introducing pressurized air through the one or more openings 224 of the annular sleeve 222. The inner sidewall of the annular sleeve 222 may be textured to prevent the outer surface of the rolling diaphragm 112 from sticking to the inner surface of the annular sleeve 222 and to facilitate the removal of the rolling diaphragm 112 from the annular sleeve 222 after use.

Figure 15B:
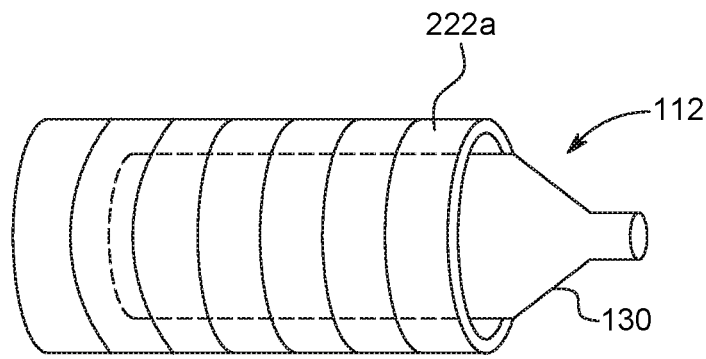
FIG. 15B is a perspective side view of a rolling diaphragm and an annular shrink-wrap sleeve surrounding at least a portion of the rolling diaphragm in accordance with another aspect of the present disclosure.

With reference to FIG. 15B, the rolling diaphragm 112 has an annular shrink-wrap sleeve 222a surrounding at least a portion of the rolling diaphragm 112. The shrink-wrap sleeve 222a may be heat activated such that it shrinks radially inward to compress against an outside sidewall 134 of the rolling diaphragm 112. The shrink-wrap sleeve 222a may be disposed between the pressure jacket 110 (not shown) and the rolling diaphragm 112.

Figure 15C:
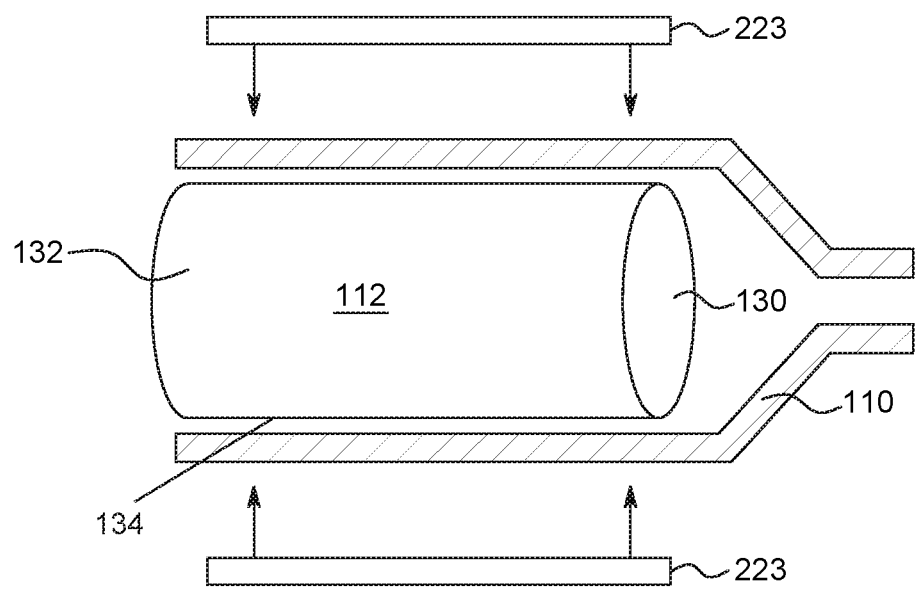
FIG. 15C is a perspective side view of a rolling diaphragm and a heating element surrounding at least a portion of the rolling diaphragm in accordance with another aspect of the present disclosure.

With reference to FIG. 15C, a heating element 223 may be provided around at least a portion of the rolling diaphragm 112. The heating element 223 may be disposed on the pressure jacket 110, such as an interior or exterior sidewall of the pressure jacket 110. In some aspects, the heating element 223 may be configured for pre-heating the sidewall 134 of the rolling diaphragm 112, for example to raise its pliability and facilitate inversion of the rolling diaphragm 112 when acted upon by the plunger 144 (not shown). The heating element may apply heat to the shrink-wrap sleeve shown in FIG. 15B.

Figure 16A:
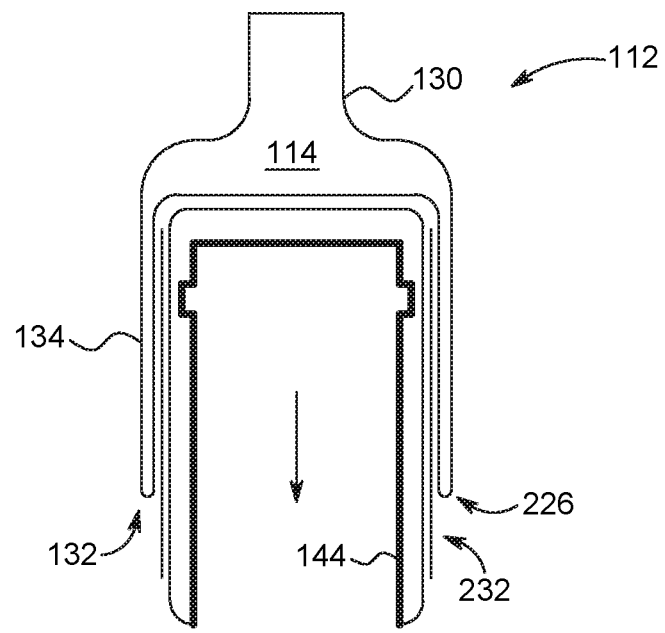
FIG. 16A is a cross-sectional side view of a rolling diaphragm and plunger in accordance with another aspect of the present disclosure.
Figure 16B:
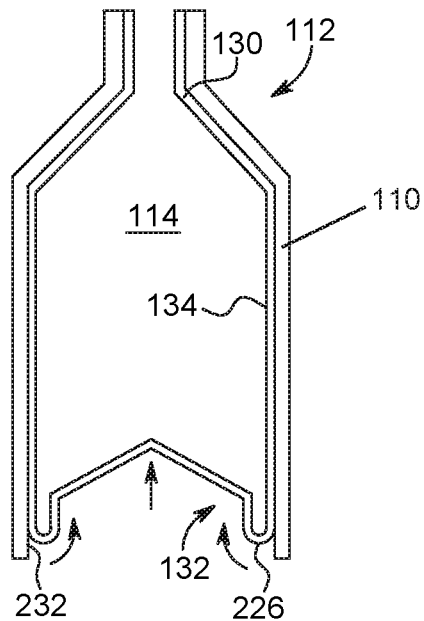
FIG. 16B is a cross-sectional side view of a rolling diaphragm in accordance with another aspect of the present disclosure.

FIG. 16A is a cross-sectional side view of a rolling diaphragm 112 and plunger 144 in accordance with another aspect of the present disclosure. According to this aspect, the rolling diaphragm 112 is initially in a collapsed or empty state. An adhesive layer 232 is disposed between at least a portion of the rolling diaphragm 112 and the plunger 144. The adhesive layer 232 may be adhered to at least a portion of the rolling diaphragm 112 and at least a portion of the plunger 144. The adhesive layer 232 may be releasable from one or both of the rolling diaphragm 112 and the plunger 144 upon movement of the plunger 144 in a proximal direction. In some aspects, the adhesive layer 232 may be provided on an outer portion of the sidewall 134 of the rolling diaphragm 112 before the sidewall 134 is rolled upon itself. The adhesive layer 232 may assist in preventing the buckling of the sidewall 134 when the inverted portion of sidewall 134 is engaged by the plunger 144. The internal volume 114 of the rolling diaphragm 112 may be initially empty. In order to withdraw the proximal end 132 of the rolling diaphragm 112 from the distal end 130 and fill the internal volume 114 with fluid, the plunger 144 engages the end wall and/or the sidewall 134 of an inverted portion of the rolling diaphragm 112. The adhesive layer 232 may be a pressure activated adhesive that applies an adhesive force on the inverted portion of sidewall 134 of the rolling diaphragm 112 as the plunger 144 is retracted in a proximal direction. The adhesive layer 232 may peel away from the sidewall 134 at the folding edge 226, or it may remain adhered to the sidewall 134 of the rolling diaphragm 112. The adhesive layer 232 may be an adhesive coating. The plunger 144 may have one or more piston engagement elements 234 configured for releasable engagement with a piston of an injector to allow for reciprocal movement of the plunger 144. In some aspects, the internal volume 114 of the rolling diaphragm 112 may have a vacuum that assists in drawing fluid into the rolling diaphragm 112 when the plunger 144 (not shown) is retracted in the proximal direction. In FIG. 16B, the adhesive layer 232, such as an adhesive coating, is disposed between the sidewall 134 of the rolling diaphragm 112 and the pressure jacket 110. In some aspects, the rolling diaphragm 112 peels away from the inner sidewall of the pressure jacket 110 as the plunger (not shown) urges the proximal end 132 of the rolling diaphragm 112 toward the distal end 130. A release layer (not shown) may be provided at the adhesion interface between the rolling diaphragm 112 and the pressure jacket 110.

Figure 17A:
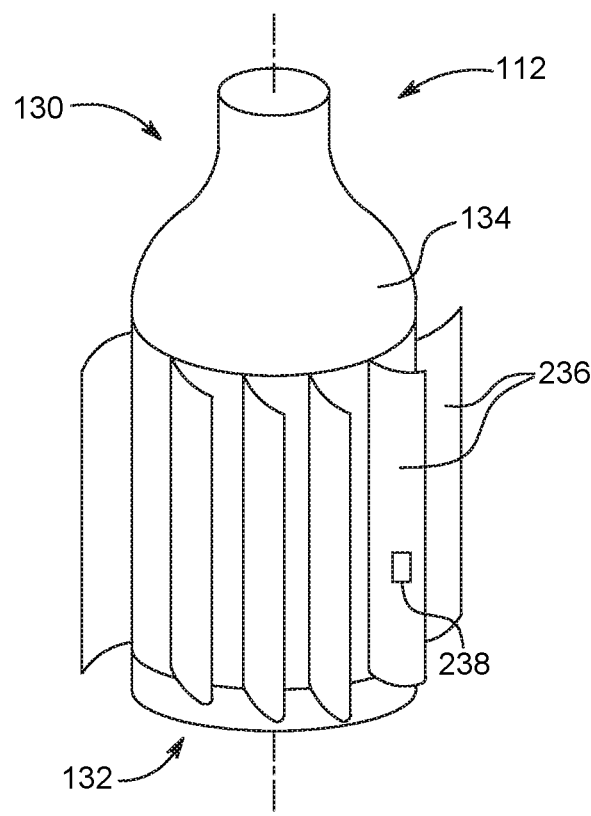
FIG. 17A is a perspective side view of a rolling diaphragm in accordance with another aspect of the present disclosure.
Figure 17B:
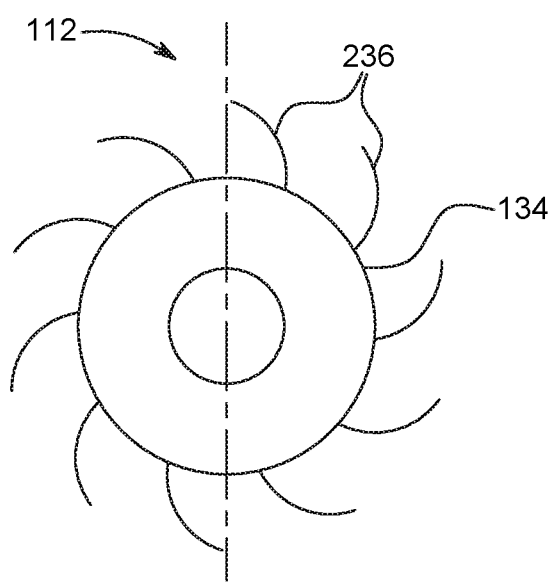
FIG. 17B is a top view of the rolling diaphragm shown in FIG. 17A.

FIG. 17A is a perspective side view of a rolling diaphragm 112 in accordance with another aspect of the present disclosure. FIG. 17B is a top view of the rolling diaphragm 112 shown in FIG. 17A. The rolling diaphragm 112 has a plurality of foldable tabs 236 around an outer circumference of the sidewall 134. A first end of each foldable tab 236 may be connected to the outer portion of the sidewall 134 while a second end is foldable relative to the first end in a circumferential direction of the outer portion of the sidewall 134. In a folded configuration, such as when all of the foldable tabs 236 are folded against the outer portion of the sidewall 134, the foldable tabs 236 may be aligned such that indicia 238, such as a label identifying the contents of the rolling diaphragm 112 may be identified.

Figure 18:
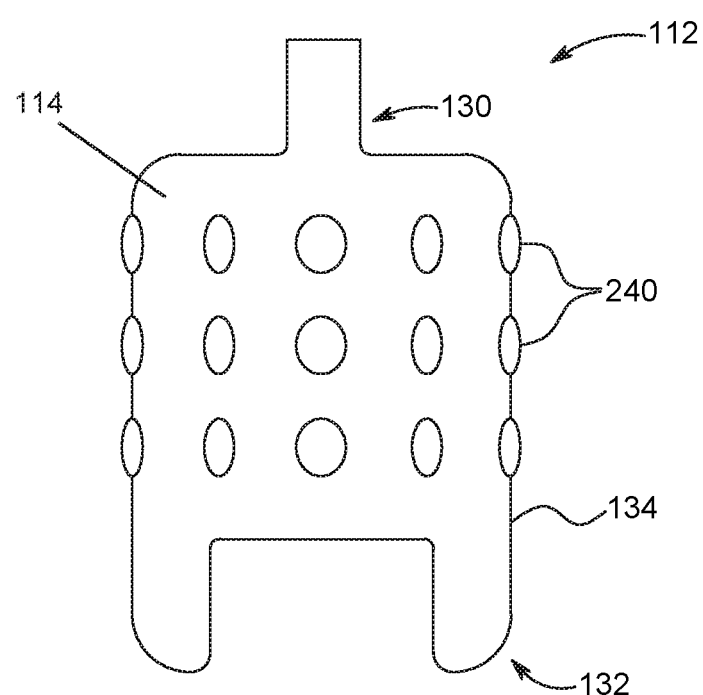
FIG. 18 is a side view of a rolling diaphragm in accordance with another aspect of the present disclosure.

FIG. 18 is a side view of a rolling diaphragm in accordance with another aspect of the present disclosure. The sidewall 134 of the rolling diaphragm 112 may have one or more fluid presence indicators 240 to indicate whether the internal volume 114 of the rolling diaphragm 112 is filled with fluid. The one or more fluid presence indicators 240 may be integrally formed with the sidewall 134 of the rolling diaphragm 112.

Figure 19:
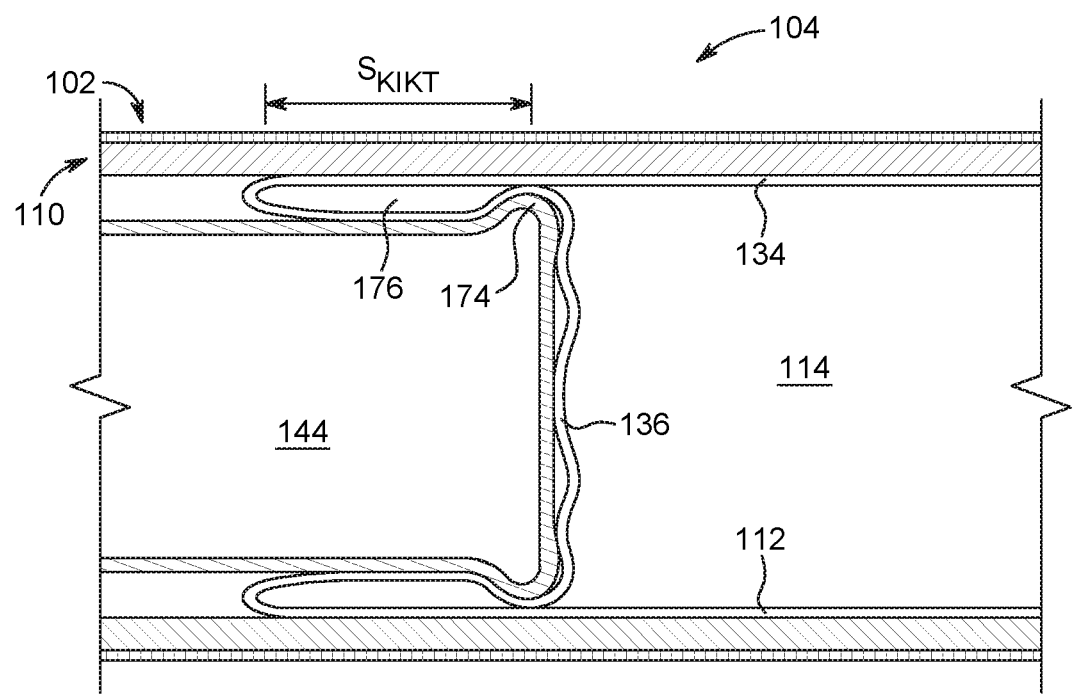
FIG. 19 is a cross-sectional side view of a rolling diaphragm and plunger in accordance with another aspect of the present disclosure.

FIG. 19 is a cross-sectional side view of a rolling diaphragm 112 and plunger 144 in accordance with another aspect of the present disclosure. The plunger 144 has a skirt 174 that extends radially outward from the distal end of the plunger 144. The skirt 174 is compressed against the sidewall 134 of the rolling diaphragm 112 such that it forces the fluid in a distal direction within the interior volume 114 forward as the plunger 144 is advanced in the distal direction. The skirt 174 minimizes or eliminates the residual volume of fluid in the fold 176.

Figure 20A:
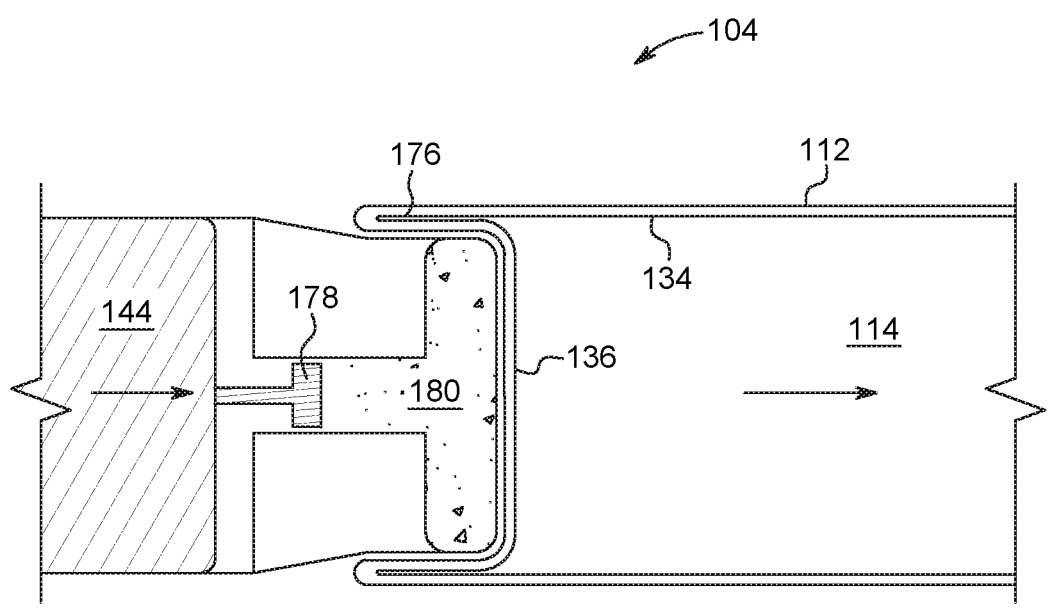
FIG. 20A is a cross-sectional side view of a rolling diaphragm and plunger in accordance with another aspect of the present disclosure.

FIG. 20A is a cross-sectional side view of a rolling diaphragm 112 and plunger 144 in accordance with another aspect of the present disclosure. The plunger 144 has a piston 178 at its distal end, such that the piston 178 is reciprocally moveable within a fluid- or elastomer-filled cavity 180 formed at the distal end of the plunger 144. As the plunger 144 is advanced in a distal direction, such as during fluid delivery from the interior volume 114 of the rolling diaphragm 112, the piston 178 is driven into the cavity 180, thereby increasing the pressure of the fluid or elastomer within the cavity 180. The cavity 180 is desirably flexible such that the increase in fluid or elastomer pressure causes the cavity 180 to expand against the sidewall 134 of the rolling diaphragm 112. The cavity 180 is compressed against the sidewall 134 of the rolling diaphragm 112 such that it forces the fluid within the interior volume 114 forward as the plunger 144 is advanced in the distal direction. The expansion of the cavity 180 minimizes or eliminates the residual volume of fluid in the fold 176. Upon retraction of the plunger 144 in the proximal direction, the piston 178 is also retracted from the cavity 180 to reduce the pressure therein and allow the plunger 144 to be retracted from the rolling diaphragm 112. In some aspects, the cavity 180 may be filled with an elastomer.

Figure 20B:
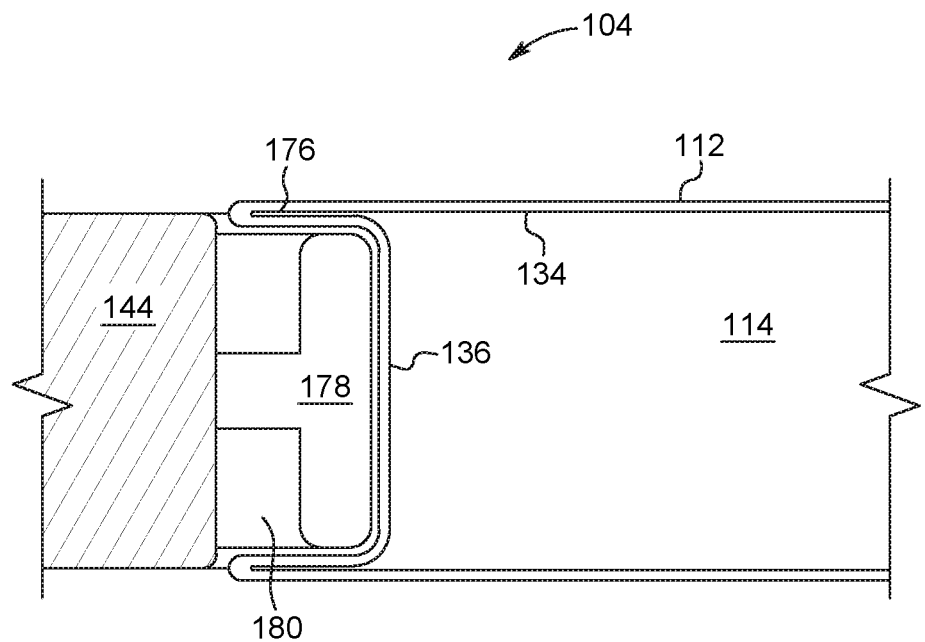
FIG. 20B is a cross-sectional side view of a rolling diaphragm and plunger in accordance with another aspect of the present disclosure.

FIG. 20B is a cross-sectional side view of a rolling diaphragm 112 and plunger 144 in accordance with another aspect of the present disclosure. Similar to the rolling diaphragm 112 shown in FIG. 20A, the plunger 144 has a piston 178 at its distal end, such that the piston 178 is reciprocally moveable within a fluid-filled cavity 180 formed at the distal end of the plunger 144. In some aspects, the cavity 180 may be filled with an elastomer. As the plunger 144 is withdrawn in a proximal direction, such as during filling of the rolling diaphragm 112, initially in a compressed or empty configuration, with fluid, the piston 178 may be independently moved in a proximal direction relative to the plunger 144, thereby increasing the pressure of the fluid within the cavity 180. The cavity 180 is desirably flexible such that the increase in fluid pressure causes the cavity 180 to expand against the sidewall 134 of the rolling diaphragm 112. The cavity 180 is compressed against the sidewall 134 of the rolling diaphragm 112 such that it contacts the sidewall 134 to increase the gripping force between the plunger 144 and the sidewall 134 as the plunger 144 is withdrawn in the proximal direction.

Figure 20C:
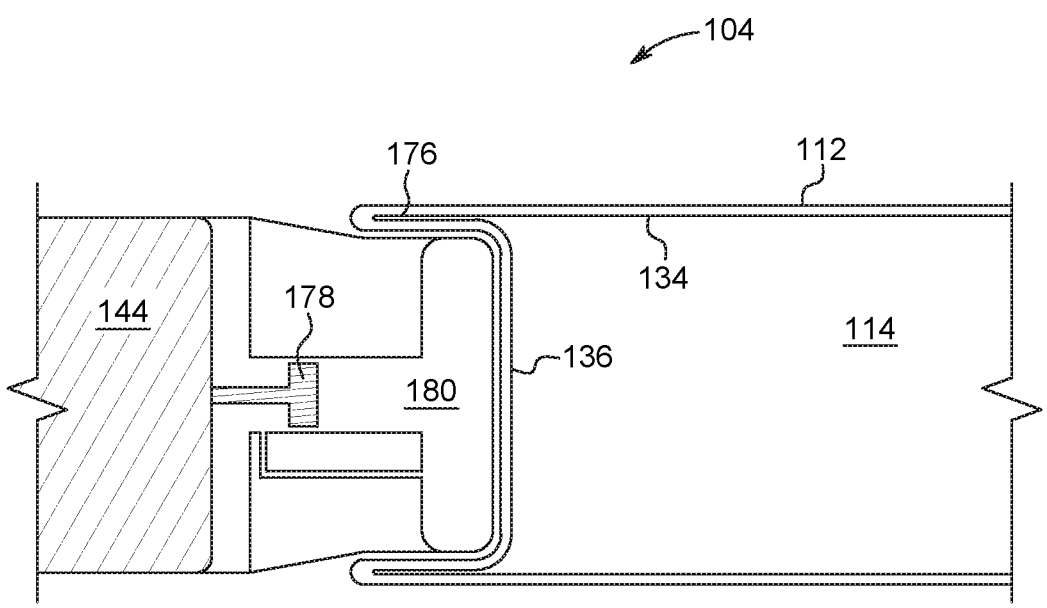
FIG. 20C is a cross-sectional side view of a rolling diaphragm and plunger in accordance with another aspect of the present disclosure.

FIG. 20C is a cross-sectional side view of a rolling diaphragm 112 and plunger 144 in accordance with another aspect of the present disclosure. Similar to the rolling diaphragm 112 shown in FIG. 20A, the plunger 144 has a piston 178 at its distal end, such that the piston 178 is reciprocally moveable within a fluid-filled cavity 180 formed at the distal end of the plunger 144. In some aspects, the cavity 180 may be filled with an elastomer. The cavity 180 has a first distal portion 180a and a second proximal portion 180b in fluid communication with the first distal portion 180a via a fluid line 180c. As the plunger 144 is withdrawn in a proximal direction, such as during filling of the rolling diaphragm 112 with fluid, the piston 178 may be independently moved in a proximal direction relative to the plunger 144, thereby forcing the fluid from the second proximal portion 180b into the first distal portion 180a through the fluid line 180c to increase the pressure of the fluid within the cavity 180. The outer diameter of the piston 178 may be smaller than an outer diameter of the second first distal portion 180 to increase a mechanical fluid advantage of the piston 178 in increasing the pressure in the first distal cavity 180a. The cavity 180 is desirably flexible such that the increase in fluid pressure causes the first distal portion 180a to expand against the sidewall 134 of the rolling diaphragm 112. The first distal portion 180a is compressed against the sidewall 134 of the rolling diaphragm 112 such that it contacts the sidewall 134 to increase the gripping force on the sidewall 134 as the plunger 144 is withdrawn in the proximal direction.

Figure 21A:
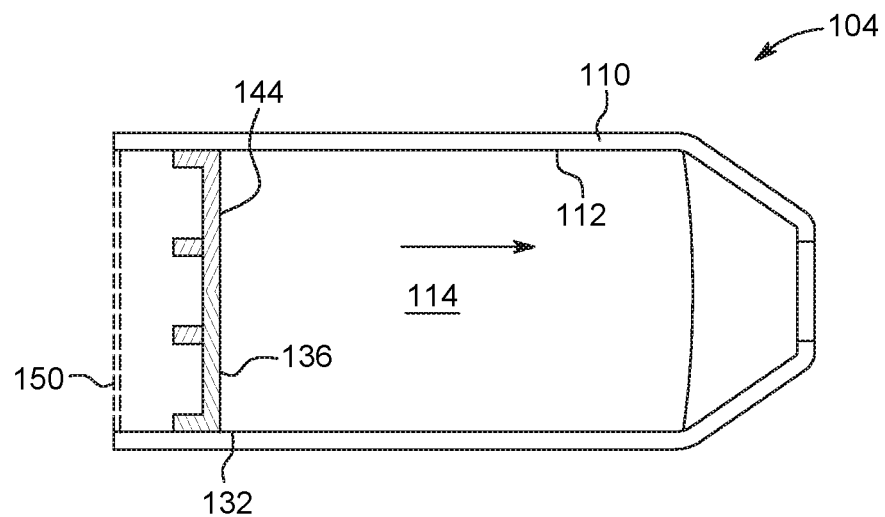
FIG. 21A is a cross-sectional side view of a rolling diaphragm and plunger in accordance with another aspect of the present disclosure.

FIG. 21A is a cross-sectional side view of a rolling diaphragm 112 and plunger 144 in accordance with another aspect of the present disclosure. The rolling diaphragm 112 has a built-in plunger 144. In some aspects, the plunger 144 is disposed within the interior volume 114 of the rolling diaphragm 112. Alternatively, the plunger 144 may be formed, such as by molding or by adhesion, at the proximal end 132 of the rolling diaphragm 112. Prior to use, the proximal end 132 of the rolling diaphragm 112 is sealed with a seal 150 to prevent removal of the plunger 144.

Figure 21B:
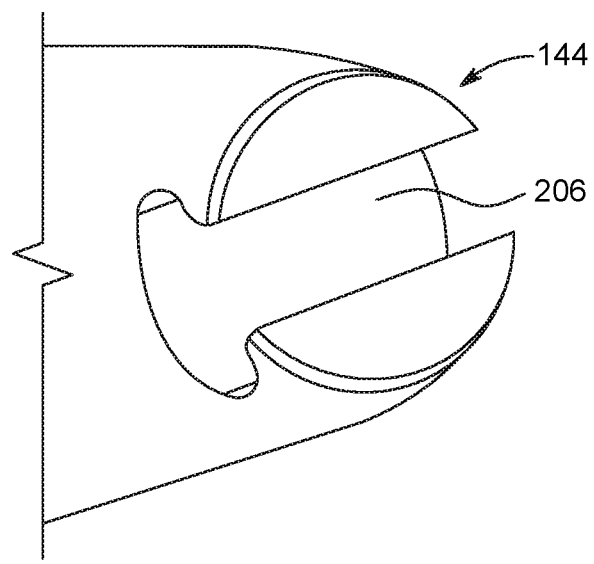
FIG. 21B is a perspective side view of a plunger in accordance with another aspect of the present disclosure.
Figure 21C:
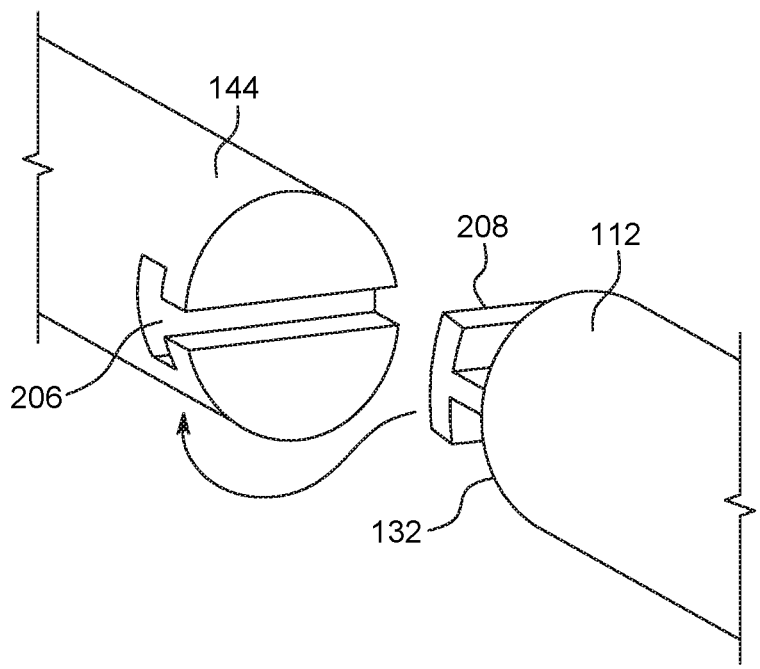
FIG. 21C is a perspective side view of a rolling diaphragm and the plunger shown in FIG. 21B.
Figure 23:
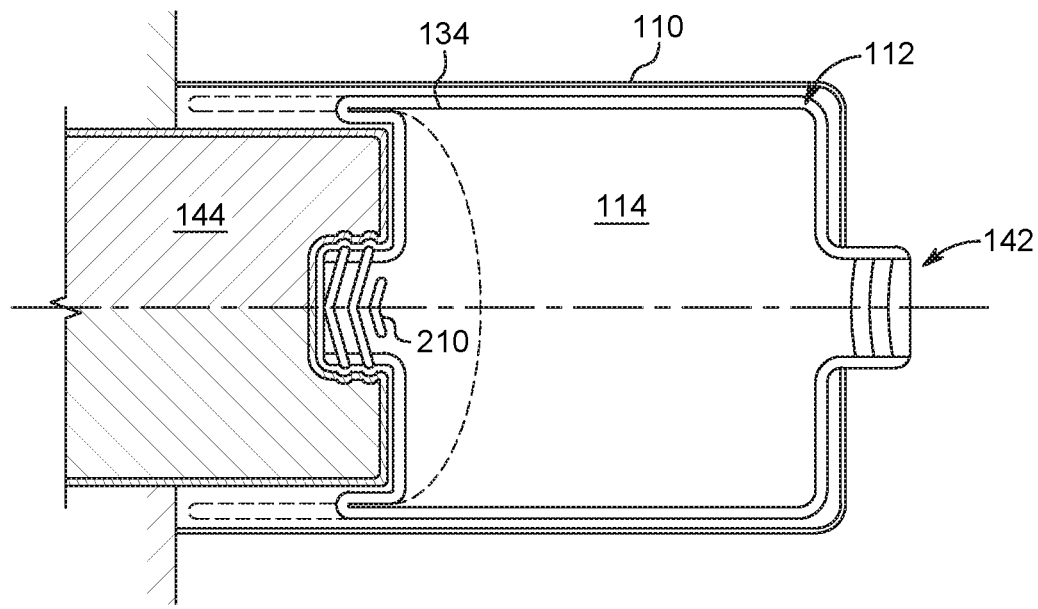
FIG. 23 is a cross-sectional side view of a rolling diaphragm and plunger in accordance with another aspect of the present disclosure.
Figure 26A:
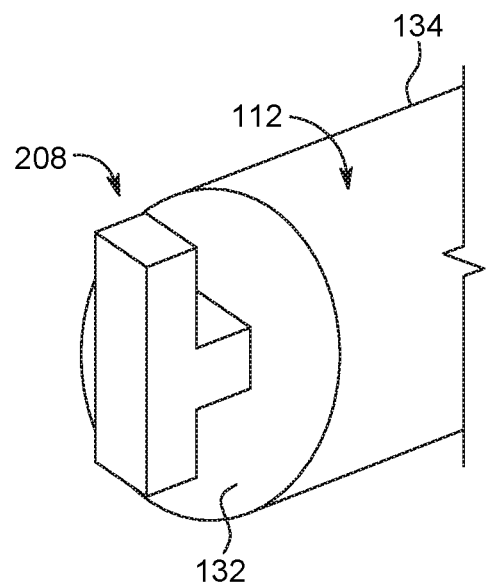
FIG. 26A is a perspective view of a plunger in accordance with another aspect of the present disclosure.
Figure 26B:
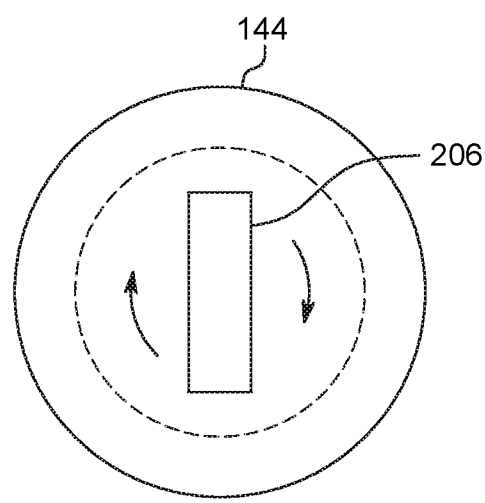
FIG. 26B is a top view of the plunger shown in FIG. 26A.

FIG. 21B is a perspective side view of a plunger 144 in accordance with another aspect of the present disclosure. FIG. 21C is a perspective side view of a rolling diaphragm 112 and the plunger 144 shown in FIG. 21B. The plunger 144 has a groove 206 shaped into the distal end of the plunger 144. In operation, the groove 206 captures at least a portion of the sidewall 134 or the end wall at the proximal end 132 of the rolling diaphragm 112 to facilitate the rollover of the sidewall 134. As shown in FIG. 21C, the groove 206 may be shaped to receive a projection 208 formed at the proximal end 132 of the rolling diaphragm 112. The groove 206 may have a T-shaped configuration that corresponds to the shape of the projection 208. A variety of other shapes, including, but not limited to, oval, rectangular, triangular, etc. are also contemplated. In a further aspect, such as shown in FIGS. 26A-26B, the groove 206 is in the form of a slot shaped to receive the projection 208. The groove 206 is arranged on one of the plunger 144 and the rolling diaphragm 112, while the projection 208 is arranged on the other of the plunger 144 and the rolling diaphragm 112. The groove 206 is shaped such that the projection 208 can be inserted in one direction only. Once inserted into the groove 206, the projection 208 may be rotated relative to the groove 206 in order to lock the plunger 144 relative to the rolling diaphragm 112. To remove the projection 208 from the groove 206, the projection 208 is desirably rotated such that it is aligned with the groove 206 in a direction corresponding to the insertion direction. In yet another aspect, such as shown in FIGS. 23-24, the plunger 144 is connected to the rolling diaphragm 112 by a threaded member 210 having a male thread feature on one of the plunger 144 and the rolling diaphragm 112 that threadably engage a female threaded feature on the other of the plunger 144 and the rolling diaphragm 112. An embodiment where the position of the male and female threaded features are reversed is also contemplated.

Figure 22:
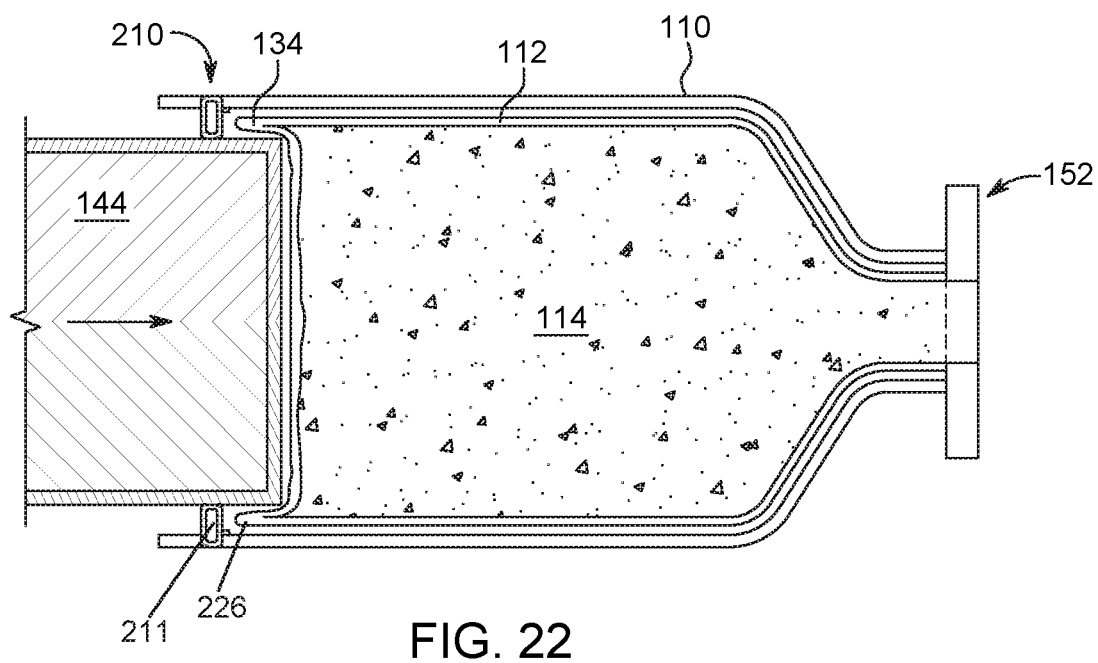
FIG. 22 is a cross-sectional side view of a rolling diaphragm and plunger in accordance with another aspect of the present disclosure.

FIG. 22 is a cross-sectional side view of a rolling diaphragm and plunger in accordance with another aspect of the present disclosure. The distal end of the plunger 144 has a projection 211 that extends radially outward from the plunger 144 to engage the sidewall 134 of the rolling diaphragm 112. The projection 211 may engage the folding edge 226 of the rolling diaphragm 112 to facilitate rolling over of the folding edge 226 as the plunger 144 is advanced in a distal direction.

Figure 24A:
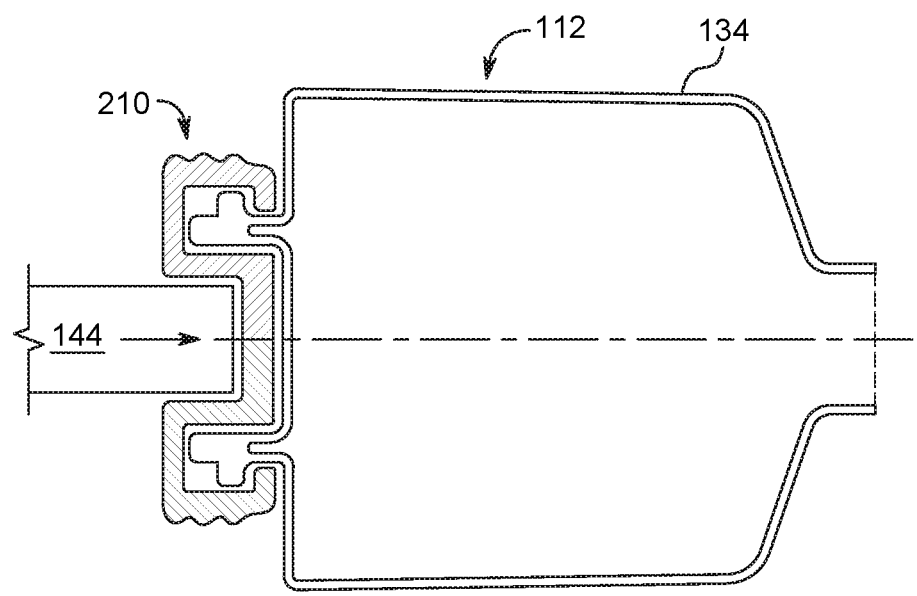
FIG. 24A is a cross-sectional side view of a rolling diaphragm and plunger in accordance with another aspect of the present disclosure.

FIG. 23-24A is a cross-sectional side view of a rolling diaphragm 112 and plunger 144 in accordance with another aspect of the present disclosure. The plunger 144 is connected to the rolling diaphragm 112 by a threaded member 210 having a male threaded feature on the plunger 144 that threadably engages a female threaded feature on the rolling diaphragm 112. In some aspects, the threaded member 210 has a female threaded feature on the plunger 144 that threadably engages a male threaded feature on the rolling diaphragm 112.

Figure 24B:
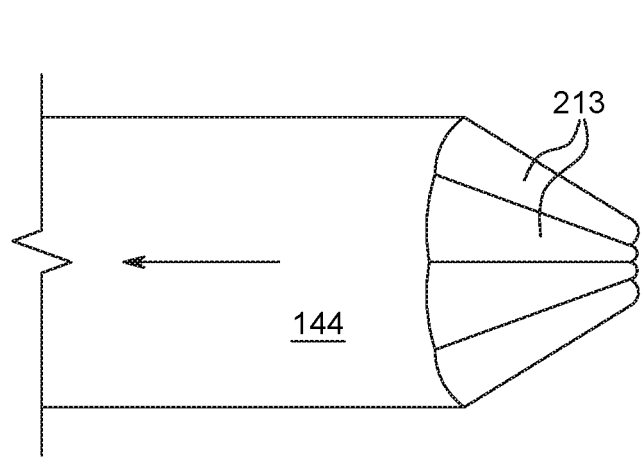
FIG. 24B is a perspective view of a plunger in accordance with another aspect of the present disclosure, with the plunger shown in a first, retracted state.
Figure 24C:
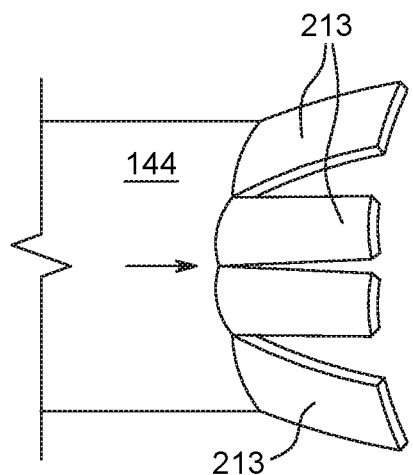
FIG. 24C is a perspective view of the plunger illustrated in FIG. 24B shown in a second, expanded state.
Figure 25A:
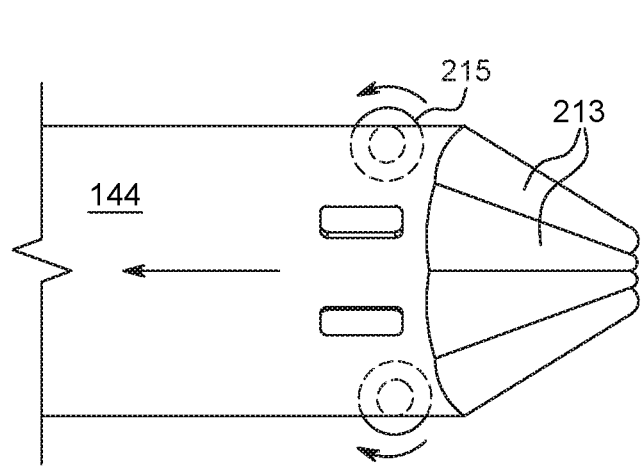
FIG. 25A is a perspective view of a plunger in accordance with another aspect of the present disclosure, with the plunger shown in a first, retracted state.
Figure 25B:
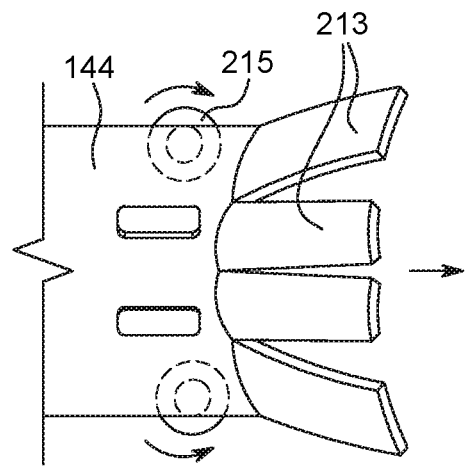
FIG. 25B is a perspective view of the plunger illustrated in FIG. 25A shown in a second, expanded state.
Figure 25C:
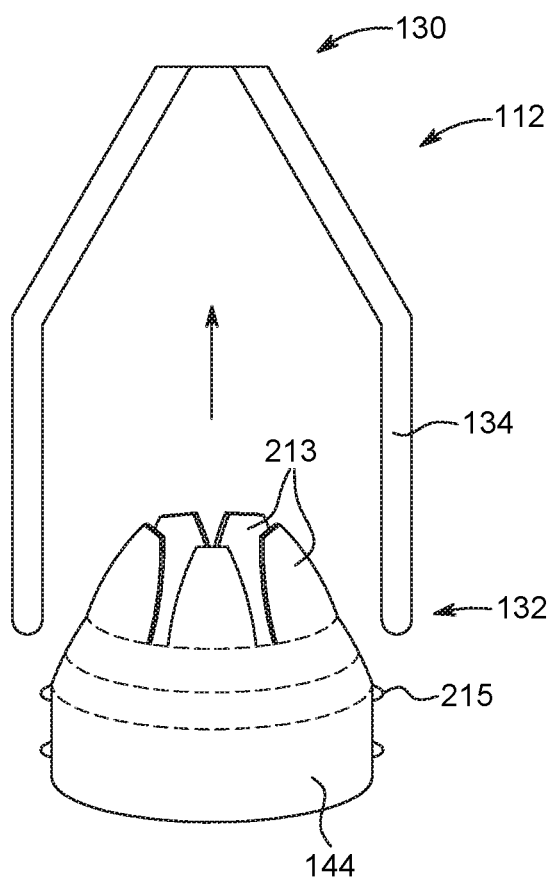
FIG. 25C is a side view of a rolling diaphragm and the plunger shown in FIGS. 25A-25B.

FIG. 24B is a perspective view of a plunger 144 in accordance with another aspect of the present disclosure, with the plunger 144 shown in a first, retracted state. FIG. 24C is a perspective view of the plunger 144 illustrated in FIG. 24C shown in a second, expanded state. The plunger 144 has one or more expandable ribs 213 at the distal end that are expandable radially outward from a first, retracted state (shown in FIG. 24B) to a second, expanded state (FIG. 24C). The one or more expandable ribs 213 may be automatically expandable and retractable depending on the distal or proximal movement of the plunger 144. In some aspects, the one or more expandable ribs 213 may expand radially outward to engage the sidewall 134 of the rolling diaphragm 112 (not shown) when the plunger 144 is advanced in the distal direction to expel fluid from the rolling diaphragm 112. In other aspects, the one or more expandable ribs 213 may expand radially outward to engage the sidewall 134 of the rolling diaphragm 112 (not shown) when the rolling diaphragm 112 is in the empty, collapsed stated and the plunger 144 is retracted in the proximal direction to fill the rolling diaphragm 112 with fluid. FIGS. 25A-25C show the plunger 144 with one or more rollers 215 on a non-expandable portion of the plunger 144. The rollers 215 engage the sidewall 134 of the rolling diaphragm 112 (shown in FIG. 25C) and may be freely rotatable in a direction of plunger movement.

Figure 27:
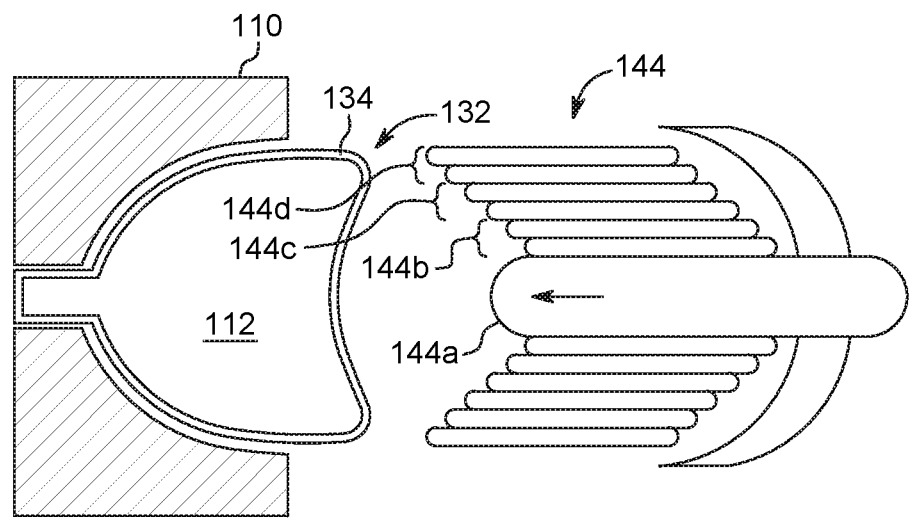
FIG. 27 is a cross-sectional side view of a rolling diaphragm and plunger in accordance with another aspect of the present disclosure.
Figure 28A:
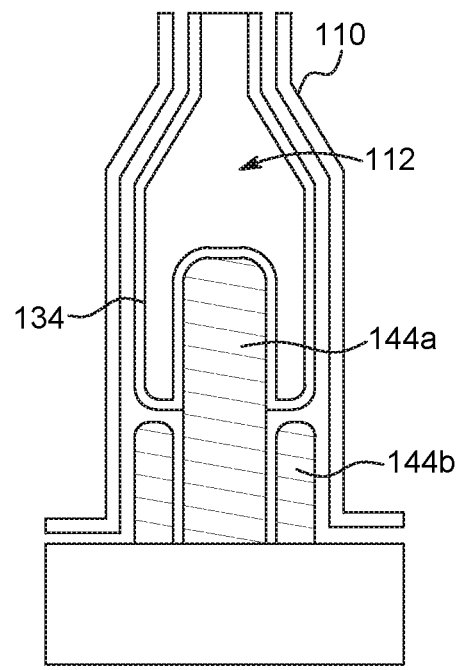
FIG. 28A is a cross-sectional side view of a rolling diaphragm and plunger in accordance with another aspect of the present disclosure, with the plunger shown in a first axial position.
Figure 28B:
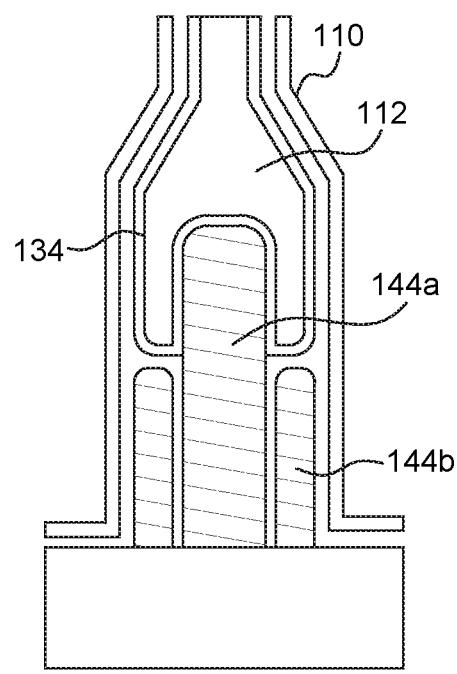
FIG. 28B is a cross-sectional side view of the rolling diaphragm and plunger shown in FIG. 28A, with the plunger shown in a second axial position.
Figure 28C:
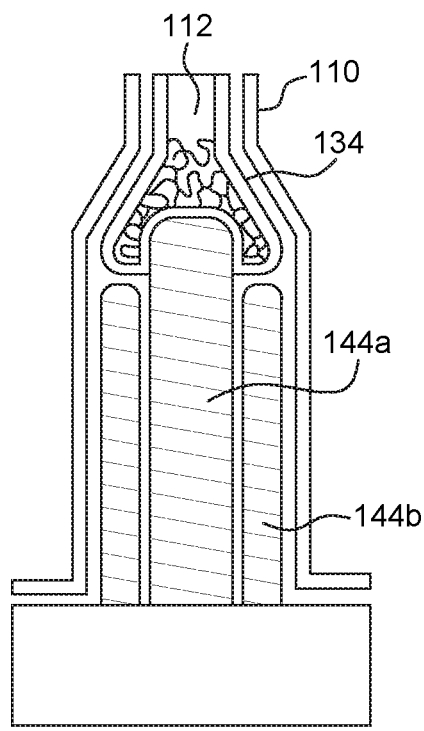
FIG. 28C is a cross-sectional side view of the rolling diaphragm and plunger shown in FIG. 28A, with the plunger shown in a third axial position.

FIGS. 27-28C is a cross-sectional side view of a rolling diaphragm 112 and plunger 144 in accordance with other aspects of the present disclosure. The plunger 144 has a plurality of concentric portions 144a-144d arranged in a telescoping orientation relative to each other. Each of the concentric portions 144a-144d may be advanced in a proximal or distal direction independently of the remaining concentric portions 144a-144d. In one aspect, outer concentric portions may support the proximal end 132 of the rolling diaphragm 112 while the inner concentric portions are advanced to deliver the fluid from the rolling diaphragm 112. Controlling the movement of individual concentric portions 144a-144d allows for a more uniform compression of the rolling diaphragm 112 and a complete expulsion of fluid from the rolling diaphragm 112. In addition, by selectively withdrawing individual concentric portions 144a-144d in a proximal direction, the rolling diaphragm 112 can be more easily removed from the plunger 144 after compression.

Figure 29:
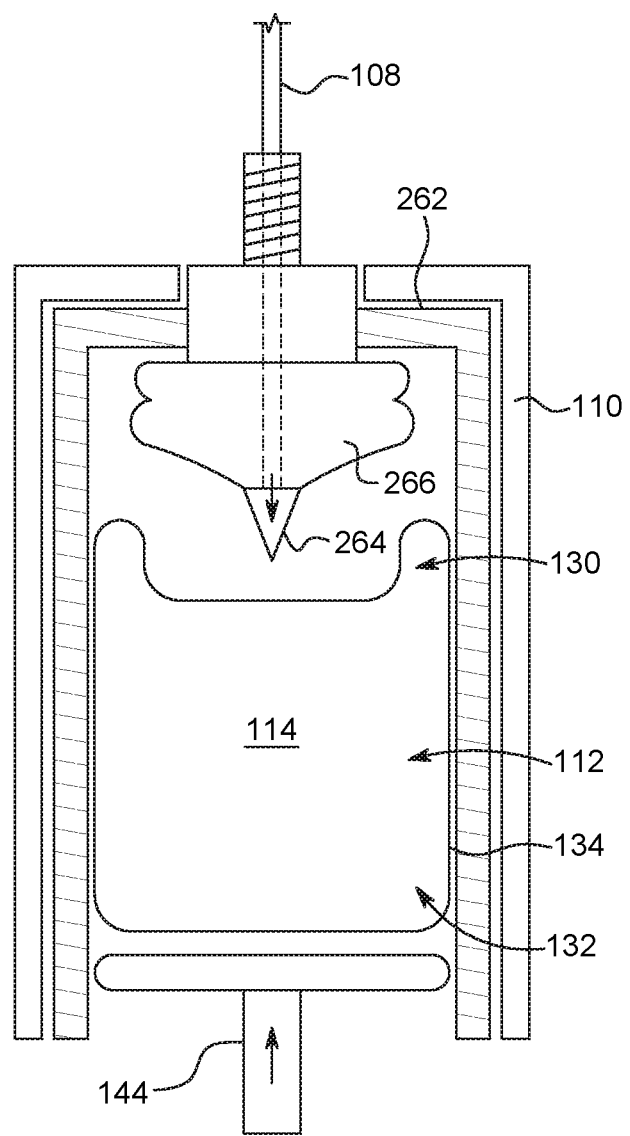
FIG. 29 is a cross-sectional side view of a rolling diaphragm and plunger in accordance with another aspect of the present disclosure.

FIG. 29 is a cross-sectional side view of a rolling diaphragm and plunger in accordance with another aspect of the present disclosure. The rolling diaphragm 112 may be formed as a flexible container with or without a defined outlet port at the distal end 130. The rolling diaphragm 112 may be retained within a pressure jacket 110 and acted upon by a plunger 144 at the proximal end 132 of the rolling diaphragm 112. Movement of the plunger 144 in the distal direction compresses the rolling diaphragm 112 against a distal sidewall 262 of the pressure jacket 110. A piercing element 264 having a seal 266 is provided at the distal sidewall 262 of the pressure jacket 110. As the plunger 144 compresses the rolling diaphragm 112 against the distal sidewall 262 of the pressure jacket 110, the piercing element 264 pierces through the sidewall 134 of the rolling diaphragm 112 to bring the fluid path set 108 in fluid communication with the internal volume 114 of the rolling diaphragm 112. The seal 266 seals around the pierced portion of the sidewall 134 to prevent fluid from leaking into the pressure jacket 110.

Figure 30:
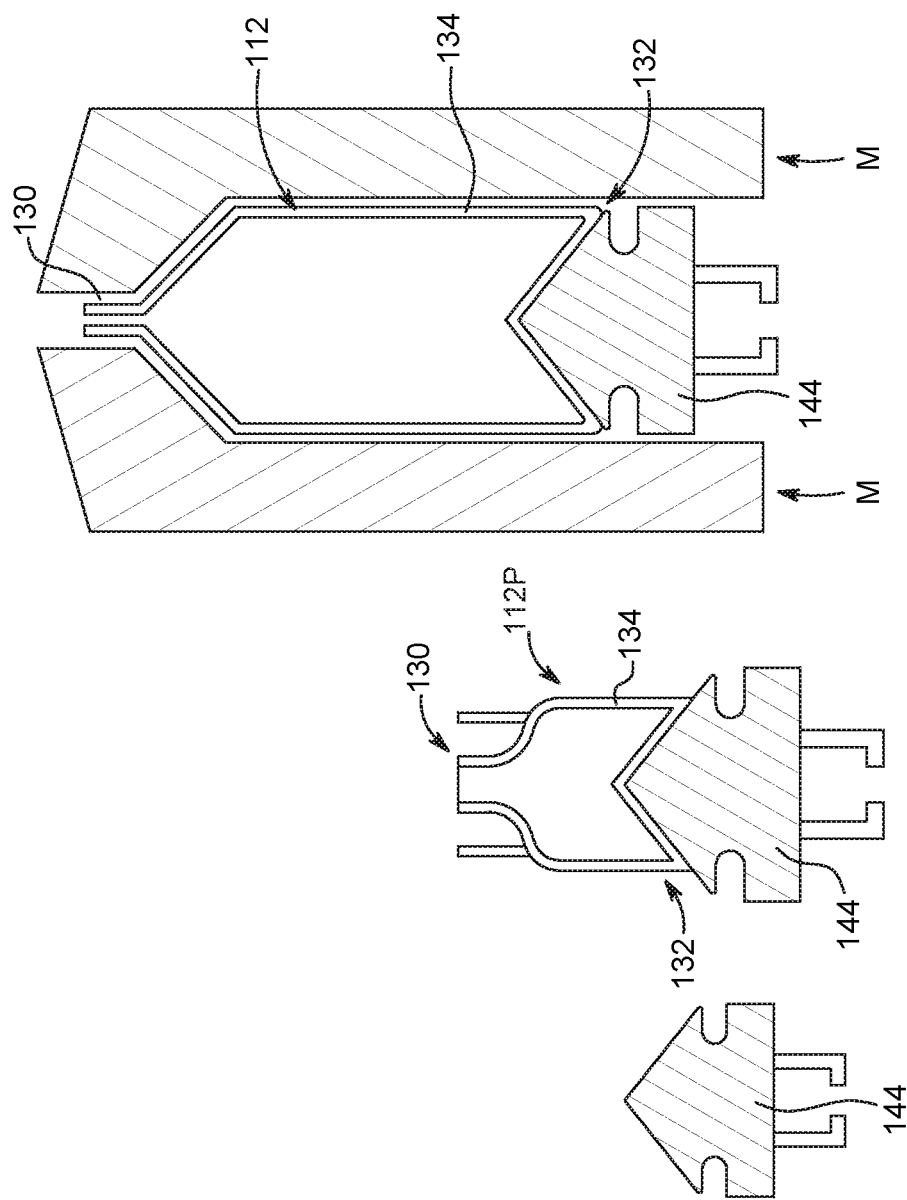
FIG. 30 is a cross-sectional side view of a rolling diaphragm and plunger in accordance with another aspect of the present disclosure.

FIG. 30 is a cross-sectional side view of a rolling diaphragm 112 and plunger 144 in accordance with another aspect of the present disclosure. The rolling diaphragm 112 is co-molded with the plunger 144. In some aspects, the plunger 144 may be a rigid, substantially non-deformable plunger, while the rolling diaphragm 112 may have a flexible sidewall 134 that may be rolled over on itself to allow the internal volume 114 of the rolling diaphragm 112 to expand or contract. Initially, the rolling diaphragm 112p may be in a pre-formed configuration which is co-molded with the plunger 144. After co-molding the rolling diaphragm preform 112p with the plunger 144, the rolling diaphragm pre-form 112p may be expanded to its final form by a blow molding technique in a mold M. For example, the rolling diaphragm pre-form 112p may be expanded by a stretch blow molding technique. The plunger 144 may be fixed in the mold M while at least a portion of the rolling diaphragm pre-form 112p is expanded by blow molding. In some aspects, a first portion of the rolling diaphragm 112 is fixed in the mold M, while a second portion of the rolling diaphragm 112 is expanded, during which expansion the plunger 144 may move within the mold M. Alternatively, the rolling diaphragm 112 may be molded to its final, expanded shape and the plunger 144 may be co-molded with the rolling diaphragm 112. In some aspects, a first portion of the rolling diaphragm 112, such as the proximal or the distal end, may be pre-formed, while a second portion of the rolling diaphragm 112 may be expanded, such as by a stretch blow molding technique.

Figure 31:
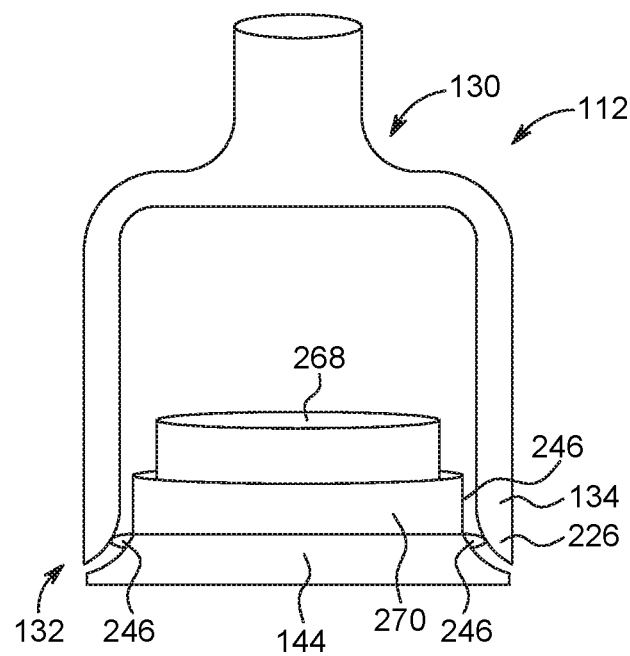
FIG. 31 is a cross-sectional side view of a rolling diaphragm and plunger in accordance with another aspect of the present disclosure.

FIG. 31 is a cross-sectional side view of a rolling diaphragm 112 and plunger 144 in accordance with another aspect of the present disclosure. The plunger 144 has an inner element 268 and an outer element 270 surrounding the inner element 268 and movable relative to the outer element 270. The outer element 270 has one or more gripping elements 246 protruding radially outward from an outer circumference of the outer element 270. The one or more gripping elements 246 of the outer element 270 engage the sidewall 134 of the rolling diaphragm 112 at the folding edge 226. The one or more gripping elements 246 may be retractable when engaged by at least a portion of the inner element 268 or the outer element 270. The plunger 144 reciprocally moves the inner element 268 relative to the outer element 270 in a series of incremental strokes. Each stroke has a distal component and a proximal component, with the proximal component being longer than the distal component. In this manner, the plunger 144 has a net movement in the proximal direction. With each distal movement of the plunger 144, the inner element 268 moves distally relative to the outer element 270, which releases a radial loading on the outer element 270 and reduces the grip of the gripping elements 246 (such as by withdrawing the gripping elements 246 into the outer element 270) from the sidewall 134 of the rolling diaphragm 112. The outer element 270 can then be advanced distally to engage the sidewall 134 distally of the folding edge 226. With each proximal movement of the plunger 144, the inner element 268 moves proximally relative to the outer element 270, which increases the radial loading on the outer element 270 and engages the gripping elements 246 with the sidewall 134 of the rolling diaphragm 112. The outer element 270 draws the sidewall 134 of the rolling diaphragm 112 in the proximal direction until it reaches the folding edge 226, after which the plunger movement is repeated. In this manner, the internal volume 114 of the rolling diaphragm 112 can be filled with fluid. Fluid can be discharged from the rolling diaphragm 112 in a manner described herein. In some aspects, the outer element 270 may be an expandable element that has a resiliently deflectable element, such as a spring, that expands radially outward to contact the sidewall 134 of the rolling diaphragm 112 upon engagement of the plunger 144 with the outer element 270.

Figure 32A:
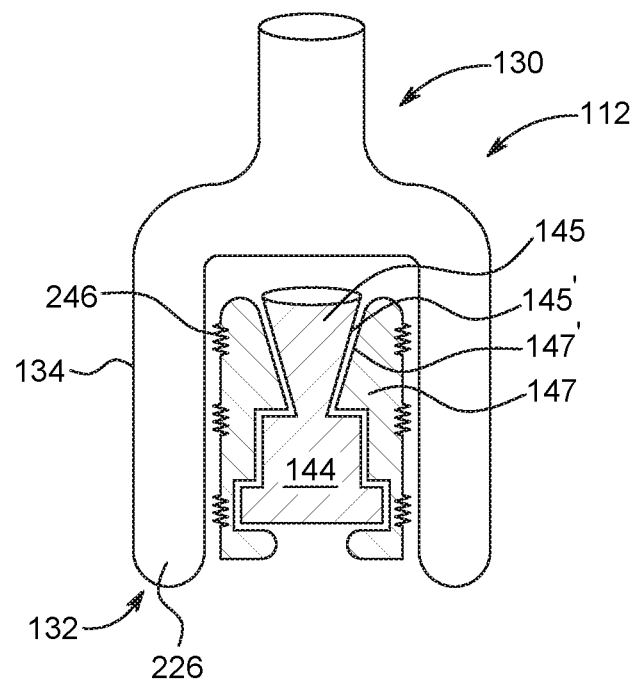
FIG. 32A is a cross-sectional side view of a rolling diaphragm and plunger in accordance with another aspect of the present disclosure.
Figure 32B:
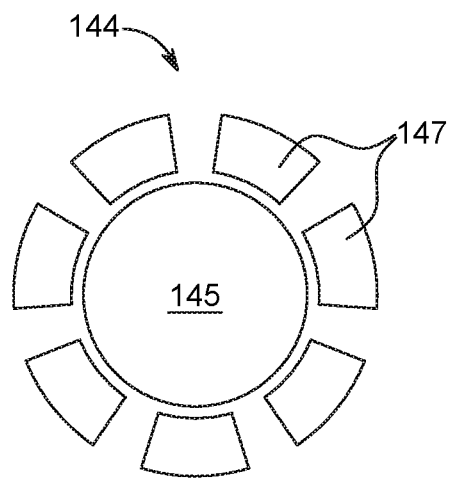
FIG. 32B is a top view of the plunger shown in FIG. 32A.

FIG. 32A is a cross-sectional side view of a rolling diaphragm 112 and plunger 144 in accordance with another aspect of the present disclosure. FIG. 32B is a top view of the plunger 144 shown in FIG. 32A. The plunger 144 has a central portion 145 and a plurality of radially extendable elements 147 operatively connected to the central portion 145. The central portion 145 has a first ramp surface 145' that defines a substantially conical distal portion of the central portion 145. Each of the radially extendable elements 147 has a second ramp surface 147' that corresponds to the first ramp surface 145' on the central portion 145. The plunger 144 is initially inserted in an inverted rolling diaphragm 112. Movement of the central portion 145 in a proximal direction causes the first ramp surface 145' of the central portion 145 to engage the second ramp surface 147' on at least one of the plurality of radially extendable elements 147. Due to a slope of the first and second ramp surfaces 145', 147', a radial movement component is imparted on at least one of the radially extendable elements 147 as a result of proximal movement of the central portion 145. Such radial movement of at least one of the radially extendable elements 147 causes a gripping surface 147" of at least one of the radially extendable elements 147 to engage the folded portion of the sidewall 134 of the rolling diaphragm 112 as plunger 144 is retracted.

Figure 33A:
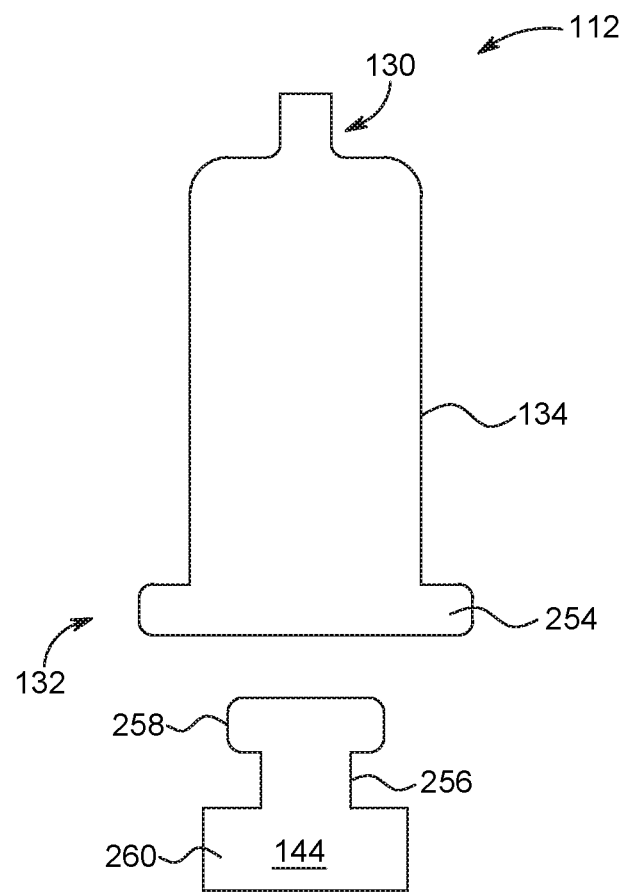
FIG. 33A is a cross-sectional side view of a rolling diaphragm and plunger in accordance with another aspect of the present disclosure, with the plunger shown in a first axial position.
Figure 33B:
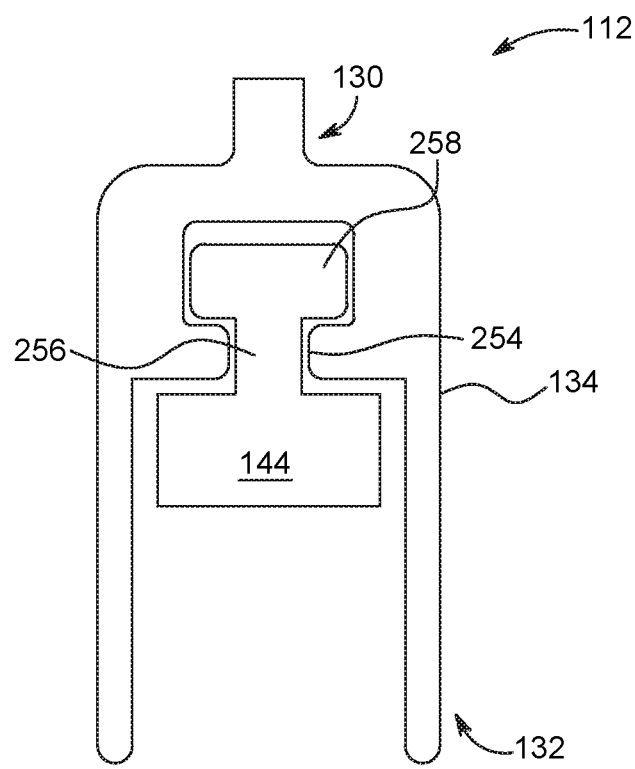
FIG. 33B is a cross-sectional side view of the rolling diaphragm and plunger shown in FIG. 33A, with the plunger shown in a second axial position.

FIG. 33A is a cross-sectional side view of a rolling diaphragm 112 and plunger 144 in accordance with another aspect of the present disclosure, with the plunger 144 shown in a first axial position. FIG. 33B is a cross-sectional side view of the rolling diaphragm 112 and plunger 144 shown in FIG. 33A, with the plunger 144 shown in a second axial position. The proximal end 132 of the rolling diaphragm 112 has a plunger engagement portion 254 formed as a ring that protrudes radially outward relative to the sidewall 134 at the proximal end 132 of the rolling diaphragm 112. The plunger engagement portion 254 may extend continuously or discontinuously around the circumference of the proximal end 132 of the rolling diaphragm 112. The plunger 144 has a radially inwardly recessed portion 256 that is configured to coact with the plunger engagement portion 254 of the rolling diaphragm 112 upon movement of the plunger 144 in a distal direction. In some aspects, the plunger engagement portion 254, which initially protrudes in a radially outward direction on the rolling diaphragm 112 that is uncompressed, as shown in FIG. 33A, is inverted to protrude radially inward, as shown in FIG. 33B, when the sidewall 134 of the rolling diaphragm 112 folds over due to movement of the plunger 144 in the distal direction. When the plunger engagement portion 254 is folded over in a radially inward direction, the recessed portion 256 of the plunger 144 receives the plunger engagement portion 254 such that the plunger engagement portion 254 is retained axially between a collar 258 at a distal end of the recessed portion 256 and a plunger base 260 at a proximal end of the recessed portion 256. The collar 258 of the plunger 144 may be retractable radially inward to allow the plunger 144 to be released from the plunger engagement portion 254 of the rolling diaphragm 112.

Figure 34A:
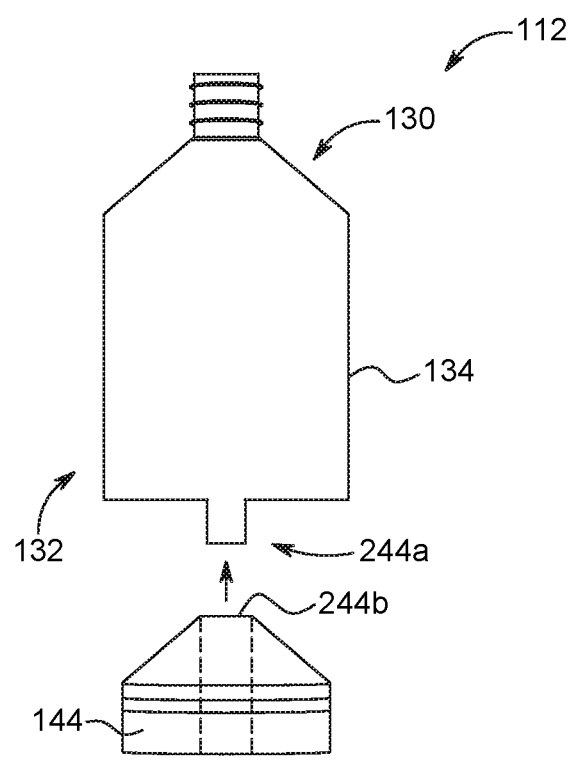
FIG. 34A is a cross-sectional side view of a rolling diaphragm and plunger in accordance with another aspect of the present disclosure, with the plunger shown in a first axial position.
Figure 34B:
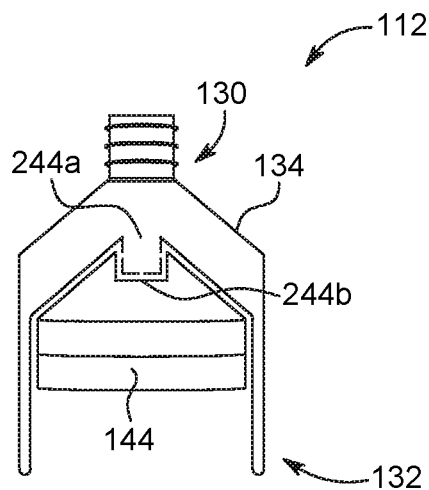
FIG. 34B is a cross-sectional side view of the rolling diaphragm and plunger shown in FIG. 34A, with the plunger shown in a second axial position.

FIG. 34A is a cross-sectional side view of a rolling diaphragm 112 and plunger 144 in accordance with another aspect of the present disclosure, with the plunger 144 shown in a first axial position. FIG. 34B is a cross-sectional side view of the rolling diaphragm 112 and plunger 144 shown in FIG. 34A, with the plunger 144 shown in a second axial position. The rolling diaphragm 112 has a first engagement portion 244a formed at the proximal end 132 of the rolling diaphragm 112. The first engagement portion 244a is configured for engagement with the plunger 144. In some aspects, the first engagement portion 244a is formed as a tab extending proximally from a central portion of the proximal end 132. The first engagement portion 244a may be non-deformable or deformable, such as by heating. The first engagement portion 244a is connectable to a second engagement portion 244b formed on the plunger 144. The second engagement portion 244b may be formed as a recess configured to receive the tab of the first engagement portion 244a. In some aspects, the first engagement portion 244a may be releasably or non-releasably connected to the second engagement portion 244a. For example, at least a portion of the first engagement portion 244a may be permanently and non-releasably coupled with the second engagement portion 244b by fusing or adhering at least a portion of the first engagement portion 244a with the second engagement portion 244b, such as by heating at least a portion of the first engagement portion 244a. In some aspects, at least a portion of the first engagement portion 244a may be releasably coupled with the second engagement portion 244b via a snap-fit connection, or via a threaded connection. Once connected, the first engagement portion 244a and the second engagement portion 244b allow the plunger 144 to reciprocally move to allow filling or discharging the rolling diaphragm 112.

In some aspects, the first engagement portion 244a is formed as a tab 244c extending proximally from a central portion of the proximal end 132 with a lip 244d protruding radially outward from a proximal end of the tab 244c. The first engagement portion 244a is connectable to a second engagement portion 244d formed on the plunger 144. The second engagement portion 244b may have a pair of radially deflectable fingers 244e configured to engage the lip 244d of the first engagement portion 244a. The radially deflectable fingers 244e may be deflectable from a first position to a second position to clear the lip 244d as the plunger 144 is advanced distally to lock the second engagement portion 244b with the first engagement portion 244a. Once locked, a radial deflection of the fingers 244e may be prevented by a collar that extends around at least a portion of the fingers 244e. In some aspects, the fingers 244e may be locked against the pressure jacket 110 (shown in FIG. 2) to prevent disengagement of the fingers 244e from the first engagement portion 244a during withdrawal of the plunger 144 in a proximal direction, such as during filling of the rolling diaphragm 112.

Figure 35:
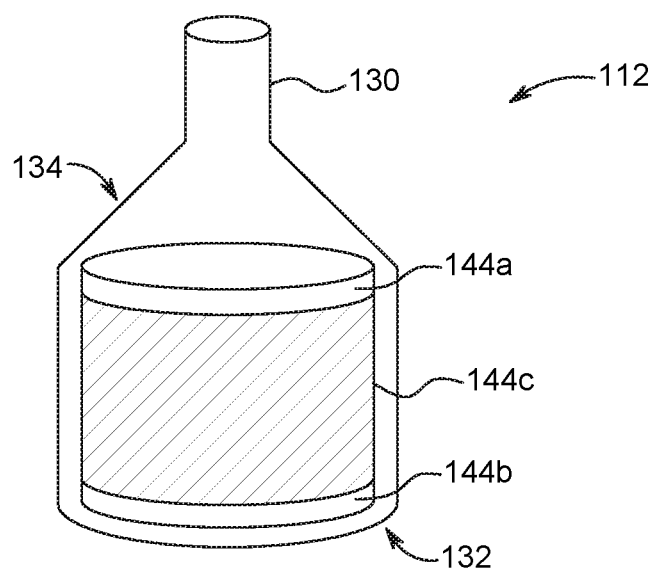
FIG. 35 is a cross-sectional side view of a rolling diaphragm and plunger in accordance with another aspect of the present disclosure.

FIG. 35 is a cross-sectional side view of a rolling diaphragm 112 and plunger 144 in accordance with another aspect of the present disclosure. The plunger 144 has a first end 144a and a second end 144b where the first end 144a is movable axially relative to the second end 144b. The first and second ends 144a, 144b are connected together by webbing 144c extending obliquely to a longitudinal axis of the plunger 144. Upon movement of the first end 144a toward the second end 144b, the webbing 144c expands radially outwardly to engage the sidewall 134 of the rolling diaphragm 112 allowing retraction of the inwardly facing wall of the empty rolling diaphragm 112. Upon movement of the first end 144a away from the second end 144b, the webbing 144c contracts radially inwardly to disengage from the sidewall 134 of the rolling diaphragm 112.

Figure 36A:
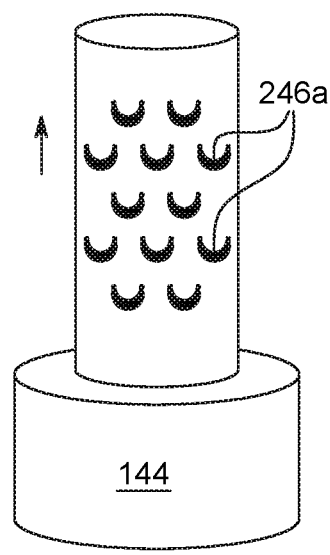
FIG. 36A is a perspective view of a plunger in accordance with another aspect of the present disclosure.
Figure 36B:
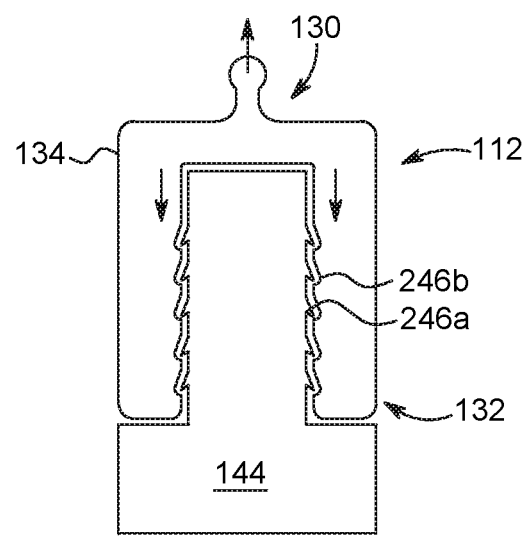
FIG. 36B is a cross-sectional side view of the plunger shown in FIG. 36A and a rolling diaphragm.
Figure 43:
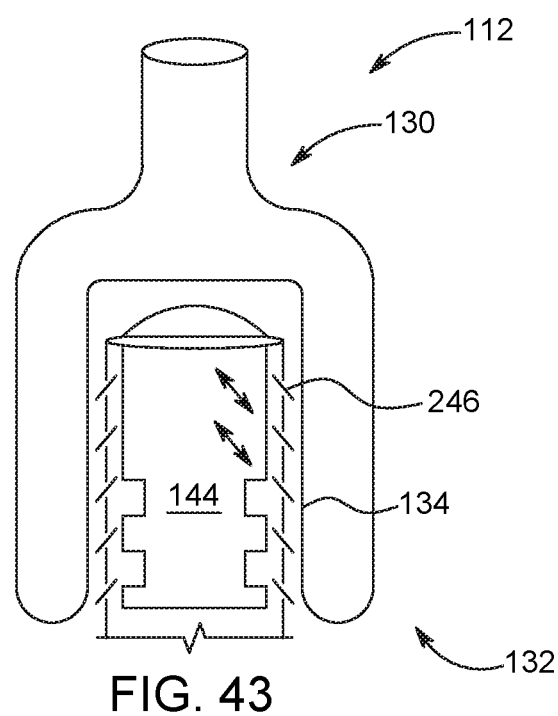
FIG. 43 is a cross-sectional side view of a rolling diaphragm and plunger in accordance with another aspect of the present disclosure.

FIG. 36A is a perspective view of a plunger 144 in accordance with another aspect of the present disclosure. FIG. 36B is a cross-sectional side view of the plunger 144 shown in FIG. 36A and a rolling diaphragm 112. The plunger 144 has one or more first gripping elements 246a protruding radially outward relative to a body of the plunger 144. In some aspects, the one or more first gripping elements 246a may have a first end connected to the body of the plunger 144 and a second end protruding radially outward relative to the first end. At least one of the one or more first gripping elements 246a may be configured for engaging a smooth sidewall 134 of the rolling diaphragm 112 (not shown). In other aspects shown in FIG. 36B, at least one of the one or more first gripping elements 246a on the plunger 144 may be configured for engaging corresponding second gripping elements 246b formed on the sidewall 134 of the rolling diaphragm 112. The interaction between the first gripping elements 246a and the second gripping elements 246b increases the gripping force at the interface between the plunger 144 and the sidewall 134 of the rolling diaphragm 112. The one or more gripping elements may be active gripping elements that are engaged (by radial extension) or disengaged (by radial retraction) relative to the body of the plunger 144, such as shown in FIG. 43. In some aspects, at least one of the first gripping elements 246a and the second gripping elements 246b may be angled relative to a longitudinal axis of the plunger 144 and the rolling diaphragm 112 to prevent unintended disengagement during proximal movement of the plunger 144.

Figure 37:
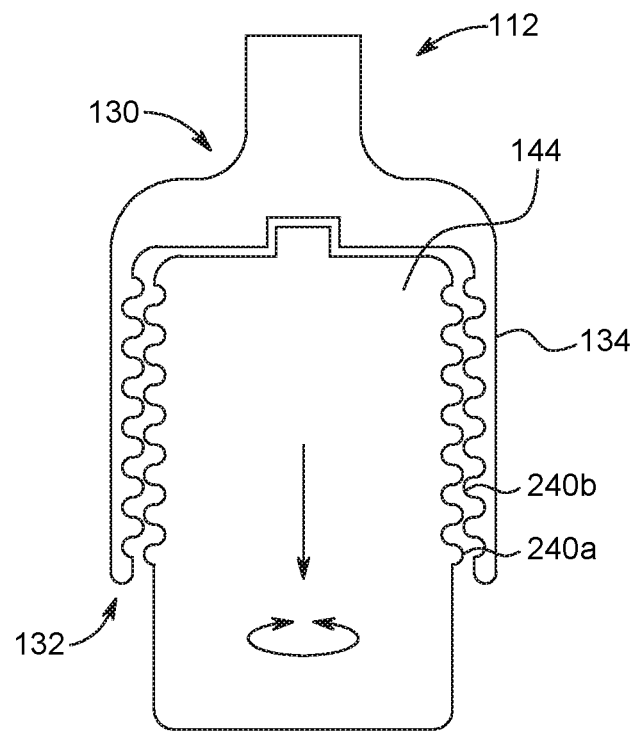
FIG. 37 is a cross-sectional side view of a rolling diaphragm and plunger in accordance with another aspect of the present disclosure.

FIG. 37 is a cross-sectional side view of a rolling diaphragm 112 and plunger 144 in accordance with another aspect of the present disclosure. The plunger 144 has a first threaded portion 240a, while an inwardly facing outer portion of the sidewall 134 of the rolling diaphragm 112 has a second threaded portion 240b that can be threadably engaged with the first threaded portion 240a of the plunger 144. In some aspects, the plunger 144 may be rotated about its longitudinal axis and move linearly along the longitudinal axis to allow the first threaded portion 240a to engage with the second threaded portion 240b. Once engaged, the plunger 144 can be moved withdrawn axially without rotation. The threaded engagement between the first threaded portion 240a and the second threaded portion 240b assists in increasing the gripping force of the plunger 144 against the sidewall 134 of the rolling diaphragm 112 as the rolling diaphragm 112 is drawn from a collapsed configuration in a proximal direction to fill the interior volume 114 of the rolling diaphragm 112 with fluid. In some aspects, at least one of first threaded portion 240a and the second threaded portion 240b may be discontinuous around at least a portion of the circumference of the piston 144 and sidewall 134 of the rolling diaphragm 112, respectively. In other aspects, the first threaded portion 240a and the second threaded portion 240b may extend helically about the longitudinal axis of the plunger 144 and the rolling diaphragm 112, respectively. In further aspects, the first threaded portion 240a and the second threaded portion 240b may be formed as a plurality of circular ridges on one of the plunger 144 and the rolling diaphragm 112 and corresponding circular grooves on the other of the plunger 144 and the rolling diaphragm 112.

Figure 38:
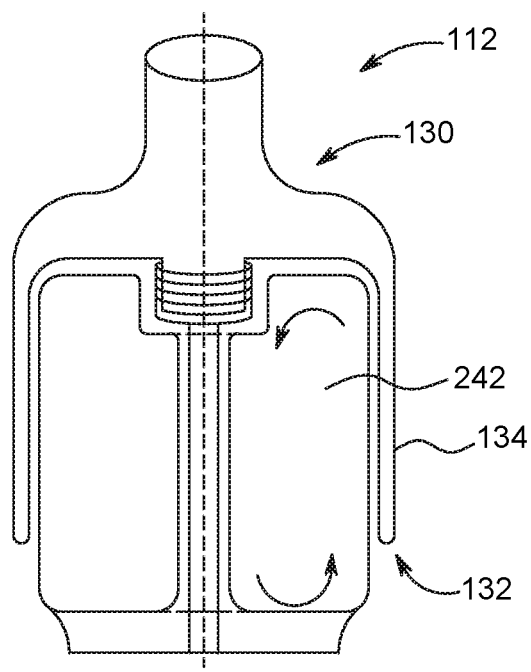
FIG. 38 is a cross-sectional side view of a rolling diaphragm and plunger in accordance with another aspect of the present disclosure.

FIG. 38 is a cross-sectional side view of a rolling diaphragm and plunger in accordance with another aspect of the present disclosure. An annular member 242 may be disposed between a folded inwardly facing portion of the sidewall 134 of the rolling diaphragm 112 and the plunger 144. The annular member 242 may be pressurized to expand against the sidewall 134 of the rolling diaphragm 112 to prevent bending and buckling of the sidewall 134 when the plunger 144 is withdrawn in a proximal direction. In certain embodiments, the annular member 242 can roll upon itself in a manner similar to the rolling of the rolling diaphragm 112 described herein.

Figure 39A:
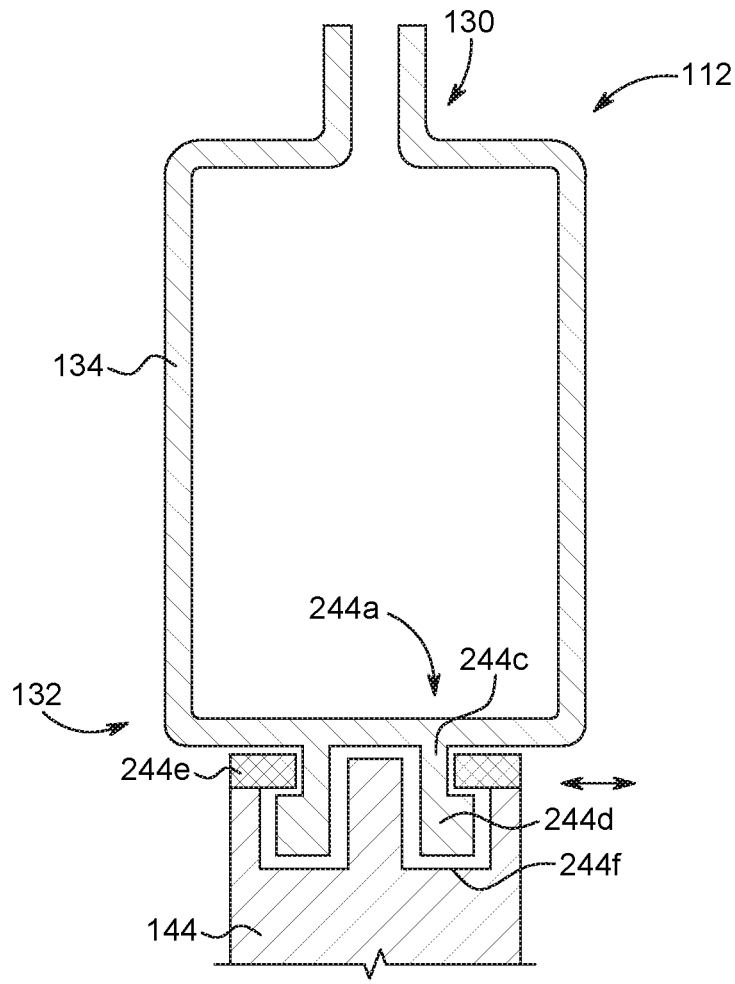
FIG. 39A is a cross-sectional side view of a rolling diaphragm and plunger in accordance with another aspect of the present disclosure, with the plunger shown in a first axial position.
Figure 39B:
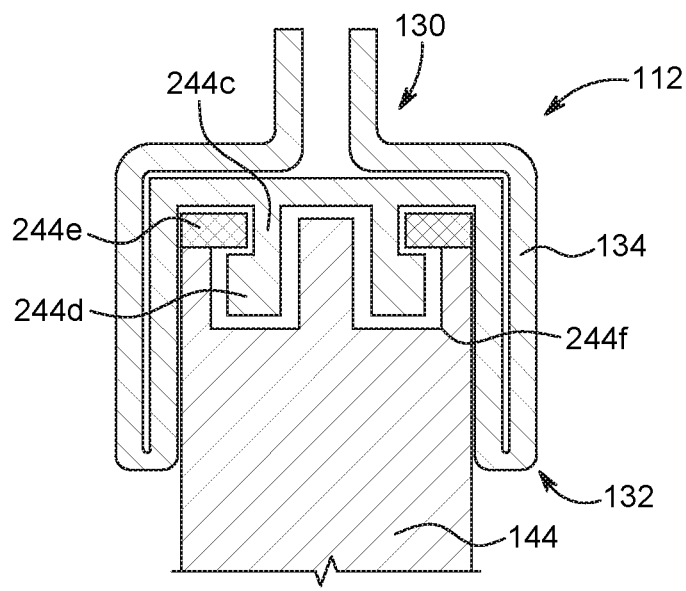
FIG. 39B is a cross-sectional side view of the rolling diaphragm and plunger shown in FIG. 39A, with the plunger shown in a second axial position.

FIG. 39A is a cross-sectional side view of a rolling diaphragm 112 and plunger 144 in accordance with another aspect of the present disclosure, with the plunger 144 shown in a first axial position. FIG. 39B is a cross-sectional side view of the rolling diaphragm 112 and plunger 144 shown in FIG. 39A, with the plunger 144 shown in a second axial position. The rolling diaphragm 112 has a first engagement portion 244a formed at the proximal end 132 of the rolling diaphragm 112. The first engagement portion 244a is configured for engagement with the plunger 144. In some aspects, the first engagement portion 244a is formed as one or more legs 244c extending proximally from a central portion of the proximal end 132. Each of the legs 244c has a radially-extending ledge 244d at a proximal end thereof. The first engagement portion 244a is connectable to a second engagement portion 244b formed on the plunger 144. The second engagement portion 244b may be formed as a recess configured to receive the leg 244c and the ledge 244d of the first engagement portion 244a. In some aspects, the first engagement portion 244a may be releasably connected to the second engagement portion 244b. For example, the second engagement portion 244b on the plunger 144 may have a movable locking element 244e that is movable to selectively lock the first engagement portion 244a of the rolling diaphragm 112. In some aspects, the locking element 244e may be movable linearly in a radial direction to allow the leg 244c and the ledge 244d to be withdrawn from the recess of the second engagement portion 244b. In other aspects, the locking element 244e may be pivotable about a pivot point between a locked position, in which the leg 244c and the ledge 244d are locked within the recess of the second engagement portion 244b, and an unlocked position, in which the leg 244c and the ledge 244d can be withdrawn from the recess of the second engagement portion 244b. Once connected, the first engagement portion 244a and the second engagement portion 244b allow the plunger 144 to reciprocally move to allow filling or discharging the rolling diaphragm 112. In some aspects, the first engagement portion 244a and the second engagement portion 244b may be connected by way of a bayonet connection by rotating one of the first engagement portion 244a and the second engagement portion 244b relative to the other of the first engagement portion 244a and the second engagement portion 244b.

Figure 41A:
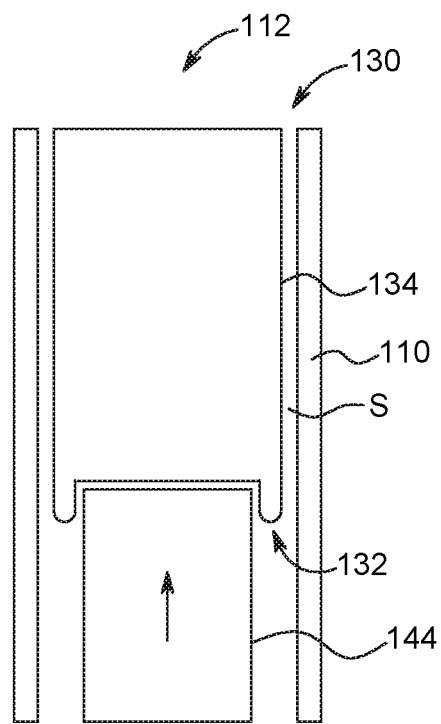
FIG. 41A is a cross-sectional side view of a rolling diaphragm and plunger in accordance with another aspect of the present disclosure, with the plunger shown in a first axial position.
Figure 41B:
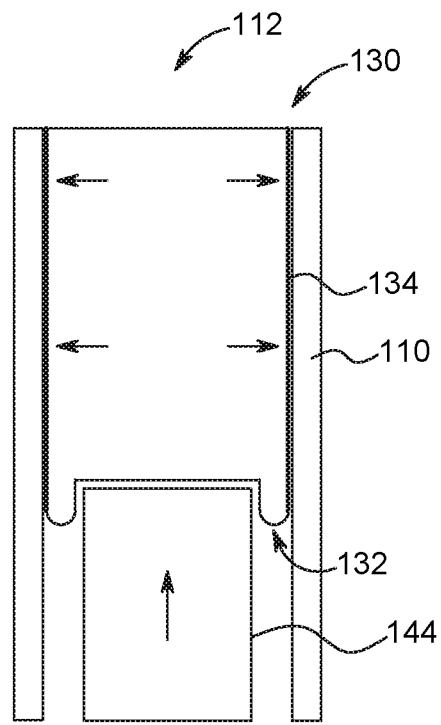
FIG. 41B is a cross-sectional side view of the rolling diaphragm and plunger shown in FIG. 41A, with the plunger shown in a second axial position.
Figure 41C:
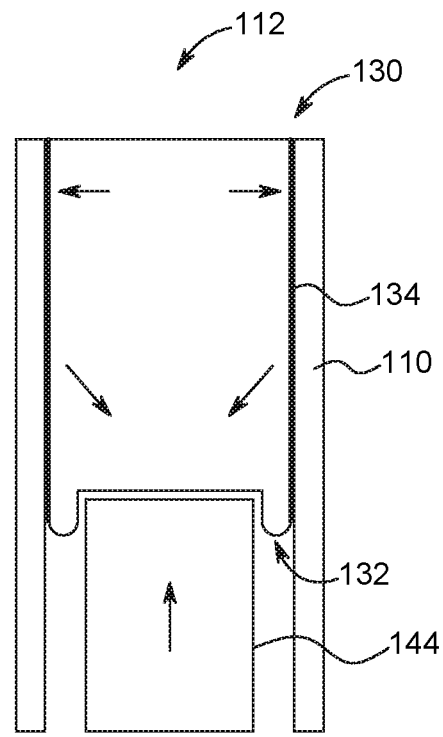
FIG. 41C is a cross-sectional side view of the rolling diaphragm and plunger shown in FIG. 41A, with the plunger shown in a third axial position.

FIG. 41A is a cross-sectional side view of a rolling diaphragm 112 and plunger 144 in accordance with another aspect of the present disclosure, with the plunger 144 shown in a first axial position. FIGS. 41B-42C are cross-sectional side views of the rolling diaphragm 112 and plunger 144 shown in FIG. 41A, with the plunger 144 shown in second and third axial positions, respectively. The rolling diaphragm 112 is disposed within a pressure jacket 110 that has an inner diameter that is larger than an outer diameter of an uncompressed rolling diaphragm 112 such that a space S is created between the inner sidewall of the pressure jacket 110 and the outer portion of the sidewall 134 of the rolling diaphragm 112. As the plunger 144 is advanced toward the distal end 130 of the rolling diaphragm 112, the sidewall 134 of the rolling diaphragm 112 is compressed, causing the sidewall 134 to expand radially outward and engage the inner sidewall of the pressure jacket 110. Desirably, the rolling diaphragm 112 is used with a high crack-pressure valve that prevents fluid from being delivered from the interior volume 114 of the rolling diaphragm 112 until a predetermined pressure is reached at the outlet of the rolling diaphragm 112 or within a tubing set (not shown). Further movement of the plunger 144 in the distal direction further compresses the sidewall 134 of the rolling diaphragm 112 to increase the total strain on the sidewall 134 while remaining within its elastic limits.

Figure 42:
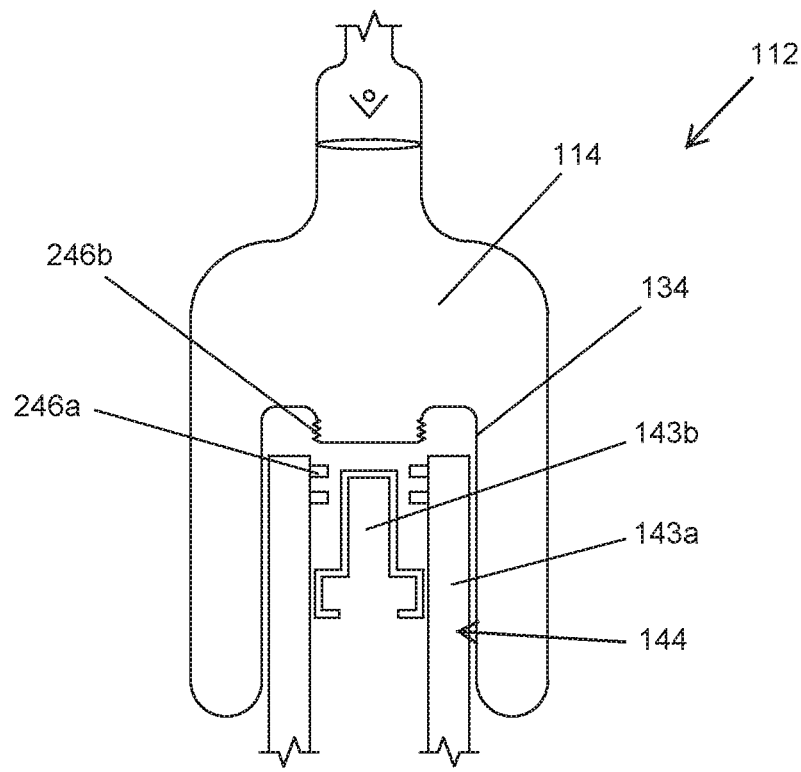
FIG. 42 is a cross-sectional side view of a rolling diaphragm and plunger in accordance with another aspect of the present disclosure.

FIG. 42 is a cross-sectional side view of a rolling diaphragm 112 and plunger 144 in accordance with another aspect of the present disclosure. The plunger 144 has an outer portion 143a that is reciprocally movable to engage an inner portion of the sidewall 134 of the rolling diaphragm 112, as described herein. The plunger 144 further has an inner portion 143b that is independently movable relative to the outer portion 143a. The outer portion 143a is moved distally until the outer portion 143a contacts the sidewall 134 of the rolling diaphragm 112. Subsequently, the inner portion 143b is advanced distally to compress the sidewall 134 of the rolling diaphragm 112 to deliver fluid from the interior volume 114 of the rolling diaphragm 112. The inner portion 143b is then retracted proximally, while the outer portion 143a is moved distally. The movement of the inner portion 143b to expel fluid from the interior volume 114 of the rolling diaphragm 112 may be performed in a sequential manner. The plunger 144 has one or more first gripping elements 246a protruding radially inward relative to the outer portion 143a. At least one of the one or more first gripping elements 246a on the plunger 144 may be configured for engaging corresponding second gripping elements 246b formed on the sidewall 134 of the rolling diaphragm 112. The interaction between the first gripping elements 246a and the second gripping elements 246b increases the gripping force at the interface between the plunger 144 and the sidewall 134 of the rolling diaphragm 112.

Figure 44:
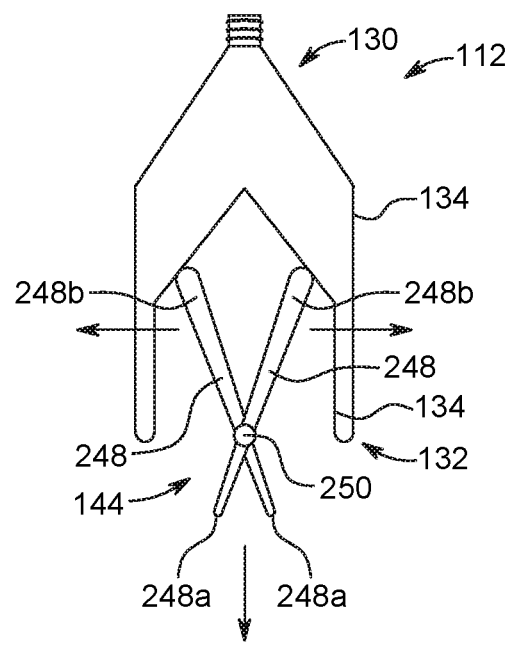
FIG. 44 is a cross-sectional side view of a rolling diaphragm and plunger in accordance with another aspect of the present disclosure.
Figure 45:
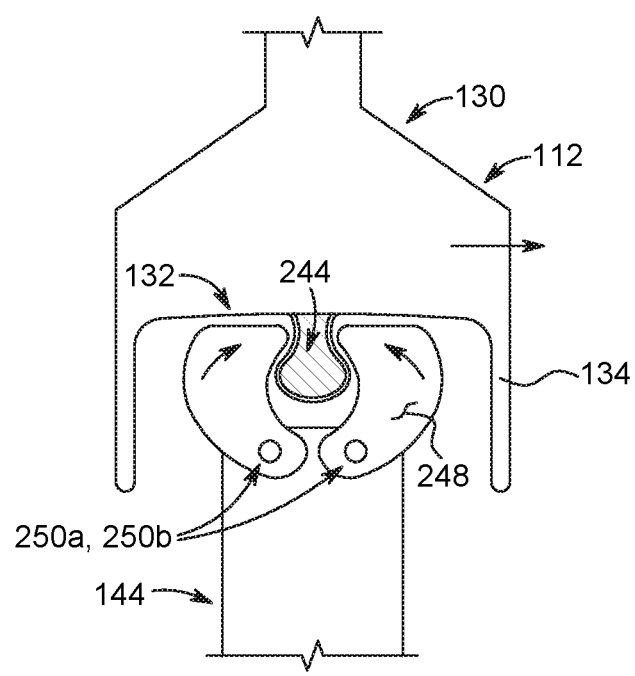
FIG. 45 is a cross-sectional side view of a rolling diaphragm and plunger in accordance with another aspect of the present disclosure.

FIG. 44 is a cross-sectional side view of a rolling diaphragm 112 and plunger 144 in accordance with another aspect of the present disclosure. The plunger 144 has a pair of pivotable elements 248 that are pivotable around a common pivot point 250. By moving proximal ends 248a of the pivotable elements 248 toward each other, the distal ends 248b are moved away from each other and into engagement with the sidewall 134 of the rolling diaphragm 112. Conversely, by moving the proximal ends 248a of the pivotable elements 248 away from each other, the distal ends 248b are moved toward each other and out of engagement with the sidewall 134 of the rolling diaphragm 112. In FIG. 45, the pivotable elements 248 are pivotable about first and second pivot points 250a, 250b. The pivotable elements 248 are pivotable radially inward into engagement with an engagement portion 244 protruding from the proximal end 132 of the rolling diaphragm 112. In certain embodiments, first and second pivot points 250a, 250b may be the same.

Figure 46A:
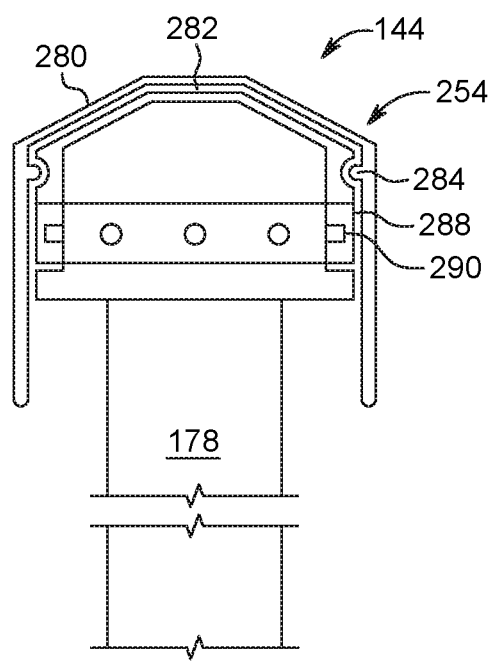
FIG. 46A is a cross-sectional side view of a plunger in accordance with another aspect of the present disclosure.
Figure 46B:
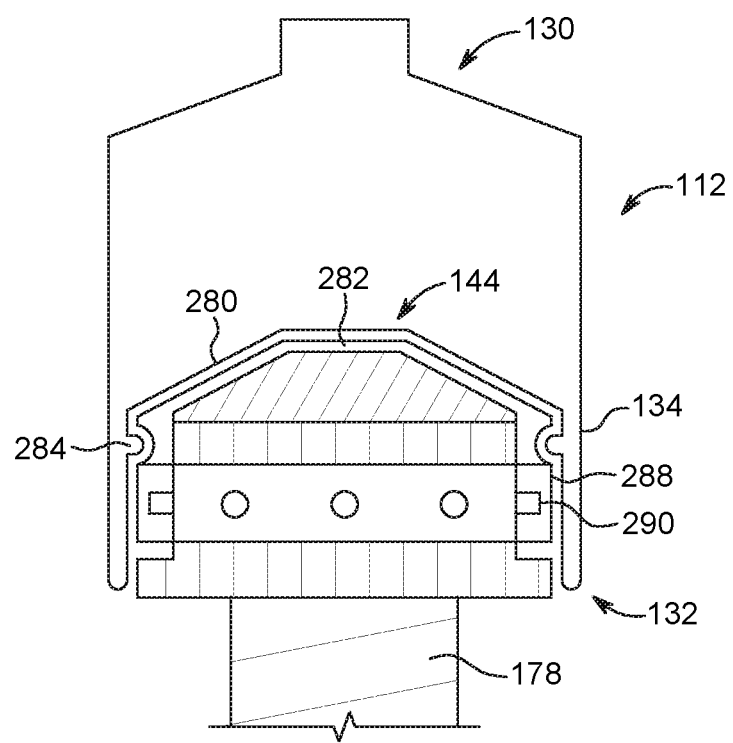
FIG. 46B is a cross-sectional side view of a rolling diaphragm and the plunger shown in FIG. 46A.

FIG. 46A is a cross-sectional side view of a plunger 144 in accordance with another aspect of the present disclosure. FIG. 46B is a cross-sectional side view of a rolling diaphragm 112 and the plunger 144 shown in FIG. 46A. The plunger 144 has a connection interface 254 configured for engagement with a piston 178 having connection features described in U.S. Pat. No. 5,383,858 to Reilly et al.; U.S. Pat. No. 5,873,861 to Hitchins et al.; and U.S. Pat. No. 6,652,489 to Trocki et al., which are incorporated herein by reference in their entirety. The piston 178 has at least one attachment member adapted to releasably engage the plunger 144 regardless of the orientation of the plunger 144 about its longitudinal axis with respect to the piston 178. In some aspects, the plunger 144 has a cover 280 that covers at least a portion of the body of the plunger 144. The cover 280 is retained with the body 282 by way of a lip 284 that engages a groove 286 on the body 282. The body 282 further has an annular ridge 288 that receives one or more pins 290 that are reversibly extendable from the piston 178. When the one or more pins 290 extend radially outward from the piston 178, at least one of the pins 290 is received inside the annular ridge 288. In this manner, proximal or distal movement of the piston 178 results in a corresponding movement of the plunger 144 as a result of engagement of at least one of the pins 290 within the annular ridge 288. Retracting the one or more pins 290 in a radially inward direction releases the one or more pins 290 from the annular ridge 288 to allow the piston 178 to be released from the plunger 144.

Figure 47A:
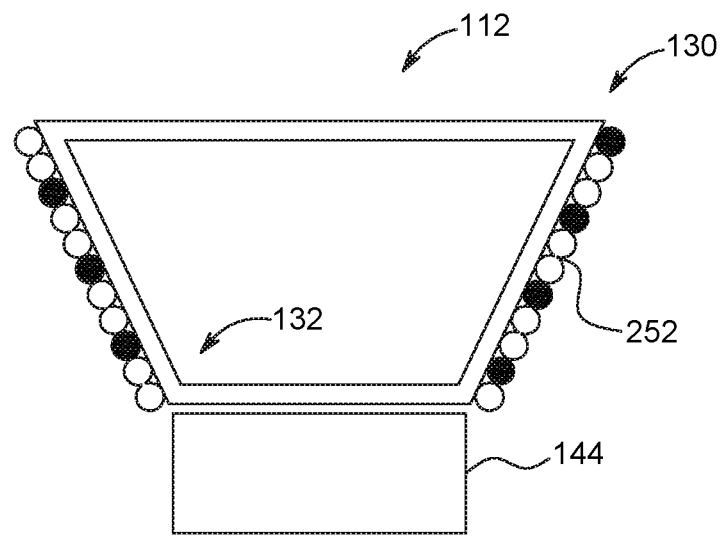
FIG. 47A is a cross-sectional side view of a rolling diaphragm and plunger in accordance with another aspect of the present disclosure, with the plunger shown in a first axial position.
Figure 47B:
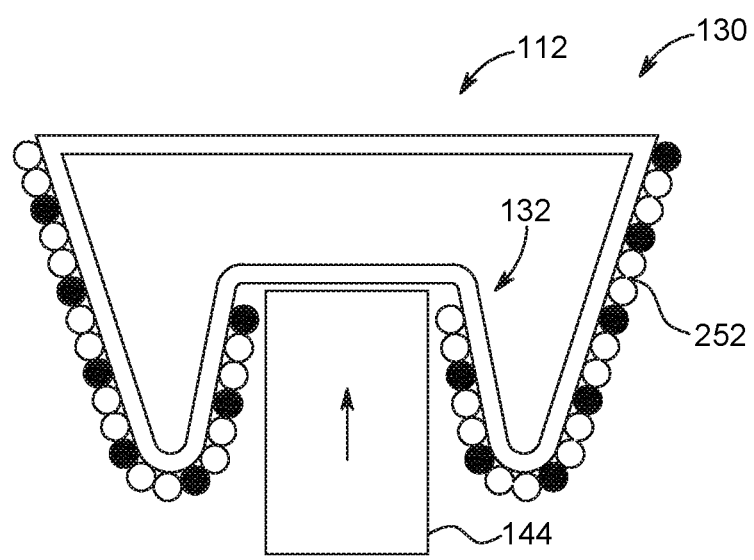
FIG. 47B is a cross-sectional side view of the rolling diaphragm and plunger shown in FIG. 47A, with the plunger shown in a second axial position.

FIG. 47A is a cross-sectional side view of a rolling diaphragm 112 and plunger 144 in accordance with another aspect of the present disclosure, with the plunger 144 shown in a first axial position. FIG. 47B is a cross-sectional side view of the rolling diaphragm 112 and plunger 144 shown in FIG. 47A, with the plunger 144 shown in a second axial position. The rolling diaphragm 112 has a conical shape that extends radially outward from the proximal end 132 toward the distal end 130. An outer circumference of the sidewall 134 has an elastic element 252, such as a spring, coiled around the sidewall 134 and extending between the proximal end 132 and the distal end 130. The elastic element 252 is configured to roll upon itself in a manner similar to the rolling over of the sidewall 134 of the rolling diaphragm 112 upon engagement with the plunger 144. In some aspects, the elastic element 252 may be a reinforced elastomer spring, or a metal mesh.

Figure 48A:
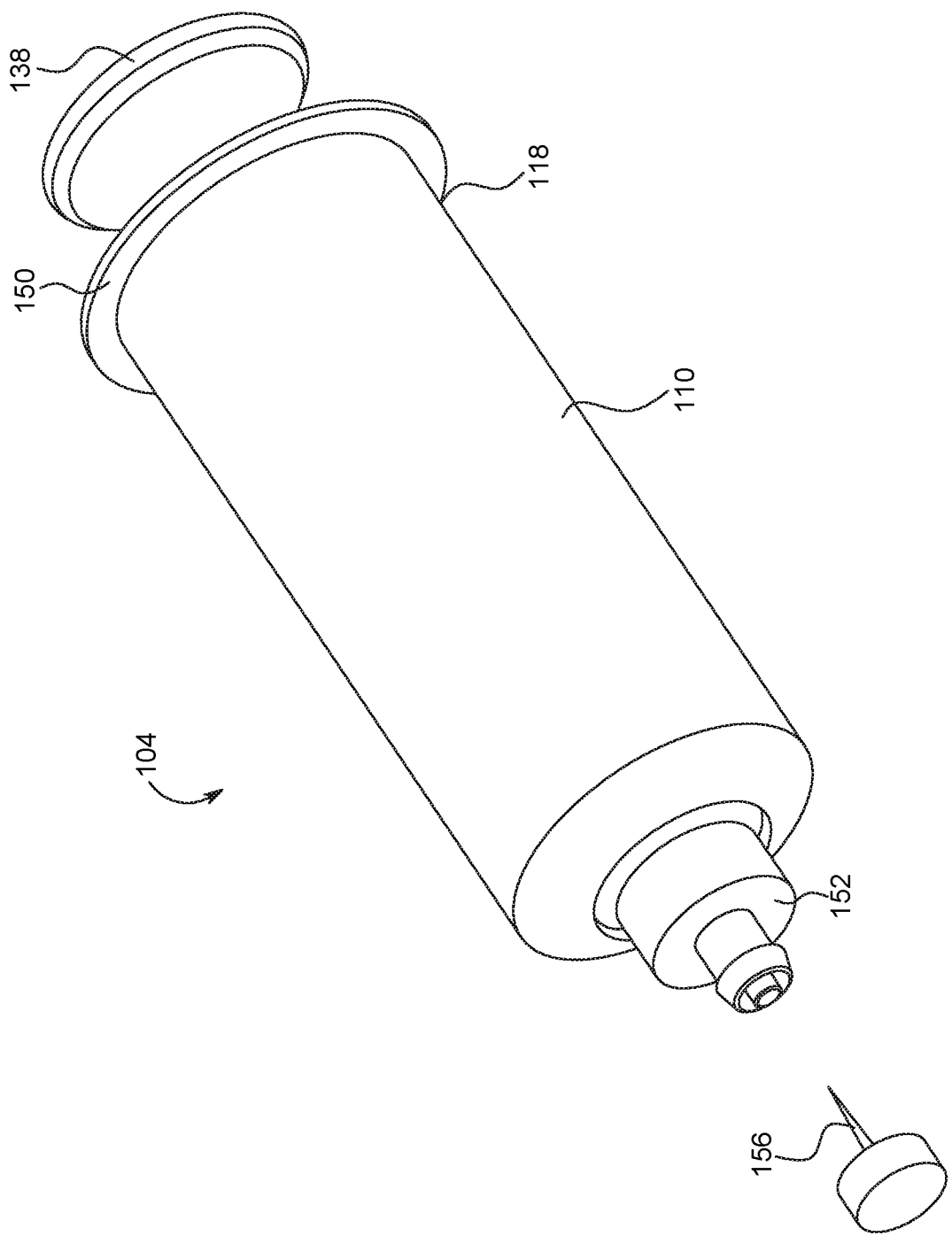
FIG. 48A is a partially-exploded perspective view of a syringe having a pressure jacket, a rolling diaphragm, and plunger in accordance with another aspect of the present disclosure.
Figure 48B:
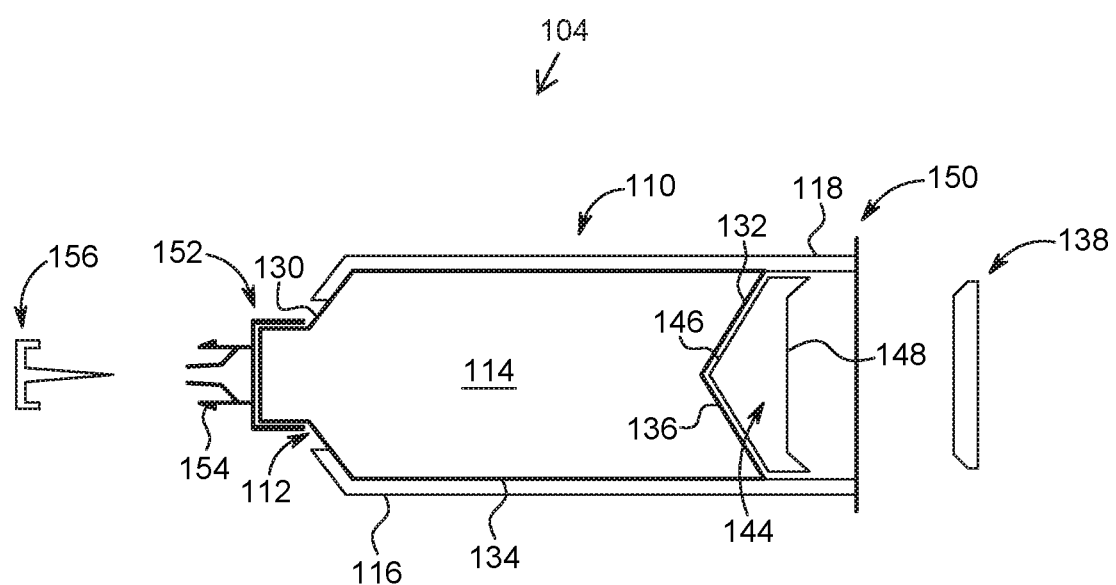
FIG. 48B is a cross-sectional side view of the syringe shown in FIG. 48A.

FIG. 48A is a partially-exploded perspective view of a syringe having a pressure jacket 110, a rolling diaphragm 112, and plunger 144 in accordance with another aspect of the present disclosure. FIG. 48B is a cross-sectional side view of the syringe shown in FIG. 48A. The components of the syringe 104 shown in FIGS. 48A-48B are substantially similar to the components of the syringe 104 described above with reference to FIGS. 2-3. Reference numerals in FIGS. 48A-48B are used to illustrate identical components as the corresponding reference numerals in FIGS. 2-3. As the previous discussion regarding the syringe 104 generally shown in FIGS. 2-3 is applicable to the aspect shown in FIGS. 48A-48B, only the relevant differences between these systems are discussed hereinafter.

FIGS. 48A-48B illustrate a disposable, single-use syringe 104 that is prefilled with a fluid for delivery to a patient. The syringe 104 includes a disposable pressure jacket 110 that interfaces with the injector 102, as described above with reference to FIG. 2. The proximal end 118 of the pressure jacket 110 has a plunger 144 that engages the end wall 136 of the rolling diaphragm 112. The plunger 144 has a distal end 146 that engages the end wall 136 of the rolling diaphragm 112 and a proximal end 148 that is shaped to engage the piston head 138 of the injector 102. The proximal end 118 of the pressure jacket 110 is provided with a seal 150. The seal 150 seals the proximal end 118 of the pressure jacket 110 prior to use with the injector 102 (not shown in FIGS. 48A-48B). Additionally, the seal 150 provides a vapor barrier. Desirably, the seal 150 is removed prior to connecting the syringe 104 to the injector 102. The syringe 104 further includes a cap 152 provided at the distal end 130 of the rolling diaphragm 112. The cap 152 may be molded, adhered, screwed, or otherwise mechanically coupled to the distal end 130 of the rolling diaphragm 112. Desirably, the connection between the cap 152 and the distal end 130 of the rolling diaphragm 112 is formed to withstand typical injection pressures. The cap 152 has a connector 154, such as a luer-type connector, for connecting to a fluid path set (not shown). In one aspect, the fluid path set includes a corresponding connector for coupling to the connector 154 on the cap 152. A piercing needle 156 is provided, for example, on the fluid path set to allow piercing of the cap 152 and the discharge port 142 of the rolling diaphragm 112 to fluidly connect the interior volume 114 of the rolling diaphragm 112 with the fluid path set. Desirably, the fluid path set is disposed with the rolling diaphragm 112 after use.

Figure 49A:
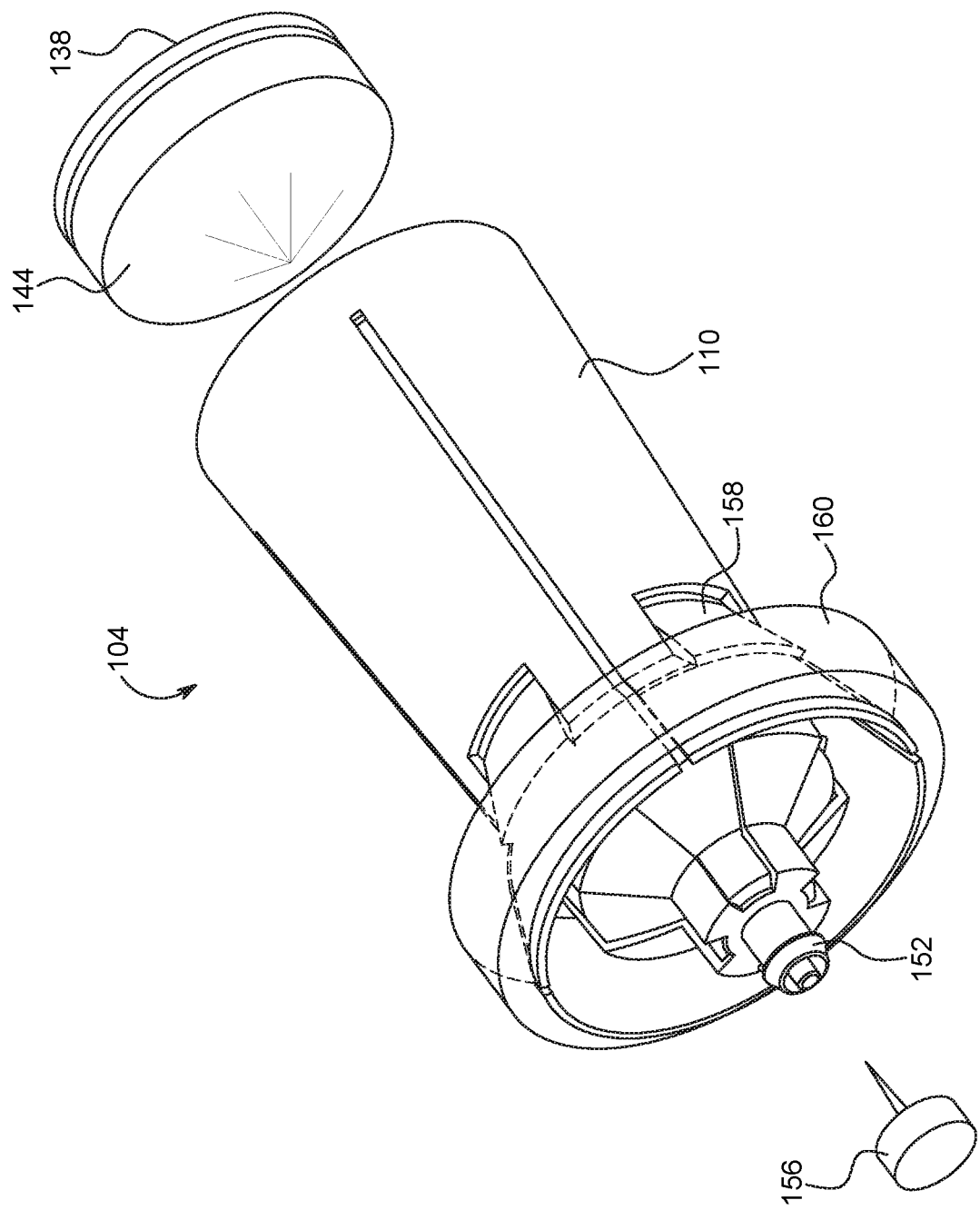
FIG. 49A is a partially-exploded perspective view of a syringe having a pressure jacket, a rolling diaphragm, and plunger in accordance with another aspect of the present disclosure.
Figure 49B:
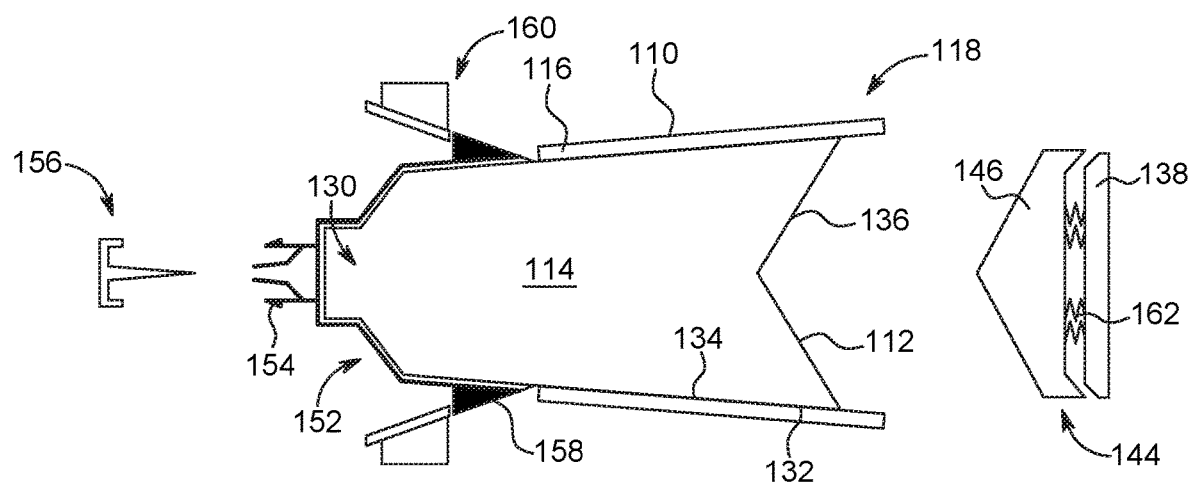
FIG. 49B is a cross-sectional side view of the syringe shown in FIG. 49A.

FIG. 49A is a partially-exploded perspective view of a syringe 104 having a pressure jacket 110, a rolling diaphragm 112, and plunger 144 in accordance with another aspect of the present disclosure. FIG. 49B is a cross-sectional side view of the syringe 104 shown in FIG. 49A.

The components of the syringe 104 shown in FIGS. 49A-49B are substantially similar to the components of the syringe 104 described above with reference to FIGS. 48A-48B. Reference numerals in FIGS. 49A-49B are used to illustrate identical components as the corresponding reference numerals in FIGS. 48A-48B. As the previous discussion regarding the syringe 104 generally shown in FIGS. 48A-48B is applicable to the aspect shown in FIGS. 49A-49B, only the relevant differences between these systems are discussed hereinafter. The pressure jacket 110 may be a reusable pressure jacket 110 that may be used with different rolling diaphragms 112. Desirably, the pressure jacket 110 is substantially conical and is removably connectable to the injector 102 to extend at least along a portion of the sidewall 134 of the rolling diaphragm 112. The rolling diaphragm 112 can be loaded from the distal end 116 of the pressure jacket 110. The cap 152 is formed such that it extends from the distal end 130 of the rolling diaphragm 112 to at least a portion of the sidewall 134. The cap 152 includes at least one locking tab 158 that extends radially outward from an outer surface of the cap 152. The locking tab 158 is formed to engage a locking collar 160 provided on the injector 102. The locking collar 160 is retractable such that it can be engaged with the locking tab 158 during use and disconnected therefrom when the rolling diaphragm 112 is to be removed from the pressure jacket 110. The plunger 144 is reusable and expands radially with axial movement in a distal direction along the axis of the pressure jacket 110. The plunger 144 may be spring-loaded against the piston head 138 by one or more springs 162. Upon withdrawal of the piston head 138 in the proximal direction, the springs 162 push the plunger 144 apart from the piston head 138 to allow for the diameter of the plunger 144 to be reduced as it is withdrawn in the proximal direction. In one aspect, the used rolling diaphragm 112 may be removed from the pressure jacket 110 by a removal member, such as a burst of compressed air or an action of a mechanical piston that crushes the rolling diaphragm 112 to a compact size for easy disposal.

Figure 50A:
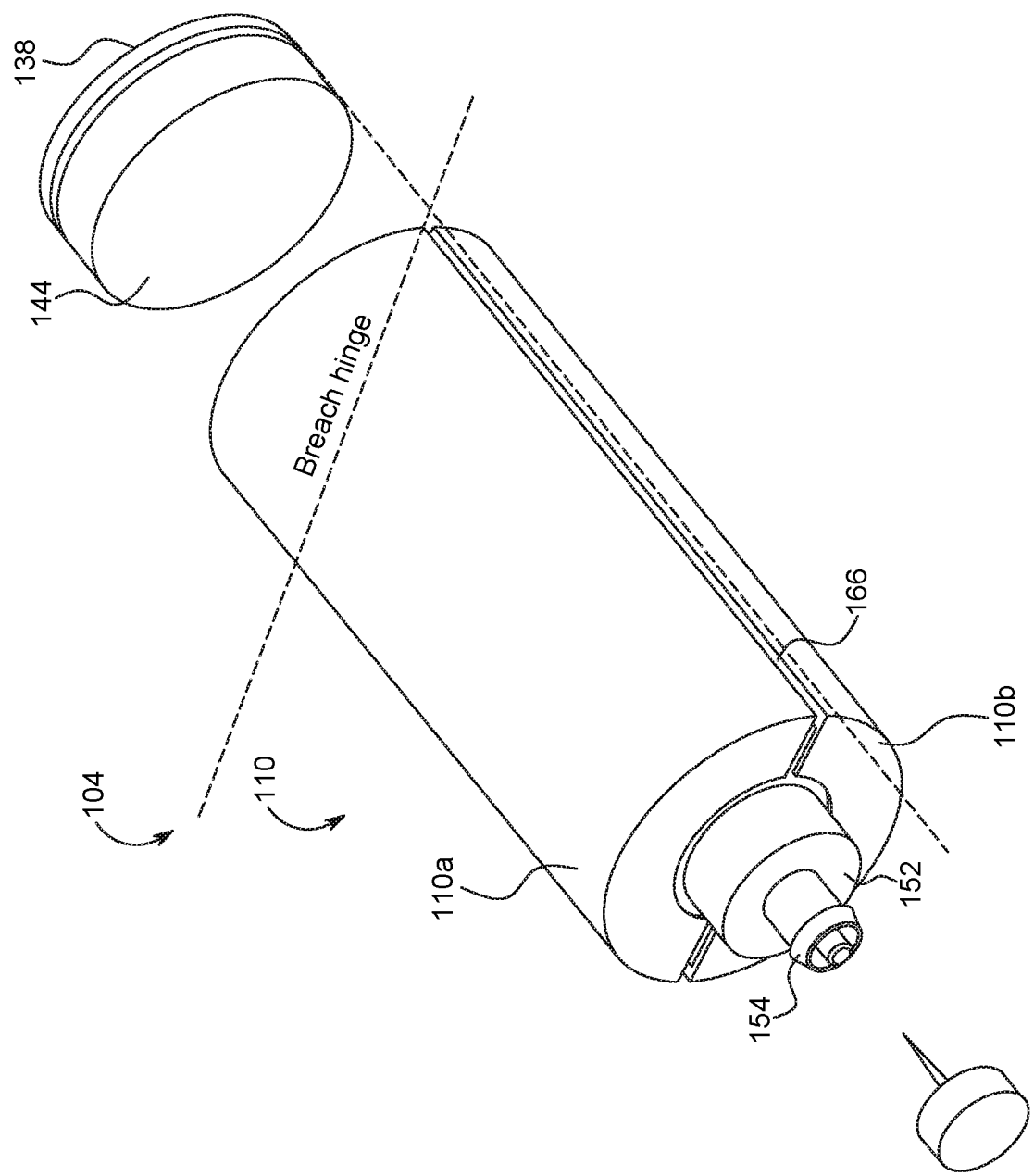
FIG. 50A is a partially-exploded perspective view of a syringe having a pressure jacket, a rolling diaphragm, and plunger in accordance with another aspect of the present disclosure.
Figure 50B:
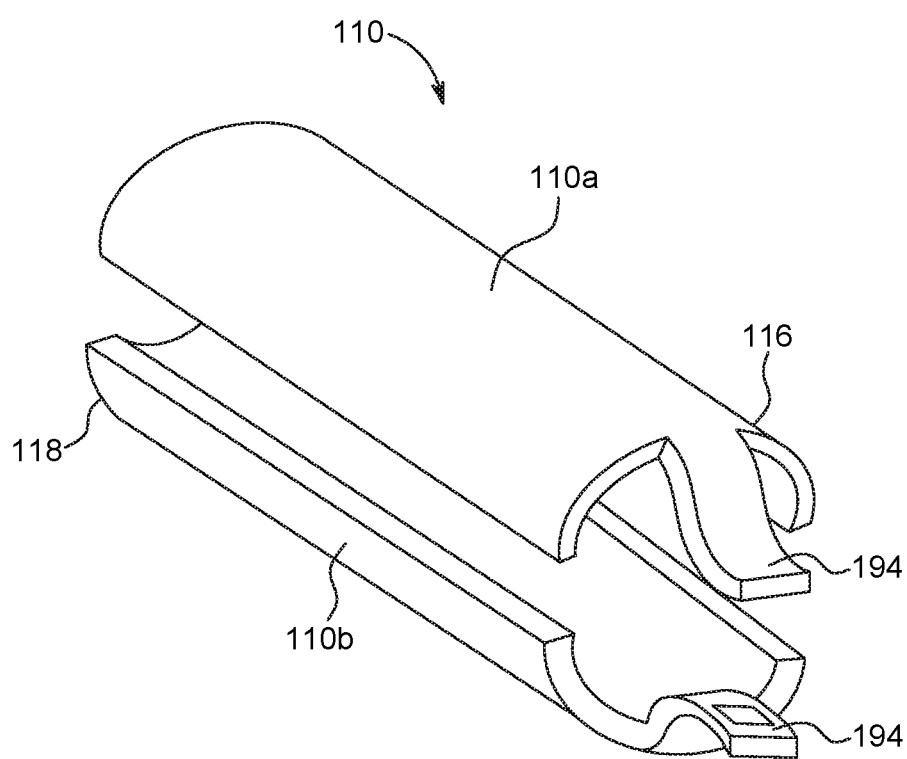
FIG. 50B is a perspective view of a pressure jacket for use with a syringe.

FIG. 50A is a partially-exploded perspective view of a syringe 104 having a pressure jacket 110, a rolling diaphragm 112 (not shown, within pressure jacket 110), and plunger 144 in accordance with another aspect of the present disclosure. In some aspects, the pressure jacket 110 is formed from two cylindrical halves 110a, 110b which are hingedly connected together. A hinge 166 may be provided substantially parallel with the longitudinal axis of the pressure jacket 110, or a hinge 104 may be provided at the proximal end 118 or distal end 116 and substantially perpendicular relative to the longitudinal axis. The pressure jacket 110 may be opened by pivoting one of the cylindrical halves 110a, 110b relative to the other by action of the hinge to open pressure jacket 110 and allow for easier loading of the rolling diaphragm. Once loaded, the pressure jacket 110 may be closed before being connected to the injector 102. With reference to FIG. 50B, a pressure jacket 110 is shown in accordance with another aspect. In this aspect, the pressure jacket 110 is formed from two cylindrical halves 110a, 110b which are joined together in a clam-shell configuration. A finger lock 194 is provided at the distal end 116 of the pressure jacket 110. The pressure jacket 110 may be opened by swinging one of the cylindrical halves 110a, 110b relative to the other to allow for easier loading of the rolling diaphragm 112. Once loaded, the pressure jacket 110 may be closed before being connected to the injector 102 (not shown).

Figure 51:
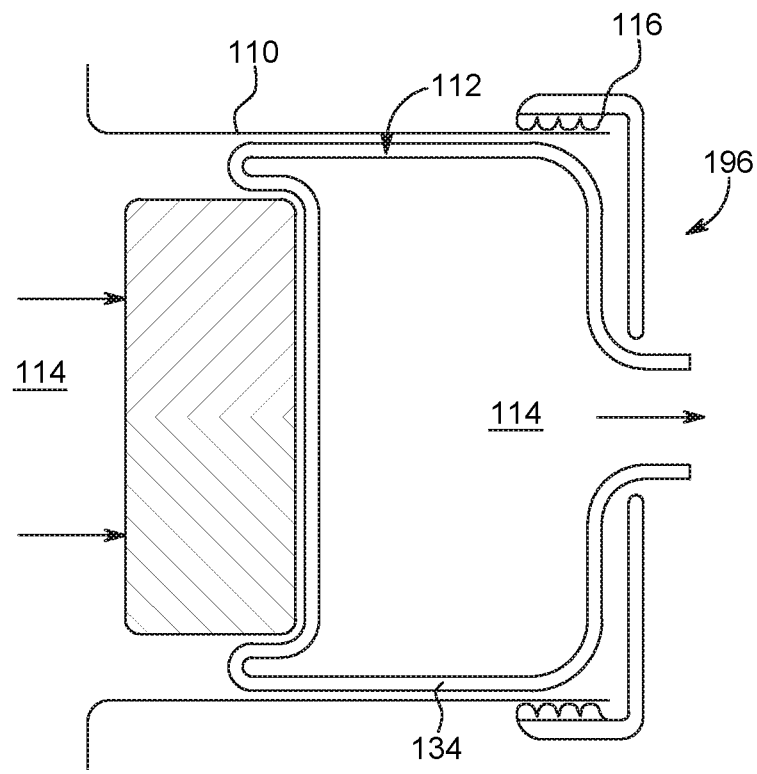
FIG. 51 is a cross-sectional side view of a syringe having a pressure jacket, a rolling diaphragm, and plunger in accordance with another aspect of the present disclosure.

FIG. 51 is a cross-sectional side view of a syringe 104 having a pressure jacket 110, a rolling diaphragm 112, and plunger 144 in accordance with another aspect of the present disclosure. The pressure jacket 110 has a removable closure 196 for enclosing the distal end 116 of the pressure jacket 110. The closure 196 may be removable from the distal end 116 of the pressure jacket 110 for loading the rolling diaphragm 112 into the pressure jacket 110. Once the rolling diaphragm 112 is loaded, the distal end 116 of the pressure jacket 110 is closed by the closure 196. For example, the closure 196 may have internal or external threads that engage the corresponding threads on the distal end 116 of the pressure jacket 110. Alternatively, the closure 196 may be a bayonet-type closure having tabs or slots that engage with corresponding slots or tabs on the distal end 116 of pressure jacket 110. The closure 196 may have a threaded fitting for connecting to the fluid path set (not shown).

Figure 52A:
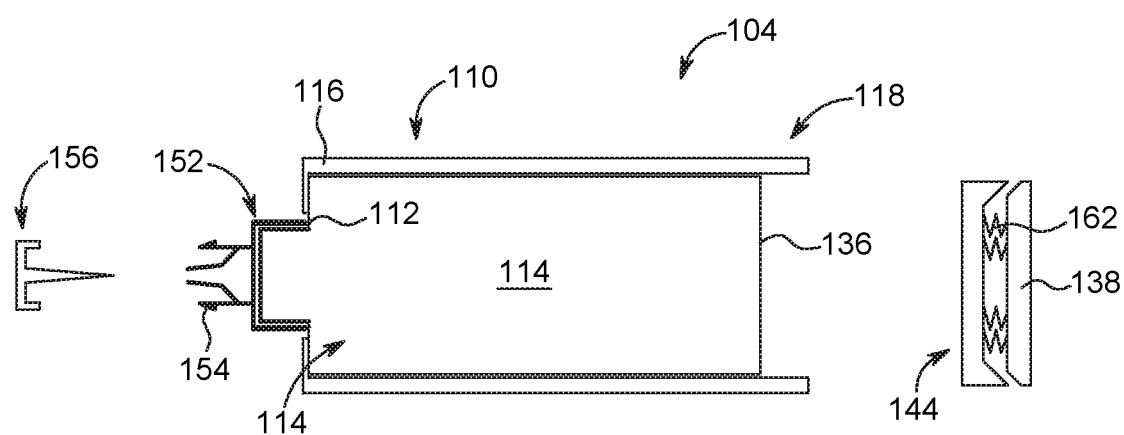
FIG. 52A is a partially-exploded side cross-sectional view of a syringe having a pressure jacket, a rolling diaphragm, and plunger in accordance with another aspect of the present disclosure.
Figure 52B:
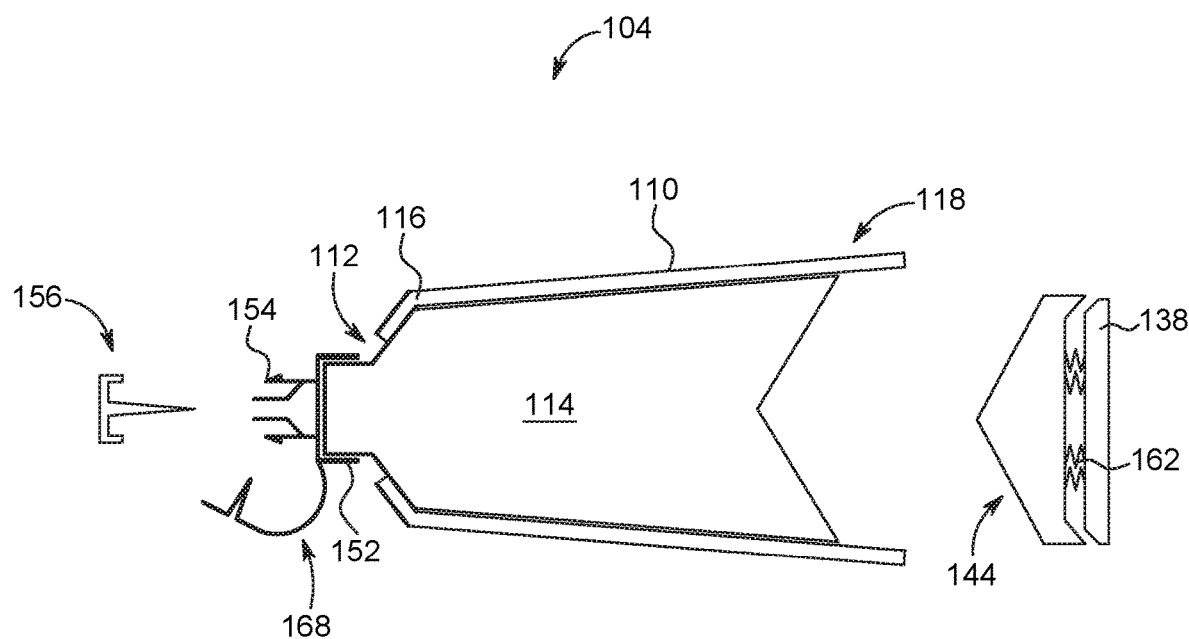
FIG. 52B is a partially-exploded side cross-sectional view of a syringe having a pressure jacket, a rolling diaphragm, and plunger in accordance with another aspect of the present disclosure.

FIGS. 52A-52B are partially-exploded side cross-sectional views of a syringe 104 having a pressure jacket 110, a rolling diaphragm 112, and plunger 144 in accordance with another aspect of the present disclosure. The components of the syringe 104 shown in 52A-52B are substantially similar to the components of the syringe 104 described above with reference to FIGS. 48A-48B. Reference numerals in 52A-52B are used to illustrate identical components as the corresponding reference numerals in FIGS. 48A-48B. As the previous discussion regarding the syringe 104 generally shown in FIGS. 48A-48B is applicable to the aspect shown in 52A-52B, only the relevant differences between these systems are discussed hereinafter. FIG. 52a illustrates a syringe 104 having a substantially cylindrical pressure jacket 110. According to various embodiments, the cap 152 has a closure member 168 that is removably connected to the cap 152. The closure member 168 may optionally be formed integrally with the cap 152 while still being removably connected to the cap 152. Prior to use, the closure member 168 engages the cap 152 to seal the cap 152 and prevent contamination thereof. The closure member 168 is then removed to allow the cap 152 to be pierced by piercing member 156 and connected to the fluid path set (not shown). After use, the closure member 168 can be reconnected to the cap 152 to prevent any remaining fluid from spilling from the cap 152.

Figure 53:
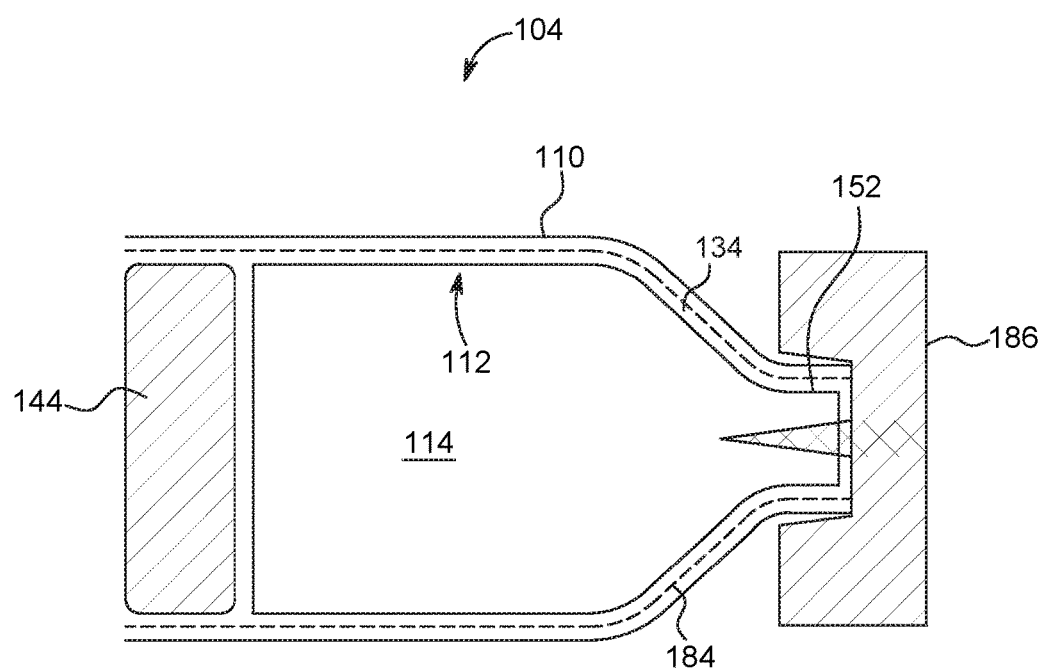
FIG. 53 is a cross-sectional side view of a syringe in accordance with another aspect of the present disclosure.

FIG. 53 is a cross-sectional side view of a syringe 104 in accordance with another aspect of the present disclosure. The syringe 104 has a rolling diaphragm 112 that is encapsulated within the pressure jacket 110 with a fluid sleeve 184 disposed between the sidewall 134 of the rolling diaphragm 112 and the pressure jacket 110. The fluid sleeve 184 is filled around the rolling diaphragm 112 after it is disposed within the pressure jacket 110. The cap 152 encloses the fluid sleeve 184 within the pressure jacket 110. The proximal end of the pressure jacket 110 may be sealed with a second cap 186 to prevent the fluid sleeve 184 from leaking through the proximal end of the pressure jacket 110.

Figure 55A:
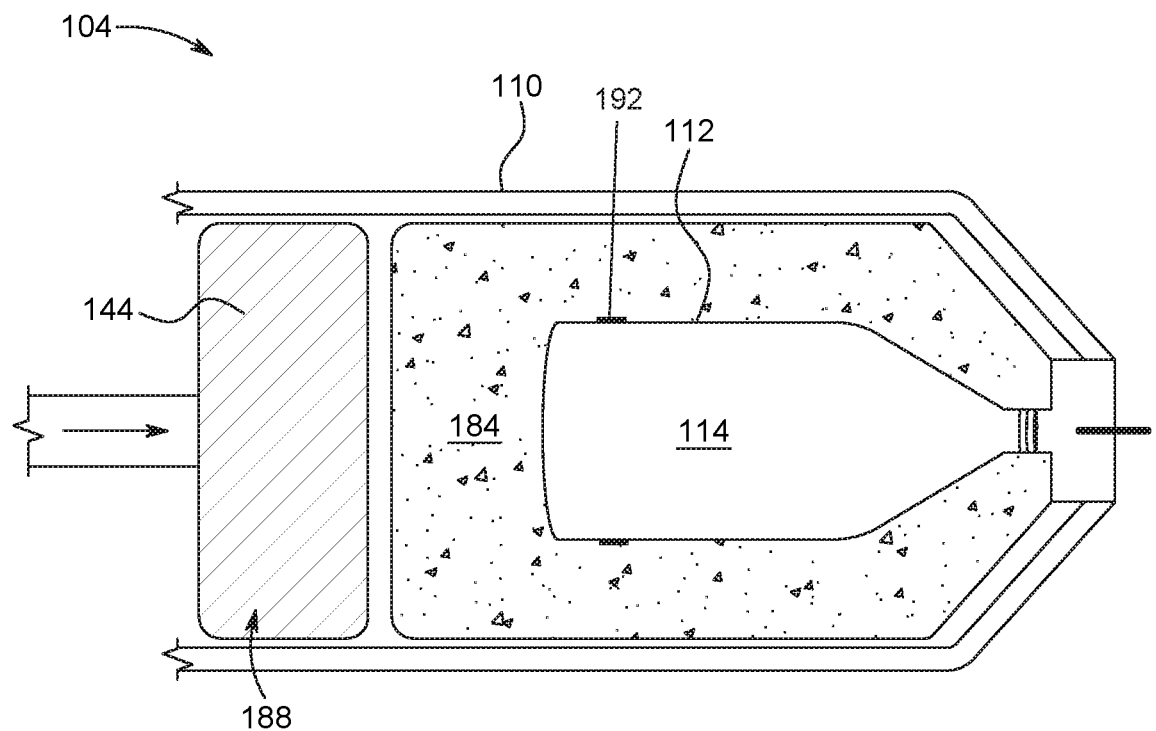
FIG. 55A is a cross-sectional side view of a syringe in accordance with another aspect of the present disclosure.
Figure 55B:
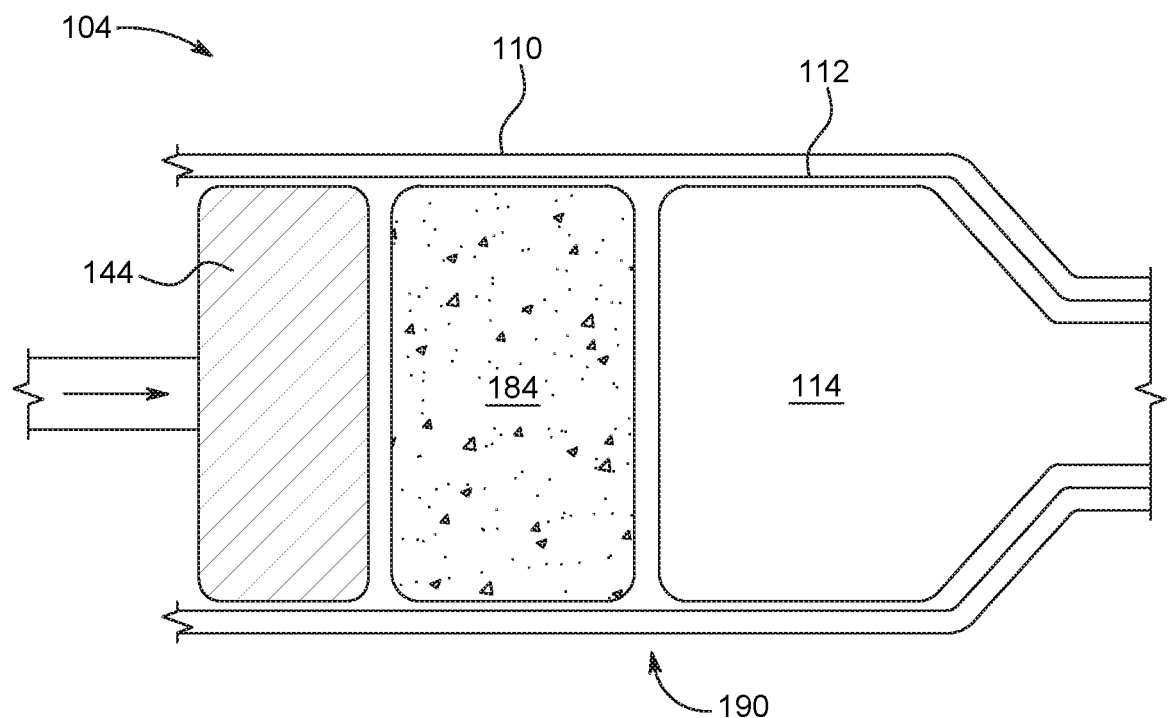
FIG. 55B is a cross-sectional side view of a syringe in accordance with another aspect of the present disclosure.

FIGS. 55A-55B are a cross-sectional side views of a syringe 104 in accordance with another aspect of the present disclosure. With reference to FIGS. 55A-55B, the fluid sleeve 184 may be in the form of a bag that surrounds the rolling diaphragm 112 within the pressure jacket 110 (FIG. 55A) or as a bag proximal to rolling diaphragm 112 (FIG. 55B). The plunger 144 has a check valve 188 to allow a retraction of the plunger 144 after fluid from the rolling diaphragm 112 is delivered. A sensor 190 may be provided within the pressure jacket 110 to detect a rupture of the fluid sleeve 184 or the rolling diaphragm 112. With reference to FIG. 55A, the rolling diaphragm 112 has a correspondingly-shaped fluid sleeve 184 provided along a longitudinal length of the rolling diaphragm 112. In one aspect, the fluid sleeve 184 may be a mirror copy of the rolling diaphragm 112. When inserted into the injector 102 (not shown), the rolling diaphragm 112 is fluidly connected to a fluid path set (not shown). During an injection procedure, the fluid sleeve 184 functions as a compression surface to drive the fluid from the interior volume 114 of the rolling diaphragm 112. In particular, a portion of the injector 102, such as the plunger 144, acts on the fluid sleeve 184 to compress the fluid sleeve 184 against the rolling diaphragm 112. In this manner, the compression force of the fluid sleeve 184 is evenly distributed across the entire surface of the rolling diaphragm 112 to minimize the residual volume of fluid remaining in the rolling diaphragm 112. Gripping tabs 192 may be provided on one or both lateral portions of the fluid sleeve 184 and the rolling diaphragm 112 to facilitate handling of the assembly.

Figure 54:
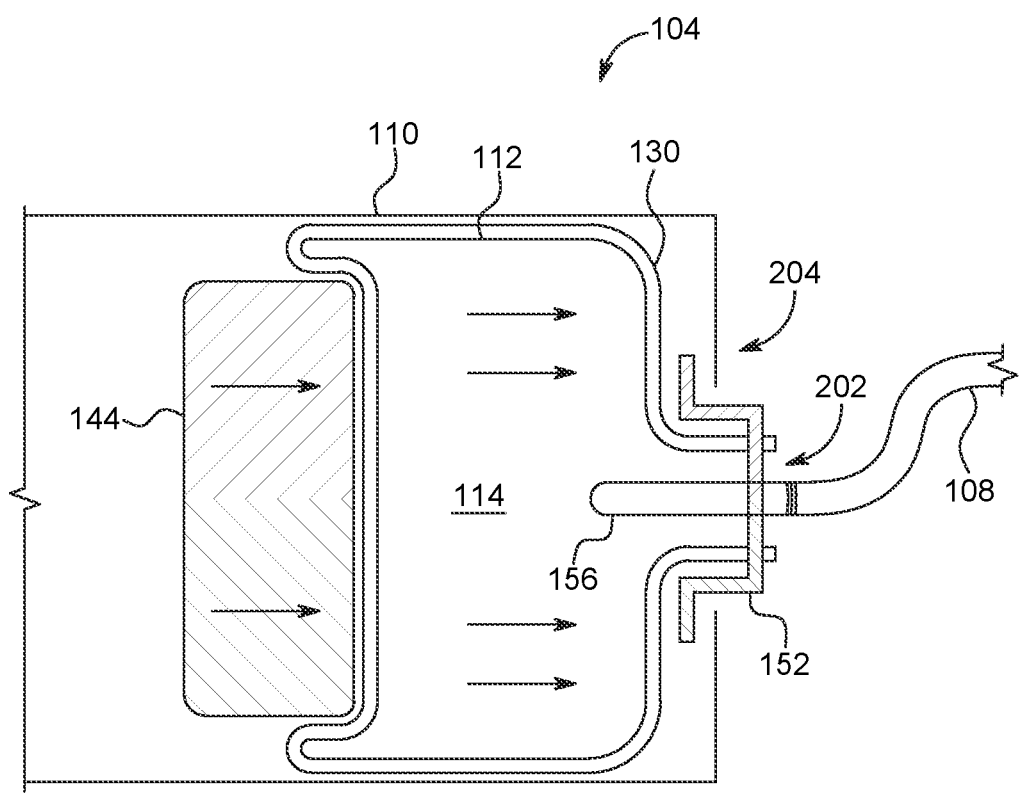
FIG. 54 is a cross-sectional side view of a syringe in accordance with another aspect of the present disclosure.
Figure 56A:
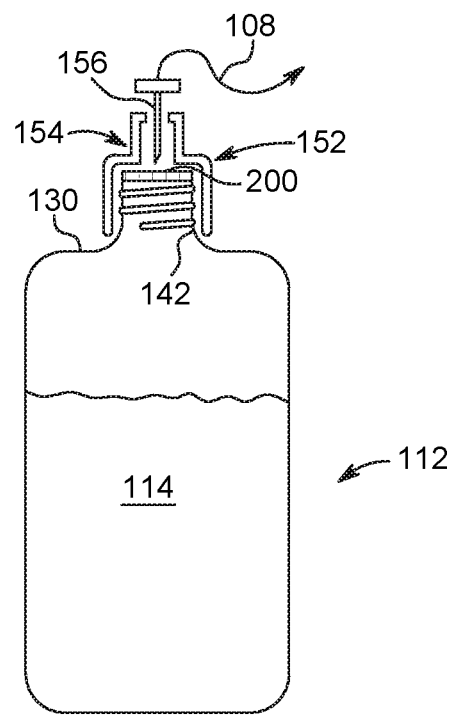
FIG. 56A is a cross-sectional side view of a syringe in accordance with another aspect of the present disclosure.
Figure 56B:
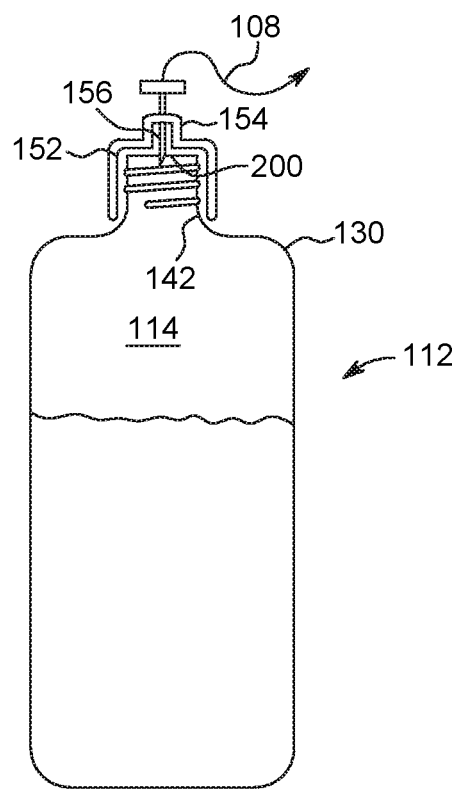
FIG. 56B is a cross-sectional side view of a syringe in accordance with another aspect of the present disclosure.
Figure 57:
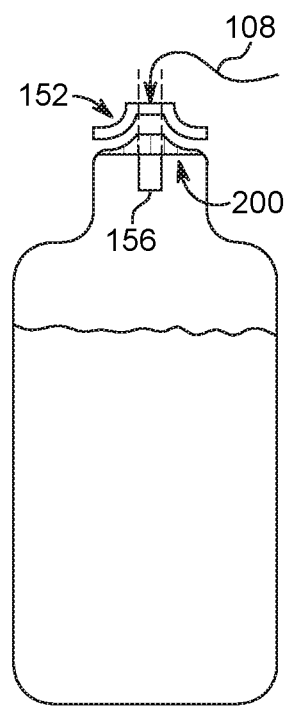
FIG. 57 is a cross-sectional side view of a syringe in accordance with another aspect of the present disclosure.

FIGS. 56A-56B are cross-sectional side views of a syringe 104 in accordance with another aspect of the present disclosure. The rolling diaphragm 112 has a cap 152 that may be molded, adhered, screwed, or otherwise mechanically coupled to the distal end 130 of the rolling diaphragm 112. Desirably, the connection between the cap 152 and the distal end 130 of the rolling diaphragm 112 is formed to withstand typical injection pressures. The cap 152 has a connector 154, such as a luer-type connector, for connecting to a fluid path set 108. In one aspect, the fluid path set includes a corresponding connector for coupling to the connector 154 on the cap 152. A piercing needle 156 is provided on the fluid path set 108 to allow piercing of a frangible seal 200 on the cap 152 which seals the discharge port 142 of the rolling diaphragm 112. In the aspect shown in FIG. 56B, the piercing needle 156 may be built into the cap 152. Once the frangible seal 200 is pierced, the interior volume 114 of the rolling diaphragm 112 is fluidly connected with the fluid path set 108. With reference to FIG. 54, the rolling diaphragm 112 has a high-pressure seal 202 at its distal end 130 and the cap 152 has a low-pressure seal 204.

FIG. 58A is a cross-sectional side view of a syringe in accordance with another aspect of the present disclosure. FIG. 58B is a partial cross-sectional perspective view of a seal shown in FIG. 58A. The discharge neck 140 of the rolling diaphragm 112 has a seal 200 that abuts against a seal 200a of the cap 152 to create a double-seal arrangement. The cap 152 is desirably attached to the discharge neck 140 in one of the plurality of ways described herein. The cap 152 has a connection member 212, formed as a plurality of external threads that threadably engage with the internal threads of the fluid path set 108. The piercing needle 156 is formed on the terminal end of the fluid path set 108 for piercing through the double-seal arrangement in order to establish fluid communication between the interior volume 114 of the rolling diaphragm 112 and the fluid path set 108.

Figure 59:
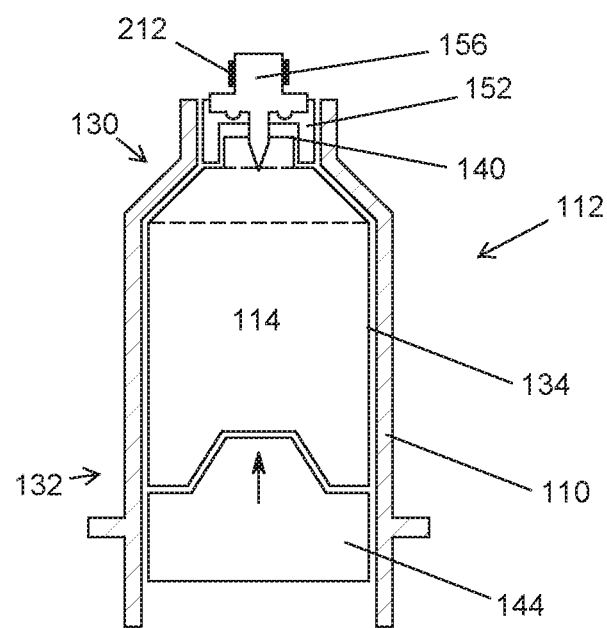
FIG. 59 is a side cross-sectional view of a syringe in accordance with another aspect of the present disclosure.

With reference to FIG. 59 is a cross-sectional side view of a syringe in accordance with another aspect of the present disclosure. The discharge neck 140 of the rolling diaphragm 112 is initially sealed. The cap 152 is attachable to the pressure jacket 110 such that a piercing needle 156 of the cap 152 may pierce the sidewall 134 of the rolling diaphragm 112 at the discharge neck 140. In some aspects, the cap 152 may have a connection member 212, formed as a plurality of external threads that threadably engage with the internal threads of the fluid path set 108 (not shown). The piercing needle 156 is formed on the terminal end of the cap 152 for piercing through the sidewall 134 of the rolling diaphragm 112 in order to establish fluid communication between the interior volume 114 of the rolling diaphragm 112.

Figure 60A:
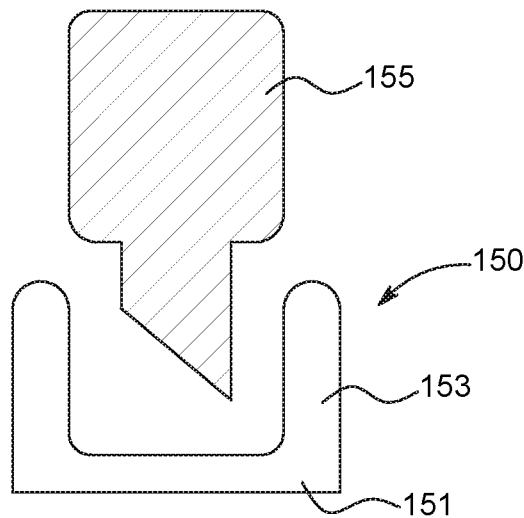
FIG. 60A is a side cross-sectional view of a seal for use with a syringe in accordance with another aspect of the present disclosure, with a seal piercing element shown in a first position.
Figure 60B:
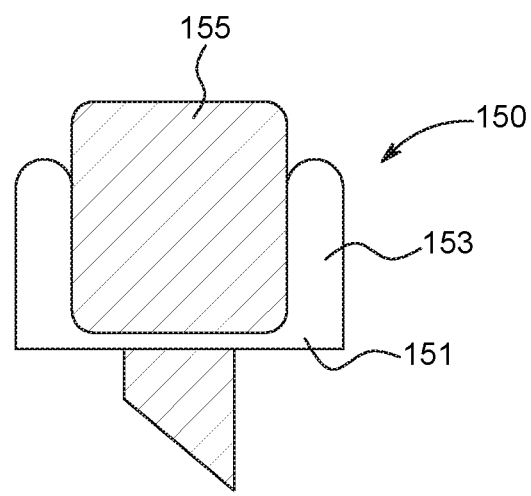
FIG. 60B is a side cross-sectional view of the seal shown in FIG. 60B, with the seal piercing element shown in a second position.

FIG. 60A is a side cross-sectional view of a seal for use with a syringe and rolling diaphragm in accordance with another aspect of the present disclosure, with a seal piercing element shown in a first sealed position. FIG. 60B is a side cross-sectional view of the seal shown in FIG. 60B, with the seal piercing element shown in a second pierced position. The seal 150 may have a base 151 and a sidewall 153 protruding substantially perpendicularly relative to the base 151. The base 151 is pierceable by a piercing element 155, such as a spike provided on a fluid path set. Once the piercing element 155 pierces the base 151, the base 151 fluidly seals around the circumference of the seal 150. In addition, a body 157 of the piercing element 155 engages the sidewall 153 of the seal 150 to provide a secondary seal.

Figure 61:
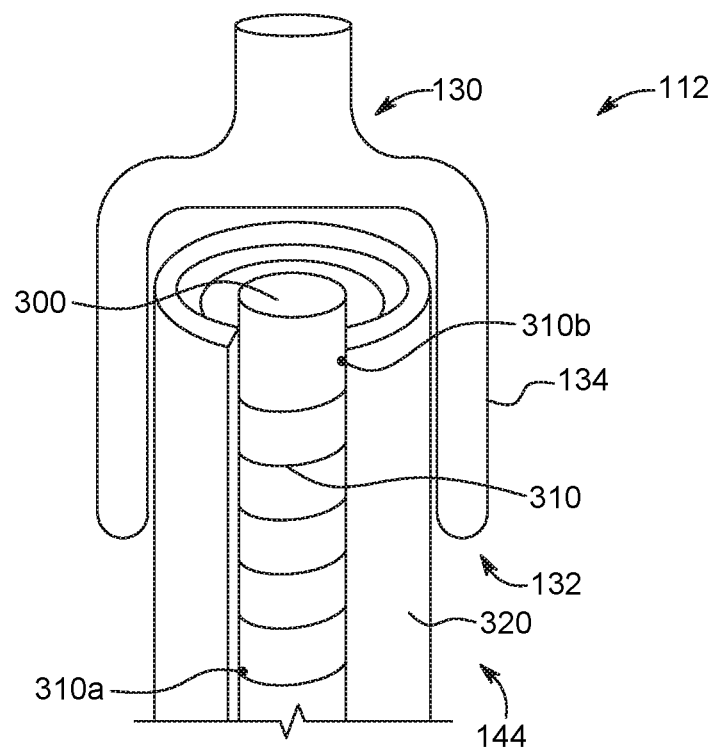
FIG. 61 is a side cross-sectional view of a rolling diaphragm and a plunger in accordance with another aspect of the present disclosure.

FIG. 61 is a cross-sectional side view of a rolling diaphragm 112 and a plunger 144 in accordance with another aspect of the present disclosure. The plunger 144 has an inner element 300 and an elastic element 310 wrapped around at least a portion of the inner element 300. One end of the elastic element 310, such as a proximal end 310a or a distal element 310b, may be secured to the inner element 300, while the opposing end of the elastic element 310 is free to rotate about the inner element 300. Upon rotation of one end of the elastic element 310 around the inner element 300 in a first direction, such as a clockwise or a counterclockwise direction, the elastic element 310 may be expanded radially outward to engage an inner surface of an outer element 320 that surrounds the inner element 300 and the elastic element 310. The outer element 320 may be formed as a split cylinder with a slit extending along its longitudinal axis. An outer surface of the outer element 320 engages the sidewall 134 of the rolling diaphragm 112. Thus, as the elastic element 310 expands against the inner surface of the outer element 320, the outer element 320 expands radially outward such that its outer surface engages the sidewall 134 of the rolling diaphragm 112. In this manner, the plunger 144 may move the sidewall 134 of the rolling diaphragm 112 to withdraw fluid or expel fluid from the interior volume 114 of the rolling diaphragm 112. In some aspects, the elastic element 310, in the expanded state, may engage the sidewall 134 of the rolling diaphragm 112. Upon rotation of the elastic element 310 around the inner element 300 in a second direction opposite the first direction, the elastic element 310 may contract radially inward, thereby disengaging the outer element 320. In some aspects, the elastic element 310, in the contracted state, may disengage the sidewall 134 of the rolling diaphragm 112.

Figure 62:
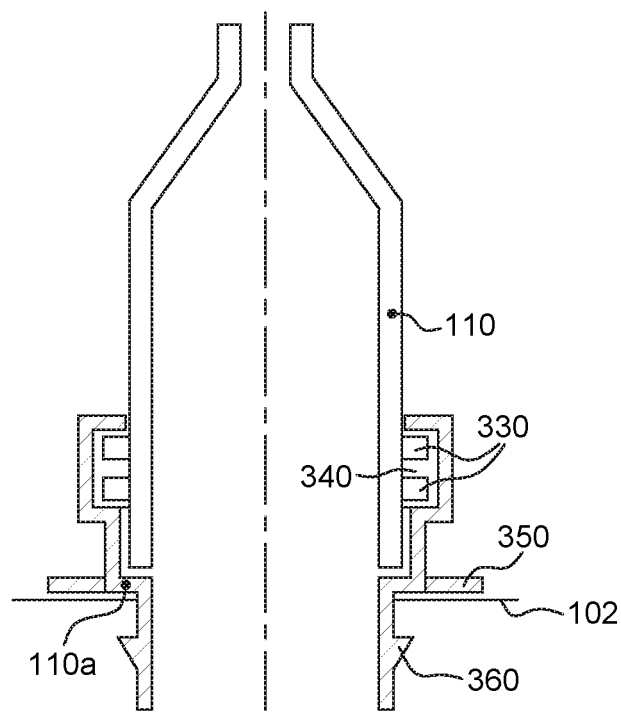
FIG. 62 is a side cross-sectional view of a pressure jacket in accordance with another aspect of the present disclosure.

FIG. 62 is a cross-sectional side view of a pressure jacket 110 in accordance with another aspect of the present disclosure. The pressure jacket 110 may have an adapter 110a for releasably connecting the pressure jacket 110 with the injector 102. An outer sidewall of the pressure jacket 110 has one or more tabs 330 that protrude radially outward relative to the outer sidewall. The one or more tabs 330 are received in corresponding slots 340 or engagement mechanism formed on the adapter 110a. In some aspects, the pressure jacket 110 may be secured to the adapter 110a by inserting the pressure jacket 110 into a central opening on the adapter 110a and rotating the pressure jacket 110 relative to the adapter 110a in a first direction (such as ¼ of a turn in a clockwise or a counterclockwise direction) until the tabs 330 are received within the slots 340. Once received, the tabs 330 retain the pressure jacket 110 locked with the adapter 110a until the pressure jacket 110 is rotated in a second direction opposite the first direction (such as ¼ of a turn in a counterclockwise or a clockwise direction). The adapter 110a may have a radial flange 350 protruding from an outer sidewall to prevent fluid from dripping into the injector 102. One or more locking elements 360 may be provided on the adapter 110a to removably lock the adapter 110a with a corresponding locking mechanism on the injector 102. In some aspects, the adapter 110a may be removably locked with the injector 102, such as by a bayonet connection.

Figure 63A:
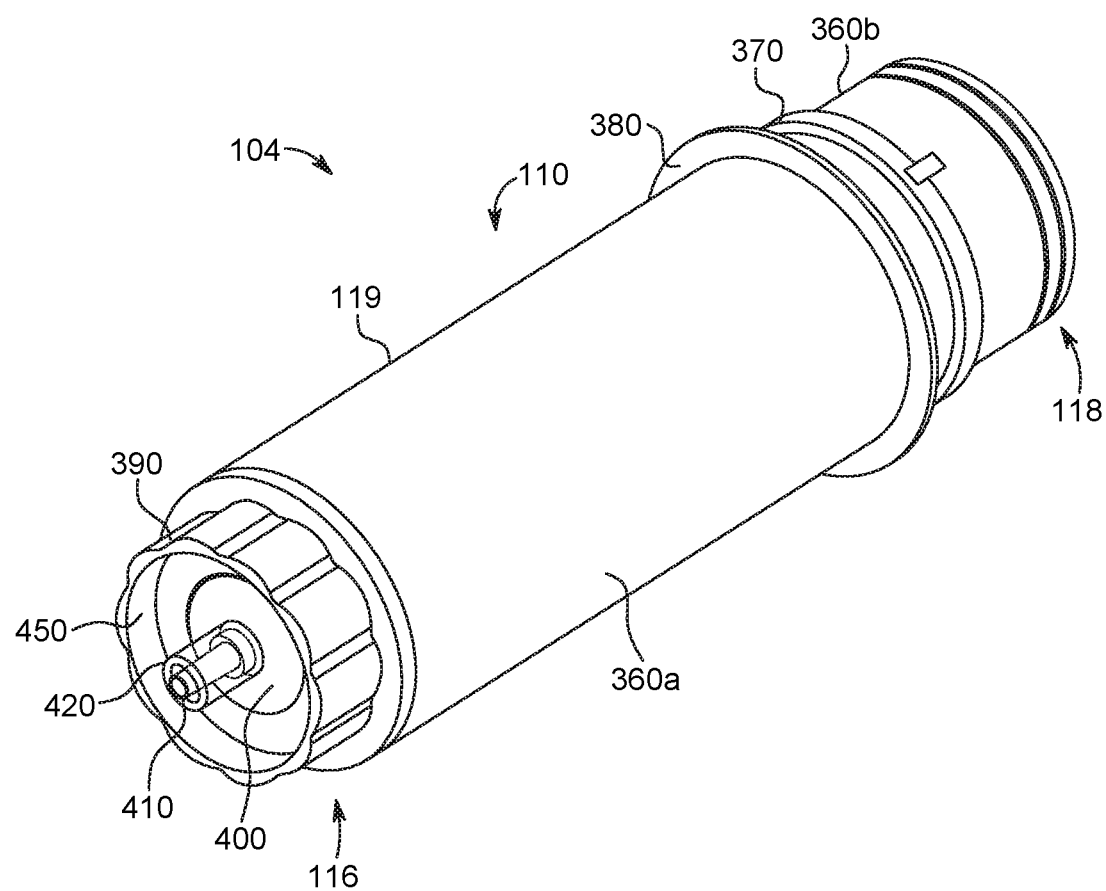
FIG. 63A is a perspective view of a syringe having a pressure jacket in accordance with another aspect of the present disclosure.
Figure 63B:
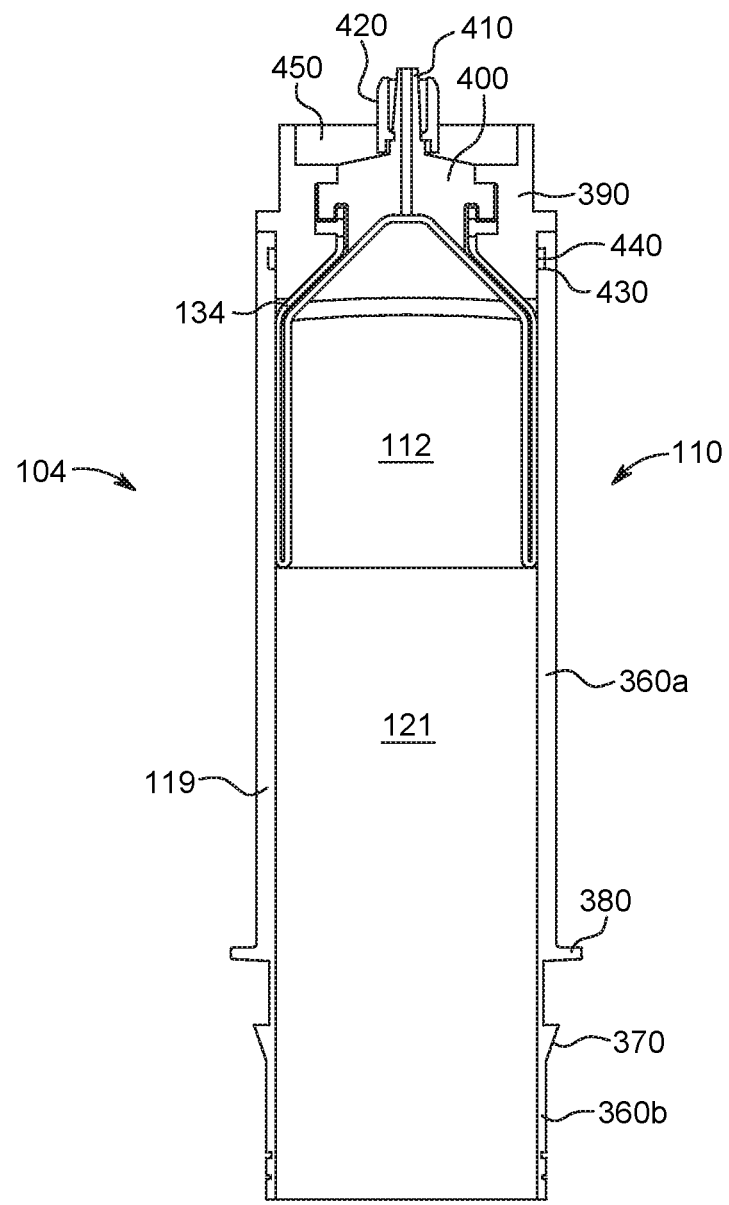
FIG. 63B is a cross-sectional side view of the syringe shown in FIG. 63A.
Figure 63C:
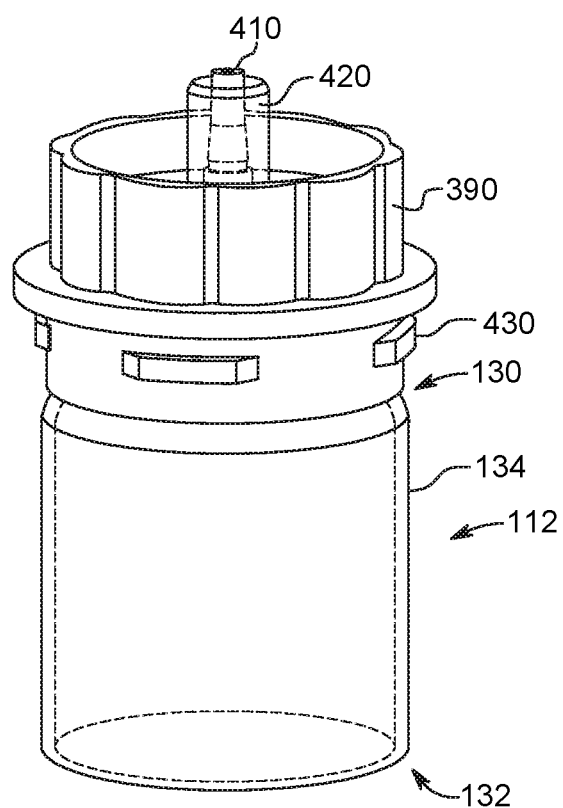
FIG. 63C is a perspective view of a rolling diaphragm for use with the pressure jacket shown in FIG. 63A.

FIG. 63A is a perspective view of a syringe having a pressure jacket 110 in accordance with another aspect of the present disclosure. FIG. 63B is a cross-sectional side view of the syringe shown in FIG. 63A. FIG. 63C is a perspective view of a rolling diaphragm 112 for use with the pressure jacket 110 shown in FIG. 63A. The syringe 104 includes the pressure jacket 110 that removably interfaces with the injector 102 (shown in FIG. 1), as described herein. The pressure jacket 110 has a distal end 116, a proximal end 118, and a sidewall 119 extending between the distal end 116 and the proximal end 118 along a longitudinal axis of the pressure jacket 110 to define an internal throughbore 121 (shown in FIG. 63B). In some aspects, the sidewall 119 of the pressure jacket 110 is shaped to receive at least a portion of the rolling diaphragm 112 (shown in FIG. 63B) within the throughbore 121. The pressure jacket 110 is typically a reusable component, while the rolling diaphragm 112 is typically a single-use component. In another aspect, the rolling diaphragm 112 may be reusable such that the rolling diaphragm 112 is refillable with fluid. The sidewall 119 of the pressure jacket 110 has a first distal portion 360a for receiving at least a portion of the rolling diaphragm 112, and a second proximal portion 360b for interfacing with the injector 102. In some aspects, the second distal portion 360b has a locking lug or lip 370 protruding radially outward from an outer surface of the second proximal portion 360b. The locking lug or lip 370 may extend continuously or discontinuously around an outer circumference of the second proximal portion 360b. In some aspects, the locking lug or lip 110 may have a connection interface to releasably secure the pressure jacket 110 to a corresponding locking mechanism of the fluid injector 102 described in U.S. Pat. No. 5,383,858 to Reilly et al.; U.S. Pat. No. 5,873,861 to Hitchins et al.; and U.S. Pat. No. 6,652,489 to Trocki et al., U.S. patent application Ser. No. 14/526,294, entitled "Self-Orienting Syringe and Syringe Interface", and U.S. patent application Ser. No. 14/526,395, entitled "Self-Orienting Syringe and Syringe Interface", the disclosures of which are incorporated herein by reference in their entirety.

With reference to FIG. 63B, the pressure jacket 110 has a cap 390 that is releasably secured to the distal end 116. In some aspects, the cap 390 may be secured by a threaded engagement, a bayonet fitting, or another mechanical fastening arrangement with the distal end 116 of the pressure jacket 110. For example, the cap 390 may have at least one projection 430 that is received inside at least one groove 440 on the pressure jacket 110 such that the cap 390 may be locked with the pressure jacket 110 by aligning the at least one projection 430 to fit within the groove 440. In some aspects, the cap 390 may be formed from two or more separate elements that are joined together to form the cap 390. For example, the cap 390 may have two elements joined together at a longitudinal cross-sectional plane of the cap 390. A ring may be provided around at least a portion of the separate elements to retain the elements of the cap 390. The cap 390 may have an inner element 400 with a nozzle 410 extending through the cap 390. The nozzle 410 may be in fluid communication with the rolling diaphragm 112 to deliver fluid into or from the rolling diaphragm 112. The nozzle 410 may have a connection interface for removably connecting to a connector 420 of a fluid path set 108 (shown in FIG. 1). The cap 390 may have a pocket 450 for collecting any fluid that may drip from the nozzle 410 and/or the connector 420.

With reference to FIG. 63C, at least a portion of the rolling diaphragm 112 may be removably secured to the cap 390. In some aspects, an inner sidewall of the cap 390 may have one or more threads 440 (shown in FIG. 64B) that engage the corresponding threads 140b (shown in FIG. 5A) on the rolling diaphragm 112. In other aspects, the rolling diaphragm 112 may be secured to the cap 390 by a snap-fit, interference fit, adhesive connection, co-molding or any other mechanical fastening arrangement. The rolling diaphragm 112 may have a built-in cap 390. The rolling diaphragm 112 may be pre-filled with fluid, or may be empty such that it can be filled with fluid. In various aspects, the rolling diaphragm 112 may be removably or non-removably connected to the cap 390. Desirably, the rolling diaphragm 112 is secured to the cap 390 prior to being inserted into the throughbore 121 of the pressure jacket 110. After securing the cap 390 to the pressure jacket 110, the plunger 144 (shown in FIG. 2) may engage the rolling diaphragm 112 to deliver fluid into or from the rolling diaphragm 112, as described herein.

Figure 64A:
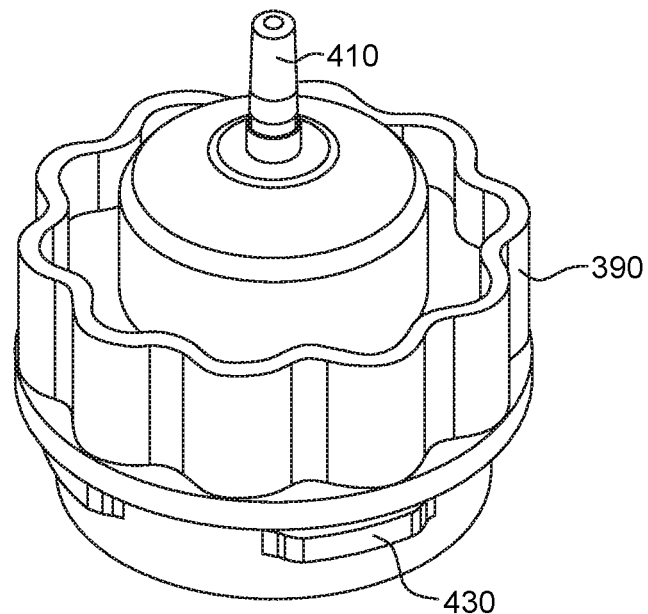
FIG. 64A is a top perspective view of an alternative embodiment for a cap for use with the pressure jacket shown in FIG. 63A.
Figure 64B:
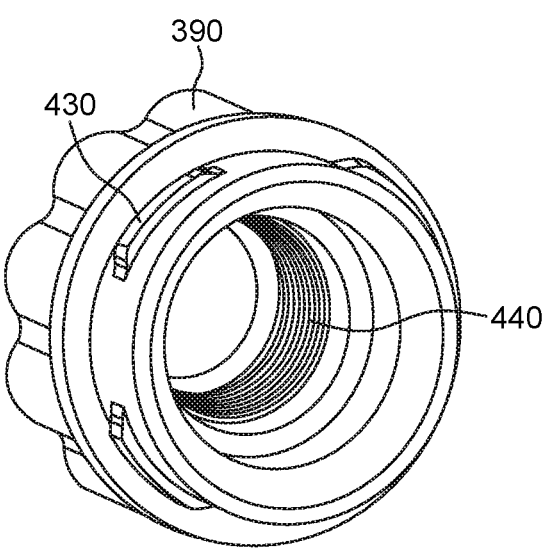
FIG. 64B is a bottom perspective view of the cap shown in FIG. 64A.

FIG. 64A is a top perspective view of an alternative embodiment for the cap 390 for use with the pressure jacket 110 shown in FIG. 63A. The cap 390 may have a one-piece configuration with a threaded interface for connecting the rolling diaphragm 112 to the cap 390.

While aspects of a fluid delivery system and a syringe having a rolling diaphragm for use therefor were provided in the foregoing description, those skilled in the art may make modifications and alterations to these aspects without departing from the scope and spirit of the disclosure. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

We claim:

1. A syringe for a fluid delivery system, the syringe comprising:
   a pressure jacket having a distal end, a proximal end, and a throughbore extending between the distal end and the proximal end; and
   a rolling diaphragm disposed within the throughbore of the pressure jacket, the rolling diaphragm having a proximal end having a concave end wall shaped for engagement with a plunger, a distal end received at the distal end of the pressure jacket, the distal end of the rolling diaphragm having a discharge neck, and a sidewall extending between the proximal end and the distal end of the rolling diaphragm along a longitudinal axis, at least one of the end wall and at least a portion of the sidewall having a non-uniform thickness,
   wherein at least a portion of the sidewall of the rolling diaphragm is flexible and rolls upon itself such that an outer surface of the sidewall at a folding region is folded in a radially inward direction as the plunger is advanced from the proximal end to the distal end of the rolling diaphragm and such that the outer surface of the sidewall unrolls as the folding region is unfolded in a radially outward direction as the plunger is retracted from the proximal end to the distal end of the rolling diaphragm,
   wherein the concave end wall of the rolling diaphragm has a plunger engagement portion that protrudes proximally from the concave end wall such that the plunger engagement portion is at least partially recessed within a cavity defined by the concave end wall at least in an unrolled state or a rolled state of the rolling diaphragm and prior to engagement with the plunger, and
   wherein the concave end wall has a radiused folding edge that transitions into a distally extending ramp having a continuously increasing thickness.

2. The syringe of claim 1, wherein the pressure jacket has a removable closure for enclosing at least a portion of the rolling diaphragm.

3. The syringe of claim 2, wherein the removable closure has a threaded end for engaging corresponding threads on the distal end of the pressure jacket or wherein the removable closure has one or more radially extending tabs for insertion into corresponding slots for engaging a bayonet locking mechanism on the distal end of the pressure jacket.

4. The syringe of claim 2, wherein the proximal end of the pressure jacket has a connection interface for releasably connecting to a fluid injector.

5. The syringe of claim 1, wherein the plunger engagement portion protrudes proximally from a central region of the ramp.

6. The syringe of claim 1, wherein the concave end wall has one or more ribs protruding radially outward from a surface of the concave end wall and extending from the plunger engagement portion toward the radiused folding edge.

7. The syringe of claim 1, wherein the plunger engagement portion is received within an opening on a plunger of a fluid injector.

8. The syringe of claim 7, wherein the plunger engagement portion is releasably retained with at least a portion of the plunger.

9. The syringe of claim 7, wherein at least a portion of the plunger engagement portion is expanded radially outward to releasably retain the plunger engagement portion within the opening of the plunger.

10. The syringe of claim 1, wherein a first portion of the sidewall distal of an approximate midpoint of the rolling diaphragm has a first thickness, wherein a second portion of the sidewall proximal of the approximate midpoint of the rolling diaphragm has a second thickness, and wherein the first thickness is greater than the second thickness.

11. The syringe of claim 1, wherein the proximal end has a rigid plunger monolithically formed with the proximal end.

12. The syringe of claim 1, wherein an interior of the rolling diaphragm is pre-filled with a medical fluid.

13. The syringe of claim 1, wherein the discharge neck has a connector for connecting to a fluid path set.

14. The syringe of claim 13, wherein the connector is a luer connector.

15. The syringe of claim 1, wherein the rolling diaphragm is installed in the rolled configuration.

16. The syringe of claim 15, wherein the concave end wall of the rolling diaphragm in the rolled configuration is moved a proximal direction to fill the rolling diaphragm with a volume of a medical fluid.

* * * * *

UNITED STATES PATENT AND TRADEMARK OFFICE
CERTIFICATE OF CORRECTION

PATENT NO. : 11,717,614 B2
APPLICATION NO. : 16/812912
DATED : August 8, 2023
INVENTOR(S) : Berry et al.

It is certified that error appears in the above-identified patent and that said Letters Patent is hereby corrected as shown below:

In the Specification

In Column 1, Line 6, delete "2016," and insert -- 2016, now U.S. Pat. No. 10,583,256, --, therefor.
In Column 1, Line 61, delete "Mill," and insert -- MRI, --, therefor.
In Column 2, Line 29, delete "thickness" and insert -- thickness. --, therefor.
In Column 7, Line 20, delete "view" and insert -- view of --, therefor.
In Column 7, Line 23, delete "view" and insert -- view of --, therefor.
In Column 7, Line 25, delete "view" and insert -- view of --, therefor.
In Column 7, Line 27, delete "view" and insert -- view of --, therefor.
In Column 11, Line 31, delete "FIG. 60B," and insert -- FIG. 60A, --, therefor.
In Column 13, Line 47, delete "Mill," and insert -- MRI, --, therefor.
In Column 16, Line 3, delete "polyproplylene" and insert -- polypropylene --, therefor.
In Column 16, Lines 3-4, delete "polyproplylene" and insert -- polypropylene --, therefor.
In Column 16, Line 4, delete "polyproplylene" and insert -- polypropylene --, therefor.
In Column 16, Line 6, delete "HPDE," and insert -- HDPE, --, therefor.
In Column 16, Line 26, delete "blow-mold-seal" and insert -- blow-fill-seal --, therefor.
In Column 16, Line 35, delete "contaminates" and insert -- contaminants --, therefor.
In Column 17, Line 15, delete "view" and insert -- view of --, therefor.
In Column 25, Line 65, delete "FIG. 23-24A is a cross-sectional side view" and insert -- FIGS. 23-24A are cross-sectional side views --, therefor.
In Column 26, Line 34, delete "27-28C is a cross-sectional side view" and insert -- 27-28C are cross-sectional side views --, therefor.
In Column 27, Line 13, delete "rolling diaphragm 112p" and insert -- rolling diaphragm 112 --, therefor.
In Column 29, Lines 20-21, delete "second engagement portion 244a." and insert -- second engagement portion 244b. --, therefor.
In Column 29, Line 36, delete "tab 244c" and insert -- tab --, therefor.
In Column 29, Line 37, delete "lip 244d" and insert -- ledge 244d --, therefor.
In Column 29, Line 38, delete "tab 244c" and insert -- tab --, therefor.

Signed and Sealed this
Thirtieth Day of January, 2024

Katherine Kelly Vidal
*Director of the United States Patent and Trademark Office*

In Column 29, Lines 39-40, delete "second engagement portion 244d" and insert -- second engagement portion 244b --, therefor.
In Column 29, Line 42, delete "lip 244d" and insert -- ledge 244d --, therefor.
In Column 29, Line 45, delete "lip 244d" and insert -- ledge 244d --, therefor.
In Column 30, Line 44, delete "moved" and insert -- moved and --, therefor.
In Column 31, Line 20, delete "legs 244c" and insert -- legs --, therefor.
In Column 31, Line 21, delete "legs 244c" and insert -- legs --, therefor.
In Column 31, Line 26, delete "recess" and insert -- recess 244f --, therefor.
In Column 31, Line 26, delete "leg 244c" and insert -- leg --, therefor.
In Column 31, Line 35, delete "leg 244c" and insert -- leg --, therefor.
In Column 31, Line 36, delete "recess" and insert -- recess 244f --, therefor.
In Column 31, Line 38, delete "leg 244c" and insert -- leg --, therefor.
In Column 31, Line 39, delete "recess" and insert -- recess 244f --, therefor.
In Column 31, Line 41, delete "leg 244c" and insert -- leg --, therefor.
In Column 31, Line 42, delete "recess" and insert -- recess 244f --, therefor.
In Column 34, Line 65, delete "hinge 104" and insert -- hinge 166 --, therefor.
In Column 35, Line 38, delete "52A-52B" and insert -- FIGS. 52A-52B --, therefor.
In Column 35, Lines 40-41, delete "52A-52B" and insert -- FIGS. 52A-52B --, therefor.
In Column 35, Line 45, delete "52A-52B," and insert -- FIGS. 52A-52B, --, therefor.
In Column 35, Lines 55-56, delete "piercing member 156" and insert -- piercing needle 156 --, therefor.
In Column 37, Line 21, delete "FIG. 60B," and insert -- FIG. 60A, --, therefor.
In Column 38, Line 46, delete "second distal portion 360b" and insert -- second proximal portion 360b --, therefor.
In Column 38, Lines 51-52, delete "locking lug or lip 110" and insert -- locking lug or lip 370 --, therefor.

In the Claims

In Column 41, Line 6, in Claim 16, delete "moved" and insert -- moved in --, therefor.